United States Patent
Bosse et al.

(10) Patent No.: US 9,526,704 B2
(45) Date of Patent: *Dec. 27, 2016

(54) PHARMACEUTICAL COMPOSITIONS FOR TREATING OR PREVENTING PAIN

(71) Applicant: LOCL Pharma, Inc., Las Vegas, NV (US)

(72) Inventors: Paul Bosse, Jupiter, FL (US); John Ameling, Jupiter, FL (US); Bernard Schachtel, Jupiter, FL (US); Ray Takigiku, Loveland, OH (US)

(73) Assignee: LOCL PHARMA, INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,955

(22) Filed: Jul. 11, 2016

(65) Prior Publication Data

US 2016/0317447 A1 Nov. 3, 2016

Related U.S. Application Data

(63) Continuation of application No. 14/244,455, filed on Apr. 3, 2014, now Pat. No. 9,433,625, which is a continuation of application No. 12/967,423, filed on Dec. 14, 2010, now Pat. No. 8,728,522, which is a continuation-in-part of application No. PCT/US2010/041433, filed on Jul. 8, 2010.

(60) Provisional application No. 61/224,424, filed on Jul. 9, 2009, provisional application No. 61/223,999, filed on Jul. 8, 2009.

(51) Int. Cl.
| | | |
|---|---|---|
| A61K 31/167 | (2006.01) | |
| A61K 31/485 | (2006.01) | |
| A61K 31/5415 | (2006.01) | |
| A61K 9/24 | (2006.01) | |
| A61K 9/20 | (2006.01) | |

(52) U.S. Cl.
CPC ............. *A61K 9/209* (2013.01); *A61K 9/2013* (2013.01); *A61K 9/2054* (2013.01); *A61K 31/167* (2013.01); *A61K 31/485* (2013.01); *A61K 31/5415* (2013.01)

(58) Field of Classification Search
CPC A61K 2300/00; A61K 31/167; A61K 31/485; A61K 31/5415; A61K 9/2054; A61K 9/209
See application file for complete search history.

(56) References Cited

U.S. PATENT DOCUMENTS

| | | |
|---|---|---|
| 3,048,526 A | 8/1962 | Boswell |
| 3,108,046 A | 10/1963 | Harbit |
| (Continued) | | |

FOREIGN PATENT DOCUMENTS

| | | |
|---|---|---|
| CA | 2262267 A1 | 8/1999 |
| DE | 102005013726 A1 | 9/2006 |
| (Continued) | | |

OTHER PUBLICATIONS

US 8,975,271, 03/2015, Oshlack et al. (withdrawn)
(Continued)

*Primary Examiner* — Ernst V Arnold
(74) *Attorney, Agent, or Firm* — Wilson Sonsini Goodrich & Rosati

(57) ABSTRACT

Methods and compositions are provided which comprise effective amounts of one or more analgesics, such as hydrocodone or acetaminophen, and an antiemetic, such as promethazine, to treat or prevent pain in a subject, and to reduce or prevent an adverse effect associated with the analgesics.

57 Claims, 8 Drawing Sheets

(56) References Cited

U.S. PATENT DOCUMENTS

| | | |
|---|---|---|
| 3,536,809 A | 10/1970 | Norman |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,113,866 A | 9/1978 | Lednicer |
| 4,265,875 A | 5/1981 | Byrne et al. |
| 4,478,822 A | 10/1984 | Haslam et al. |
| 4,532,126 A | 7/1985 | Ebert et al. |
| 4,588,580 A | 5/1986 | Gale et al. |
| 4,624,665 A | 11/1986 | Nuwayser |
| 4,625,494 A | 12/1986 | Iwatschenko et al. |
| 4,626,539 A | 12/1986 | Aungst et al. |
| 4,671,953 A | 6/1987 | Stanley et al. |
| 4,685,911 A | 8/1987 | Konno et al. |
| 4,717,713 A | 1/1988 | Zatz et al. |
| 4,786,505 A | 11/1988 | Lovgren et al. |
| 4,788,055 A | 11/1988 | Fischer et al. |
| 4,800,083 A | 1/1989 | Hom et al. |
| 4,820,522 A | 4/1989 | Radebaugh et al. |
| 4,834,978 A | 5/1989 | Nuwayser |
| 4,853,211 A | 8/1989 | Kurobe et al. |
| 4,871,353 A | 10/1989 | Thomsen |
| 4,904,479 A | 2/1990 | Illum |
| 4,906,463 A | 3/1990 | Cleary et al. |
| 4,919,939 A | 4/1990 | Baker |
| 4,925,444 A | 5/1990 | Orkin et al. |
| 4,935,243 A | 6/1990 | Borkan et al. |
| 4,950,484 A | 8/1990 | Olthoff et al. |
| 5,013,726 A | 5/1991 | Ivy et al. |
| 5,055,461 A | 10/1991 | Kelleher et al. |
| 5,059,595 A | 10/1991 | Le Grazie |
| 5,073,543 A | 12/1991 | Marshall et al. |
| 5,120,548 A | 6/1992 | McClelland et al. |
| 5,266,331 A | 11/1993 | Oshlack et al. |
| 5,298,520 A | 3/1994 | Baker et al. |
| 5,354,556 A | 10/1994 | Sparks et al. |
| 5,373,022 A | 12/1994 | Fawzi et al. |
| 5,376,672 A | 12/1994 | Pilgrim |
| 5,393,773 A | 2/1995 | Craig et al. |
| 5,425,950 A | 6/1995 | Dandiker et al. |
| 5,445,829 A | 8/1995 | Paradissis et al. |
| 5,464,864 A | 11/1995 | King et al. |
| 5,468,504 A | 11/1995 | Schaeffer |
| 5,478,577 A | 12/1995 | Sackler et al. |
| 5,484,406 A | 1/1996 | Wong et al. |
| 5,508,042 A | 4/1996 | Oshlack et al. |
| 5,536,249 A | 7/1996 | Castellano et al. |
| 5,549,912 A | 8/1996 | Oshlack et al. |
| 5,554,639 A | 9/1996 | Craig et al. |
| 5,585,115 A | 12/1996 | Sherwood et al. |
| 5,591,767 A | 1/1997 | Mohr et al. |
| 5,602,162 A | 2/1997 | Baker et al. |
| 5,610,184 A | 3/1997 | Shahinian, Jr. |
| 5,629,333 A | 5/1997 | Young |
| 5,635,204 A | 6/1997 | Gevirtz et al. |
| 5,637,611 A | 6/1997 | King et al. |
| 5,639,476 A | 6/1997 | Oshlack et al. |
| 5,656,295 A | 8/1997 | Oshlack et al. |
| 5,674,533 A | 10/1997 | Santus et al. |
| 5,705,506 A | 1/1998 | Merlet et al. |
| 5,705,520 A | 1/1998 | Craig et al. |
| 5,712,302 A | 1/1998 | Young |
| 5,733,556 A | 3/1998 | Schrier et al. |
| 5,738,874 A | 4/1998 | Conte et al. |
| 5,741,510 A | 4/1998 | Rolf et al. |
| 5,827,852 A | 10/1998 | Russell et al. |
| 5,827,871 A | 10/1998 | King et al. |
| 5,837,284 A | 11/1998 | Mehta et al. |
| 5,840,731 A | 11/1998 | Mayer et al. |
| 5,854,270 A | 12/1998 | Gambhir |
| 5,863,559 A | 1/1999 | Phillips et al. |
| 5,863,922 A | 1/1999 | Mayer et al. |
| 5,866,161 A | 2/1999 | Childers et al. |
| 5,871,776 A | 2/1999 | Mehta |
| 5,891,885 A | 4/1999 | Caruso |
| 5,895,663 A | 4/1999 | Irwin et al. |
| 5,902,632 A | 5/1999 | Mehta |
| 5,919,479 A | 7/1999 | Zhang et al. |
| 5,929,059 A | 7/1999 | Sanger et al. |
| 5,954,700 A | 9/1999 | Kovelman |
| 5,962,494 A | 10/1999 | Young |
| 5,968,551 A | 10/1999 | Oshlack et al. |
| 6,020,001 A | 2/2000 | Phillips et al. |
| 6,063,802 A | 5/2000 | Winterborn |
| 6,146,361 A | 11/2000 | DiBiasi et al. |
| 6,160,020 A | 12/2000 | Ohannesian et al. |
| 6,228,398 B1 | 5/2001 | Devane et al. |
| 6,228,863 B1 | 5/2001 | Palermo et al. |
| 6,255,502 B1 | 7/2001 | Penkler et al. |
| 6,258,380 B1 | 7/2001 | Overholt |
| 6,261,595 B1 | 7/2001 | Stanley et al. |
| 6,287,600 B1 | 9/2001 | Ouali et al. |
| 6,303,142 B1 | 10/2001 | Zhang et al. |
| 6,335,033 B2 | 1/2002 | Oshlack et al. |
| 6,341,387 B1 | 1/2002 | Zars |
| 6,348,216 B1 | 2/2002 | Kushla et al. |
| 6,368,627 B1 | 4/2002 | Phillips et al. |
| 6,372,254 B1 | 4/2002 | Ting et al. |
| 6,376,550 B1 | 4/2002 | Raber et al. |
| 6,465,006 B1 | 10/2002 | Zhang et al. |
| 6,469,227 B1 | 10/2002 | Cooke et al. |
| 6,475,494 B2 | 11/2002 | Kaiko et al. |
| 6,482,435 B1 | 11/2002 | Stratton et al. |
| 6,491,945 B1 | 12/2002 | Childers et al. |
| 6,572,871 B1 | 6/2003 | Church et al. |
| 6,572,885 B2 | 6/2003 | Oshlack et al. |
| 6,599,531 B2 | 7/2003 | Kushla et al. |
| 6,613,350 B1 | 9/2003 | Zhang et al. |
| 6,649,183 B2 | 11/2003 | Rubin et al. |
| 6,699,502 B1 | 3/2004 | Fanara et al. |
| 6,730,325 B2 | 5/2004 | Devane et al. |
| 6,733,783 B2 | 5/2004 | Oshlack et al. |
| 6,756,053 B2 | 6/2004 | Zhang et al. |
| 6,756,056 B2 | 6/2004 | Rubin |
| 6,780,426 B2 | 8/2004 | Zhang et al. |
| 6,827,946 B2 | 12/2004 | Hirsh |
| 6,855,332 B2 | 2/2005 | Gizurarson et al. |
| 6,902,742 B2 | 6/2005 | Devane et al. |
| 6,913,768 B2 | 7/2005 | Couch et al. |
| 6,923,988 B2 | 8/2005 | Patel et al. |
| 6,976,647 B2 | 12/2005 | Reed et al. |
| 7,029,698 B2 | 4/2006 | Waranis et al. |
| RE39,221 E | 8/2006 | Raffa et al. |
| 7,094,228 B2 | 8/2006 | Zhang et al. |
| 7,172,767 B2 | 2/2007 | Kaiko et al. |
| 7,201,920 B2 | 4/2007 | Kumar et al. |
| 7,214,385 B2 | 5/2007 | Gruber |
| 7,214,711 B2 | 5/2007 | Hochman |
| 7,332,183 B2 | 2/2008 | Plachetka et al. |
| 7,342,028 B2 | 3/2008 | Hagan et al. |
| 7,514,100 B2 | 4/2009 | Oshlack et al. |
| 7,585,493 B2 | 9/2009 | Hale et al. |
| 7,585,520 B2 | 9/2009 | Hirsh et al. |
| 7,666,337 B2 | 2/2010 | Yang et al. |
| 7,744,916 B2 | 6/2010 | Pauletti et al. |
| 7,794,750 B2 | 9/2010 | Naringrekar et al. |
| 7,863,296 B2 | 1/2011 | Weiner et al. |
| 7,943,174 B2 | 5/2011 | Oshlack et al. |
| 8,022,095 B2 | 9/2011 | Plachetka |
| 8,124,126 B2 | 2/2012 | Bosse et al. |
| 8,236,328 B2 | 8/2012 | Babcock et al. |
| 8,263,126 B2 | 9/2012 | Oury et al. |
| 8,268,791 B2 | 9/2012 | Maggio |
| 8,597,681 B2 | 12/2013 | Park et al. |
| 8,632,805 B2 | 1/2014 | Naringrekar et al. |
| 8,637,503 B2 | 1/2014 | Boland et al. |
| 8,653,066 B2 | 2/2014 | Bosse |
| 8,703,196 B2 | 4/2014 | Babcock et al. |
| 8,728,522 B2 | 5/2014 | Bosse et al. |
| 8,822,489 B2 | 9/2014 | Kumar et al. |
| 8,920,837 B2 | 12/2014 | Pilgaonkar et al. |
| 9,034,377 B2 | 5/2015 | Wright et al. |
| 9,044,435 B2 | 6/2015 | Wright et al. |

(56) References Cited

U.S. PATENT DOCUMENTS

| | | |
|---|---|---|
| 9,226,901 B2 | 1/2016 | Bosse et al. |
| 9,393,207 B2 | 7/2016 | Bosse |
| 9,399,022 B2 | 7/2016 | Bosse |
| 9,402,813 B2 | 8/2016 | Bosse |
| 2003/0008892 A1 | 1/2003 | Coe et al. |
| 2003/0068375 A1 | 4/2003 | Wright et al. |
| 2003/0092724 A1 | 5/2003 | Kao et al. |
| 2003/0133982 A1 | 7/2003 | Heimlich et al. |
| 2003/0181462 A1 | 9/2003 | Doods et al. |
| 2003/0225002 A1 | 12/2003 | Livingstone |
| 2004/0019080 A1 | 1/2004 | Sheftell et al. |
| 2004/0043071 A1 | 3/2004 | Pauletti et al. |
| 2004/0047907 A1 | 3/2004 | Oshlack et al. |
| 2004/0136913 A1 | 7/2004 | Dugger et al. |
| 2004/0136914 A1 | 7/2004 | Dugger et al. |
| 2004/0152713 A1 | 8/2004 | Petrie |
| 2004/0156859 A1 | 8/2004 | Ezrin et al. |
| 2004/0156903 A1 | 8/2004 | Abrams et al. |
| 2004/0167200 A1 | 8/2004 | Coe et al. |
| 2004/0170680 A1 | 9/2004 | Oshlack et al. |
| 2004/0185096 A1 | 9/2004 | Oshlack et al. |
| 2004/0195413 A1 | 10/2004 | Reed et al. |
| 2004/0213828 A1 | 10/2004 | Smith |
| 2004/0241159 A1 | 12/2004 | De |
| 2004/0248956 A1 | 12/2004 | Hagmann et al. |
| 2004/0266807 A1 | 12/2004 | Oshlack et al. |
| 2005/0074493 A1 | 4/2005 | Mehta et al. |
| 2005/0080012 A1 | 4/2005 | Mickle et al. |
| 2005/0084530 A1 | 4/2005 | Rao et al. |
| 2005/0106249 A1 | 5/2005 | Hwang et al. |
| 2005/0147710 A1 | 7/2005 | Teckoe et al. |
| 2005/0158382 A1 | 7/2005 | Cruz et al. |
| 2005/0163856 A1 | 7/2005 | Maloney et al. |
| 2005/0232986 A1 | 10/2005 | Brown et al. |
| 2005/0232987 A1 | 10/2005 | Srinivasan et al. |
| 2005/0232993 A1 | 10/2005 | Brown et al. |
| 2005/0266032 A1 | 12/2005 | Srinivasan et al. |
| 2005/0272810 A1 | 12/2005 | Davis et al. |
| 2005/0281875 A1 | 12/2005 | Srinivasan et al. |
| 2005/0282879 A1 | 12/2005 | Salehani |
| 2006/0009512 A1 | 1/2006 | Curwen et al. |
| 2006/0029664 A1 | 2/2006 | Srinivasan et al. |
| 2006/0057205 A1 | 3/2006 | Srinivasan et al. |
| 2006/0073189 A1 | 4/2006 | Pinney et al. |
| 2006/0110327 A1 | 5/2006 | Emigh et al. |
| 2006/0127479 A1 | 6/2006 | Kumaraperumal et al. |
| 2006/0134207 A1 | 6/2006 | Srinivasan et al. |
| 2006/0142273 A1 | 6/2006 | Rudolf et al. |
| 2006/0165604 A1 | 7/2006 | Dugger et al. |
| 2006/0177380 A1 | 8/2006 | Emigh et al. |
| 2006/0183693 A1 | 8/2006 | Doods et al. |
| 2006/0198790 A1 | 9/2006 | Dugger et al. |
| 2006/0204578 A1 | 9/2006 | Vergez et al. |
| 2006/0240105 A1 | 10/2006 | Devane et al. |
| 2007/0003622 A1 | 1/2007 | Srinivasan et al. |
| 2007/0059254 A1 | 3/2007 | Singh |
| 2007/0060500 A1 | 3/2007 | Mickle et al. |
| 2007/0099849 A1 | 5/2007 | Livingstone |
| 2007/0148097 A1 | 6/2007 | Finn et al. |
| 2007/0166336 A1 | 7/2007 | Delmarre et al. |
| 2007/0191462 A1 | 8/2007 | Hettiarachchi et al. |
| 2007/0231268 A1 | 10/2007 | Emigh et al. |
| 2007/0286875 A1 | 12/2007 | Dagar et al. |
| 2008/0044482 A1 | 2/2008 | Oshlack et al. |
| 2008/0057122 A1 | 3/2008 | Toney-Parker et al. |
| 2008/0074208 A1 | 3/2008 | Lee |
| 2008/0075781 A1 | 3/2008 | Oshlack et al. |
| 2008/0103134 A1 | 5/2008 | Rudolf et al. |
| 2008/0131517 A1 | 6/2008 | Fawzy et al. |
| 2008/0181941 A1 | 7/2008 | Oshlack et al. |
| 2008/0213343 A1 | 9/2008 | Obermeier et al. |
| 2008/0292699 A1 | 11/2008 | Brown et al. |
| 2009/0004281 A1 | 1/2009 | Nghiem et al. |
| 2009/0068269 A1 | 3/2009 | Oshlack et al. |
| 2009/0118170 A1 | 5/2009 | Dugger, III |
| 2009/0124554 A1 | 5/2009 | Dugger, III |
| 2009/0156581 A1 | 6/2009 | Dillon et al. |
| 2009/0162297 A1 | 6/2009 | Dugger, III et al. |
| 2009/0162298 A1 | 6/2009 | Dugger, III et al. |
| 2009/0163451 A1 | 6/2009 | Porreca et al. |
| 2009/0175939 A1 | 7/2009 | Bosse et al. |
| 2009/0232898 A1 | 9/2009 | Pettersson et al. |
| 2009/0311335 A1 | 12/2009 | Jenkins et al. |
| 2010/0008995 A1 | 1/2010 | Duncalf et al. |
| 2010/0112050 A1 | 5/2010 | Ryoo et al. |
| 2010/0143469 A1 | 6/2010 | Bosse |
| 2010/0144754 A1 | 6/2010 | Peltz et al. |
| 2010/0159007 A1 | 6/2010 | Staniforth |
| 2010/0160378 A1 | 6/2010 | Maggio |
| 2010/0196471 A1 | 8/2010 | Jain et al. |
| 2011/0066100 A1 | 3/2011 | Sebree et al. |
| 2011/0077272 A1 | 3/2011 | Main |
| 2011/0105441 A1 | 5/2011 | Zhang et al. |
| 2011/0118189 A1 | 5/2011 | Farr et al. |
| 2011/0262539 A1 | 10/2011 | Bosse et al. |
| 2012/0201888 A1 | 8/2012 | Bosse et al. |
| 2012/0202866 A1 | 8/2012 | Dugger, III et al. |
| 2014/0030322 A1 | 1/2014 | Bosse et al. |
| 2014/0073678 A1 | 3/2014 | Dadey et al. |
| 2014/0112981 A1 | 4/2014 | Oshlack et al. |
| 2014/0134248 A1 | 5/2014 | Bosse |
| 2014/0221416 A1 | 8/2014 | Guido et al. |
| 2014/0271896 A1 | 9/2014 | Abu et al. |
| 2014/0308349 A1 | 10/2014 | Bosse et al. |
| 2014/0323512 A1 | 10/2014 | McKenna |
| 2014/0357658 A1 | 12/2014 | Kaiko et al. |
| 2015/0030677 A1 | 1/2015 | Adjei et al. |
| 2015/0290211 A1 | 10/2015 | Bosse et al. |
| 2015/0297525 A1 | 10/2015 | Bosse et al. |
| 2015/0306040 A1 | 10/2015 | Bosse et al. |
| 2015/0320685 A1 | 11/2015 | Bosse et al. |
| 2015/0328210 A1 | 11/2015 | Bosse |
| 2015/0328212 A1 | 11/2015 | Bosse |
| 2015/0328213 A1 | 11/2015 | Bosse |
| 2016/0051474 A1 | 2/2016 | Bosse et al. |
| 2016/0106755 A1 | 4/2016 | Bosse et al. |

FOREIGN PATENT DOCUMENTS

| | | |
|---|---|---|
| FR | 2787713 A1 | 6/2000 |
| WO | WO-9718801 A1 | 5/1997 |
| WO | WO-9942095 A1 | 8/1999 |
| WO | WO-02080953 A2 | 10/2002 |
| WO | WO-02080953 A3 | 12/2002 |
| WO | WO-2006022996 A2 | 3/2006 |
| WO | WO-2006103418 A1 | 10/2006 |
| WO | WO-2006022996 A3 | 12/2006 |
| WO | WO-2007035573 A2 | 3/2007 |
| WO | WO-2007035573 A3 | 6/2007 |
| WO | WO-2007130507 A2 | 11/2007 |
| WO | WO-2008027350 A2 | 3/2008 |
| WO | WO-2008027350 A3 | 5/2008 |
| WO | WO-2008070268 A2 | 6/2008 |
| WO | WO-2008074419 A1 | 6/2008 |
| WO | WO-2008070268 A3 | 11/2008 |
| WO | WO-2009089494 A2 | 7/2009 |
| WO | WO-2009089494 A3 | 1/2010 |
| WO | WO-2010062688 A2 | 6/2010 |
| WO | WO-2011006012 A1 | 1/2011 |
| WO | WO-2010062688 A3 | 5/2012 |
| WO | WO-2014043346 A2 | 3/2014 |

OTHER PUBLICATIONS

Adolph, et al. Promethazine inhibits NMDA-induced currents—new pharmacological aspects of an old drug. Neuropharmacology. Aug. 2012;63(2):280-91. doi: 10.1016/j.neuropharm.2012.03.006. Epub Apr. 7, 2012.

Alexander, et al. Comparison of ondansetron and droperidol in reducing postoperative nausea and vomiting associated with patient-controlled analgesia. Anaesthesia. Dec. 1995;50(12):1086-8.

(56) References Cited

OTHER PUBLICATIONS

Amdipharm Plc. Opioid-induced nausea and vomiting. Web Site by Nexus Internet Solutions Ltd. Apr. 2004.
Amo, et al. Subchronic and chronic effects of feeding of large amounts of acetaminophen in B6C3F1 mice. Jap J Hyg. 40:567-574, 1985.
Anderson. Paracetamol (Acetaminophen): mechanisms of action. Paediatr Anaesth. Oct. 2008; 18(10):915-21. doi: 10.1111/j.1460-9592.2008.02764.x.
Anesthetic, Analgesic, Rheumatic Drugs Division, Pre-IND Meeting with Charleston Laboratories, Inc. Nov. 8, 2007, Silver Springs, MD.
Aparasu, et al. Opioid- induced emesis among hospitalized nonsurgical patients: effect on pain and quality of life. J Pain Symptom Manage. Oct. 1999;18(4):280- 8.
Apfel, et al. A factorial trial of six interventions for the prevention of postoperative nausea and vomiting. N Engl J Med. Jun. 10, 2004;350(24):2441-51.
Apfel, et al. A risk score to predict the probability of postoperative vomiting in adults. Acta Anaesthesiol Scand. May 1998;42(5):495-501.
Apfel, et al. A simplified risk score for predicting postoperative nausea and vomiting: conclusions from cross-validations between two centers. Anesthesiology. Sep. 1999;91(3):693-700.
Apfel, et al. The discriminating power of a risk score for postoperative vomiting in adults undergoing various types of surgery. Acta Anaesthesiol Scand. May 1998;42(5):502-9.
Apfelbaum, et al. Reliability and validity of the perioperative opioid-related symptom distress scale. Anesth Analg. Sep. 2004;99(3):699-709, table of contents.
Armstrong, et al. Pharmacokinetic drug interactions of morphine, codeine, and their derivatives: Theory and clinical reality, Part II. Psychosomatics. 44(6):515-20, 2003.
Aronson, et al. Aronson CE, Hanno ERS. Effect of promethazine on the isolated perfused rat heart. Gen Pharmacol. 10:389-395, 1979.
Atkinson, et al. Hierarchical construct validity of the treatment satisfaction questionnaire for medication (TSQM version II) among outpatient pharmacy consumers. Value Health. Nov.-Dec. 2005;8 Suppl 1:S9-S24.
Balster, et al. Guidelines and methodological reviews concerning drug abuse liability assessment. Drug Alcohol Depend. Jun. 5, 2003;70(3 Suppl):S13-40.
Barkin. Acetaminophen, aspirin, or Ibuprofen in combination analgesic products. Am J Ther. Nov.-Dec. 2001;8(6):433-42.
Becker, et al. Drug-induced QT interval prolongation in cancer patients. Oncol Rev., 2010; 4(4):223-232.
Benning, et al. Validation of the in vivo CD1 mouse splenocyte micronucleus test. Mutagenesis. May 1994;9(3):199-204.
Bergman, et al. Series: current issues in mutagenesis and carcinogenesis, No. 65. The genotoxicity and carcinogenicity of paracetamol: a regulatory (re)view.Mutat Res. Feb. 1, 1996;349(2):263-88.
Bessems, et al. Paracetamol (acetaminophen)-induced toxicity: molecular and biochemical mechanisms, analogues and protective approaches. Crit Rev Toxicol. Jan. 2001;31(1):55-138.
Betancourt, et al. Efficacy of ibuprofen-hydrocodone for the treatment of postoperative pain after periodontal surgery. J Periodontol. Jun. 2004;75(6):872-6.
Blecharz-Klin, et al. Developmental exposure to paracetamol causes biochemical alterations in medulla oblongata. Environ Toxicol Pharmacol. Sep. 2015;40(2):369-74. doi: 10.1016/j.etap.2015.07.001. Epub Jul. 4, 2015.
Bouillon, T. et al. A model of the ventilatory depressant potency of remifentanil in the non-steady state. Anesthesiology 2003;99:779-87.
Bovbjerg, et al. An experimental analysis of classically conditioned nausea during cancer chemotherapy. Psychosom Med. Nov.-Dec. 1992;54(6):623-37.
Braude, et al. Ondansetron versus promethazine to treat acute undifferentiated nausea in the emergency department: a randomized, double-blind, noninferiority trial. Acad Emerg Med. Mar. 2008;15(3):209-15. doi: 10.1111/j.1553-2712.2008.00060.x.
Bruera, et al. The Edmonton Symptom Assessment System (ESAS): a simple method for the assessment of palliative care patients. J Palliat Care. 1991 Summer;7(2):6-9.
Burke, et al. Evaluation of pyrazole and ethanol induced S9 fraction in bacterial mutagenicity testing. Mutagenesis. Jan. 1994;9(1):23-9.
Chang DJ, et al. Comparison of rofecoxib and a multidose oxycodone/ acetaminophen regimen for the treatment of acute pain following oral surgery: a randomized controlled trial. Curr. Med. Res. Opin. 2004; 20: 939-49.
Chang, et al. Validation of the Edmonton Symptom Assessment Scale. Cancer. May 1, 2000;88(9):2164-71.
Chapin, et al. Reproductive assessment by continuous breeding: evolving study design and summaries of ninety studies. Environ Health Perspect. Feb. 1997;105 Suppl 1:199-205.
Charleston Laboratories' Investigational New Drug Application, pp. 93-94, filed with the U.S. Food and Drug Administration on Sep. 5, 2008. Charleston Laboratories is the assignee of the present application.
Chen, et al. Design and analysis for drug abuse potential studies: issues and strategies for implementing a crossover design. DIA J. 2007; 41:481-489.
Cherny. Opioid analgesics: comparative features and prescribing guidelines. Drugs. May 1996;51(5):713-37.
Chia, et al. The effect of promethazine on postoperative pain: a comparison of preoperative, postoperative, and placebo administration in patients following total abdominal hysterectomy. Acta Anaesthesiol Scand. May 2004;48(5):625-30.
Chow, et al. Chapter 4: Statistical Methods for Average Bioavailability. Design and Analysis of Bioavailability and Bioequivalence Studies. 2nd Edition. Published by Marcel Dekker, 2000. p. 98. DCN 3007688.
Chow, et al. Chapter 6: Transformation and analysis of individual subject ratios. Design and Analysis of Bioavailability and Bioequivalence Studies. 2nd Edition. Published by Marcel Dekker, 2000. p. 161.
Cisternas, et al. Trends in medical care expenditures of US adults with arthritis and other rheumatic conditions 1997 to 2005. J Rheumatol. Nov. 2009;36(11):2531-8. doi: 10.3899/jrheum.081068. Epub Oct. 1, 2009.
Cleren, et al. Promethazine protects against 1-methyl-4-phenyl-1,2,3,6-tetrahydropyridine neurotoxicity. Neurobiol Dis. Dec. 2005;20(3):701-8. Epub Aug. 26, 2005.
Cliet, et al. In vivo micronucleus test using mouse hepatocytes. Mutat Res. Dec. 1989;216(6):321-6.
Colagiuri, et al. Patient expectancy and post-chemotherapy nausea: a meta-analysis. Ann Behav Med. Aug. 2010;40(1):3-14. doi: 10.1007/s12160-010-9186-4.
Colloca, et al. Placebo and Nocebo. In the: Textbook of Clinical Pain Management 2E, edited by Rice A, Howard R, Justins D, Miaskowski C, Newton-John T. Hodder Arnold, Practice and Procedures. London NW1 3BH, 2008, 499-513.
Colloca, et al. The role of learning in nocebo and placebo effects. Pain. May 2008;136(1-2):211-8. doi: 10.1016/j.pain.2008.02.006. Epub Mar. 26, 2008.
Cone, et al. Comparative metabolism of hydrocodone in man, rat, guinea pig, rabbit, and dog. Drug Metab Dispos. Jul.-Aug. 1978;6(4):488-93.
Cone, et al. Prescription opioids. II. Metabolism and excretion patterns of hydrocodone in urine following controlled single-dose administration. J Anal Toxicol. Oct. 2013;37(8):486-94. doi: 10.1093/jat/bkt066. Epub Aug. 14, 2013.
Connolly, et al. Alpha 4-2 beta 2 and other nicotinic acetylcholine receptor subtypes as targets of psychoactive and addictive drugs. Br J Pharmacol. Mar. 1992;105(3):657-66.
Cooper, et al. A model to evaluate mild analgesics in oral surgery outpatients. Clin Pharmacol Ther. Aug. 1976;20(2):241-50.
Cooper, et al. Ibuprofen and acetaminophen in the relief of acute pain: a randomized, double-blind, placebo-controlled study. J Clin Pharmacol. Nov. 1989;29(11):1026-30.
Da Silva, et al. Acute brain damage induced by acetaminophen in mice: effect of diphenyl diselenide on oxidative stress and

(56) References Cited

OTHER PUBLICATIONS mitochondrial dysfunction. Neurotox Res. Apr. 2012;21(3):334-44. doi: 10.1007/s12640-011-9288-1. Epub Nov. 12, 2011.
Dagenais, et al. Systematic review of the prevalence of radiographic primary hip osteoarthritis. Clin Orthop Relat Res. Mar. 2009;467(3):623-37. doi: 10.1007/s11999-008-0625-5. Epub Nov. 27, 2008.
Daniels, et al. The analgesic efficacy of valdecoxib vs. oxycodone/acetaminophen after oral surgery. J Am Dent Assoc. May 2002;133(5):611-21; quiz 625.
Daniels S., et al A randomized, double-blind, placebo-controlled phase 3 study of the relative efficacy and tolerability of tapentadol IR and oxycodone IR for acute pain Curr Med Res Opin. 2009; 25: 1551-61.
Darwish, et al. Dose proportionality of a hydrocodone extended-release tablet formulated with abuse-deterrence technology. Clin Drug Investig. May 2015;35(5):291-7. doi: 10.1007/s40261-015-0280-z.
Darwish, et al. Single- and multiple-dose pharmacokinetics of a hydrocodone bitartrate extended-release tablet formulated with abuse-deterrence technology in healthy, naltrexone-blocked volunteers. Clin Ther. Feb. 1, 2015;37(2):390-401. doi: 10.1016/j.clinthera.2014.11.014. Epub Dec. 24, 2014.
Davis, et al. Species differences in hepatic glutathione depletion, covalent binding and hepatic necrosis after acetaminophen. Life Sci. Jun. 1, 1974;14(11):2099-109.
Davis. Hydrocodone. Opioids for cancer pain. Oxford UK: Oxford University Press. 2005. pp. 59-68. ISBN 0-19-852943-0.
DeSchepper, H.U. et al. Opioids and the gut: pharmacology and current clinical experience. Neurogastroenterol Motil. Aug. 2004;16(4):383-94.
Desjardins, et al. A randomized controlled study comparing rofecoxib, diclofenac sodium, and placebo in post-bunionectomy pain. Curr Med Res Opin. Oct. 2004;20(10):1523-37.
Desjardins, et al. A single preoperative oral dose of valdecoxib, a new cyclooxygenase-2 specific inhibitor, relieves post-oral surgery or bunionectomy pain. Anesthesiology. Sep. 2002;97(3):565-73.
Desjardins, et al. Analgesic efficacy of preoperative parecoxib sodium in an orthopedic pain model. J Am Podiatr Med Assoc. May-Jun. 2004;94(3):305-14.
Devalia, et al. Dissociation of cell death from covalent binding of paracetamol by flavones in a hepatocyte system. Biochem Pharmacol. Dec. 1, 1982;31(23):3745-9.
Devarakonda, et al. Comparison of single-dose and multiple-dose pharmacokinetics between two formulations of hydrocodone bitartrate/acetaminophen: immediate-release versus biphasic immediate-release/extended release. J Pain Res. Sep. 9, 2015;8:607-18. doi: 10.2147/JPR.S79578. eCollection 2015.
Dipasquale, et al. Post nidatory action of various compounds representing several pharmacological classes. Res Commun Chem Pathol Pharmacol. Apr. 1974;7(4):701-14.
Dunn, et al. Genotoxicity of analgesic compounds assessed by an in vitro micronucleus assay. Mutat Res. Nov. 1987;189(3):299-306.
Farrar, et al. Clinically important changes in acute pain outcome measures: a validation study. J Pain Symptom Manage. May 2003;25(5):406-11.
FDA Draft Guidance for Industry. Assessment of abuse potential of drugs, 2010.
FDA Monograph for Phenergan, Revised Jul. 2005; http://www.drugs.com/pro/phenergan.html; accessed Feb. 19, 2014.
FDA Monograph for Vicoprofen; Revised Oct. 2009; http://www.drugs.com/pro/vicoprofen.html; accessed Feb. 19, 2014.
Fendrick, et al. Self-selection and use patterns of over-the-counter omeprazole for frequent heartburn. Clin Gastroenterol Hepatol. Jan. 2004;2(1):17-21.
Ford. Soft-tissue bunionectomy in podiatric surgery. Clin Podiatr Med Surg. Jan. 1991;8(1):63-70.
Foster, et al. Complicated pain management in a CYP450 2D6 poor metabolizer. Pain Pract. Dec. 2007;7(4):352-6.
Fricke, et al. A double-blind, single-dose comparison of the analgesic efficacy of tramadol/acetaminophen combination tablets, hydrocodone/acetaminophen combination tablets, and placebo after oral surgery. Clin Ther. Jun. 2002;24(6):953-68.
Gan, et al. A consensus panel identification of risk factors for PONV. Anesth. 2002; 96:A19.
Gan, et al. Consensus guidelines for managing postoperative nausea and vomiting. Anesth Analg. Jul. 2003;97(1):62-71, table of contents.
Gan, et al. Risk factors for postoperative nausea and vomiting. Anesth Analg. Jun. 2006;102(6):1884-98.
Gordon, et al. Activation of P-glycoprotein efflux transport ameliorates opioid CNS effects without diminishing analgesia. Drug Disc Today: Therap Strat 2009; 6:97-103.
Gotzsche. Reporting of outcomes in arthritis trials measured on ordinal and interval scales is inadequate in relation to meta-analysis. Ann Rheum Dis. Apr. 2001;60(4):349-52.
Gotzsche. Sensitivity of effect variables in rheumatoid arthritis: a meta-analysis of 130 placebo controlled NSAID trials. J Clin Epidemiol. 1990;43(12):1313-8.
Gregorian, Jr. et al., Importance of Side Effects in Opioid Treatment: A Trade-Off Analysis With Patients and Physicians. J Pain. 2010; 11: 1095-108.
Griffiths, et al. Principles of initial experimental drug abuse liability assessment in humans. Drug Alcohol Depend. Jun. 5, 2003;70(3 Suppl):S41-54.
Guidance for Industry: Bioavailability and Bioequivalence Studies for Orally Administered Drug Products—General Considerations U.S. Department of Health and Human Services Food and Drug Administration Center for Drug Evaluation and Research (CDER) Mar. 2003.
Guidance for Industry: Statistical Approaches to Establishing Bioequivalence U.S. Department of Health and Human Services Food and Drug Administration Center for Drug Evaluation and Research (CDER) Jan. 2001.
Hardy, et al. A double-blind, randomised, parallel group, multinational, multicentre study comparing a single dose of ondansetron 24 mg p.o. with placebo and metoclopramide 10 mg t.d.s. p.o. in the treatment of opioid-induced nausea and emesis in cancer patients. Support Care Cancer. Apr. 2002;10(3):231-6.
Hays, et al. The RAND 36-Item Health Survey 1.0. Health Econ. Oct. 1993;2(3):217-27.
Hersh, E. et al. Opioid-Induced Nausea and Vomiting (OINV) in patients without immediate post-op nausea/vomiting. The Journal of Pain, 16(4); S80 (Apr. 2015).
Hersh, E. et al. What is the likelihood of opioid-induced nausea and vomiting (OINV) in patients with a history that is only suggestive of OINV? The Journal of Pain, vol. 16(4); S16 (Apr. 2015).
Hersh, E. et al. Efficacy of CL-108 compared to hydrocodone 7.5 mg/acetaminophen 325 mg in preventing vomiting and the use of anti-emetics, Opioid-Induced Nausea and Vomiting (OINV). The Journal of Pain, vol. 1(4): S82 (Apr. 2016).
Hersh, et al. Ibuprofen liquigel for oral surgery pain. Clin Ther. Nov. 2000;22(11):1306-18.
Holzer, P. Treatment of opioid-induced gut dysfunction. Expert Opin Investig Drugs 2007;16:181-194.
Hysingla Label. Purdue Pharma L. P. Nov. 2014.
Imitrex prescribing information. Dec. 2004. http://www.fda.gov/ohrms/dockets/ac/05/briefing/2005-4180b_09_05_imitrex%20label%20tablet%2012-04%20sponsor.pdf.
International preliminary report on patentability dated Jul. 22, 2010 for PCT Application No. PCT/US09/30662.
International search report dated May 22, 2009 for Application No. US2009/30662.
International search report dated Sep. 1, 2010 for PCT Application No. PCT/US2010/41433.
International search report dated Sep. 23, 2008 for Application No. PCT/US2007/80831.
Interview summary dated Sep. 18, 2015 for U.S. Appl. No. 14/789,888.
Interview summary dated Oct. 2, 2015 for U.S. Appl. No. 14/789,888.

(56) References Cited

OTHER PUBLICATIONS

Interview summary dated Oct. 20, 2015 for U.S. Appl. No. 14/036,946.
Interview summary dated Nov. 23, 2015 for U.S. Appl. No. 14/748,614.
Interview summary dated Nov. 23, 2015 for U.S. Appl. No. 14/748,617.
Interview summary dated Nov. 24, 2015 for U.S. Appl. No. 14/244,455.
Interview summary dated Nov. 24, 2015 for U.S. Appl. No. 14/748,605.
Interview summary dated Nov. 25, 2015 for U.S. Appl. No. 14/789,883.
Jang, J.O. et al. Pharmacokinetic Study of Promethazine in Korean Healthy Subjects Using a Validated HPLC Method. J Appl Pharm. 2005;13:118-122.
Kalso E., et al. Opioids in chronic non-cancer pain: systematic review of efficacy and safety Pain. 2004; 112: 372-80.
Katz N., et al. The impact of opioids on the endocrine system. Clin J Pain 2009; 25(2): 170-175.
Korn, et al. Comparison of rofecoxib and oxycodone plus acetaminophen in the treatment of acute pain: a randomized, double-blind, placebo-controlled study in patients with moderate to severe postoperative pain in the third molar extraction model. Clin Ther. May 2004;26(5):769-78.
Kovac, A. Prophylaxis of postoperative nausea and vomiting: controversies in the use of serotonin 5-hydroxytryptamine subtype 3 receptor antagonists. J Clin Anesth. Jun. 2006;18(4):304-18.
Lalley, P.M. Mu-opioid receptor agonist effects on medullary respiratory neurons in the cat: evidence for involvement in certain types of ventilatory disturbances. Am J Physiol Regul Integr Comp Physiol. Dec. 2003;285(6):R1287-304.
Lasagna. A plea for the 'Naturalistic' study of medicines. Eur J Clin Pharmacol. 1974;7(3):153-4.
Lasagna. The clinical measurement of pain. Ann N Y Acad Sci. Mar. 30, 1960;86:28-37.
Lasagna. The controlled clinical trial: theory and practice. J Chronic Dis. Apr. 1955;1(4):353-67.
Litkowski, et al. Analgesic efficacy and tolerability of oxycodone 5 mg/ibuprofen 400 mg compared with those of oxycodone 5 mg/acetaminophen 325 mg and hydrocodone 7.5 mg/acetaminophen 500 mg in patients with moderate to severe postoperative pain: a randomized, double-blind, placebo-controlled, single-dose, parallel-group study in a dental pain model. Clin Ther. Apr. 2005;27(4):418-29.
Malmstrom, et al. Comparison of rofecoxib and celecoxib, two cyclooxygenase-2 inhibitors, in postoperative dental pain: a randomized, placebo- and active-comparator-controlled clinical trial. Clin Ther. Oct. 1999;21(10):1653-63.
Mayo Clinic Website. Cough and Cold Combination (Oral Route). Available at www.mayoclinic.com/health/drug-infomation/DR602361. Accessed Oct. 2, 2007.
Meert, et al. A preclinical comparison between different opioids: antinociceptive versus adverse effects. Pharmacol Biochem Behav. Feb. 2005;80(2):309-26. Epub Jan. 7, 2005.
Mellen, N.M., et al. Opioid-induced quantal slowing reveals dual networks for respiratory rhythm generation. Neuron. Mar. 6, 2003;37(5):821-6.
Melzack, et al. On the language of pain. Anesthesiology. Jan. 1971;34(1):50-9.
Moore, et al. Prevalence of opioid adverse events in chronic non-malignant pain: systematic review of randomised trials of oral opioids. Arthritis Res Ther. 2005;7(5):R1046-51. Epub Jun. 28, 2005.
Moser, et al. No more than necessary: Safety and efficacy of low-dose promethazine. Annals of Pharmacotherapy. 2006; 40:45-48.
Murphy, et al. Comorbidities are very common among people with arthritis. Poster 43. 20th national Conference on Chronic Disease Prevention and Control. Washing, DC, Centers for Disease Control and Prevention. 2009.
Musclow, Shirley L. et al., Long-acting morphine following hip or knee replacement: A randomized, double-blind, placebo-controlled trial. Pain Res Manag. 2012; 17: 83-8.
Navratil, H. Contribution to the study of dihydrone pectinate. Its administration in the course of anesthesia 100 observations. Rev. MRO. Toulouse. 1966, II. pp. 249-254 (in French with English translation).
Neogi, et al. Composite versus individual measures of disease activity in rheumatoid arthritis. J Rheumatol. Feb. 2008;35(2):185-7.
Neogi, et al. Relative responsiveness of physician/assessor-derived and patient-derived core set measures in rheumatoid arthritis trials. J Rheumatol. May 2008;35(5):757-62. Epub Apr. 15, 2008.
Notice of allowance dated Jan. 28, 2014 for U.S. Appl. No. 12/967,423.
Notice of allowance dated Feb. 8, 2016 for U.S. Appl. No. 14/789,888.
Notice of allowance dated Feb. 18, 2016 for U.S. Appl. No. 14/244,455.
Notice of allowance dated Feb. 18, 2016 for U.S. Appl. No. 14/748,609.
Notice of allowance dated Feb. 19, 2016 for U.S. Appl. No. 14/748,605.
Notice of allowance dated Feb. 19, 2016 for U.S. Appl. No. 14/748,614.
Notice of allowance dated Feb. 24, 2016 for U.S. Appl. No. 14/748,621.
Notice of allowance dated Sep. 24, 2015 for U.S. Appl. No. 14/036,946.
Notice of allowance dated Oct. 2, 2015 for U.S. Appl. No. 14/789,888.
Notice of allowance dated Oct. 7, 2013 for U.S. Appl. No. 12/444,521.
Notice of allowance dated Oct. 11, 2011 for U.S. Appl. No. 12/351,704.
Notice of allowance dated Nov. 3, 2015 for U.S. Appl. No. 14/036,946.
Notice of allowance dated Nov. 4, 2015 for U.S. Appl. No. 14/789,888.
Notice of Allowance Mailed Jun. 3, 2016 in U.S. Appl. No. 14/748,609.
Notice of Allowance Mailed Jun. 7, 2016 in U.S. Appl. No. 14/748,605.
Notice of Allowance Mailed Jun. 8, 2016 in U.S. Appl. No. 14/244,455.
O'Connor, et al. Framing effects on expectations, decisions, and side effects experienced: the case of influenza immunization. J Clin Epidemiol. Nov. 1996;49(11):1271-6.
Office action dated Feb. 29, 2012 for U.S. Appl. No. 12/967,423.
Office action dated Feb. 7, 2013 for U.S. Appl. No. 12/444,521.
Office action dated Mar. 27, 2015 for U.S. Appl. No. 14/036,946.
Office action dated Jun. 29, 2012 for U.S. Appl. No. 12/444,521.
Office action dated Jul. 17, 2014 for U.S. Appl. No. 13/347,552.
Office action dated Aug. 14, 2015 for U.S. Appl. No. 14/789,883.
Office action dated Aug. 14, 2015 for U.S. Appl. No. 14/789,886.
Office action dated Sep. 6, 2012 for U.S. Appl. No. 12/967,423.
Office action dated Sep. 8, 2015 for U.S. Appl. No. 14/748,605.
Office action dated Sep. 8, 2015 for U.S. Appl. No. 14/748,609.
Office action dated Sep. 10, 2015 for U.S. Appl. No. 14/748,617.
Office action dated Sep. 17, 2015 for U.S. Appl. No. 14/244,455.
Office action dated Sep. 17, 2015 for U.S. Appl. No. 14/748,614.
Office action dated Sep. 18, 2015 for U.S. Appl. No. 14/789,888.
Office action dated Oct. 2, 2015 for U.S. Appl. No. 14/748,613.
Office action dated Oct. 2, 2015 for U.S. Appl. No. 14/748,621.
Office action dated Oct. 8, 2014 for U.S. Appl. No. 14/036,946.
Office action dated Sep. 20, 2010 for U.S. Appl. No. 12/351,704.
Oldfield, et al. Oxycodone/Ibuprofen combination tablet: a review of its use in the management of acute pain. Drugs. 2005;65(16):2337-54.

(56) References Cited

OTHER PUBLICATIONS

Package Insert. Duragesic. Janssen Pharmaceutica Products. 2003.
Package Insert. Oxycontin. Purdue Pharma L.P. Sep. 7, 2007.
Palangio, et al. Combination hydrocodone and ibuprofen versus combination oxycodone and acetaminophen in the treatment of moderate or severe acute low back pain. Clin Ther. Jan. 2002;24(1):87-99.
Palangio, M., et al. Dose-response effect of combination hydrocodone with ibuprofen in patients with moderate to severe postoperative pain. Clin Ther. Aug. 2000; 22(8):990-1002.
Paoloni, et al. Low incidence of nausea and vomiting with intravenous opiate analgesia in the ED. Am J Emerg Med. Nov. 2002;20(7):604-8.
Park, Yong-Beom et al., A randomized study to compare the efifficacy and safety of extended-release and immediate-release tramadol HCl/acetaminophen in patients with acute pain following total knee replacement. Curr Med Res Opin. 2015; 31: 75-84.
Peloso, P.M., et al. Protocol TRP-CAN-1 Study Group. Analgesic efficacy and safety of tramadol/ acetaminophen combination tablets (Ultracet) in treatment of chronic low back pain: a multicenter, outpatient, randomized, double blind, placebo controlled trial. J Rheumatol. Dec. 2004;31(12):2454-63.
Petersson, et al. Radiographic osteoarthritis of the knee classified by the Ahlbäck and Kellgren & Lawrence systems for the tibiofemoral joint in people aged 35-54 years with chronic knee pain. Ann Rheum Dis. Aug. 1997;56(8):493-6.
Porreca, et al. Nausea and vomiting side effects with opioid analgesics during treatment of chronic pain: mechanisms, implications, and management options. Pain Med. May-Jun. 2009;10(4):654-62. doi: 10.1111/j.1526-4637.2009.00583.x. Epub Mar. 19, 2009.
Promethazine HCl and Hydrocodone Bitartrate Syrup. WraSer Pharmaceuticals, Madison, MS. Jan. 2007.
Promethazine Hydrochloride. Orange book: approved drug products with therapeutic equivalence evaluations. FDA. www.accessdata.fda.gov. Updated Aug. 21, 2014.
Prosolve Data Sheet [online] retrieved on Feb. 27, 2012 from: http://www.jrspharma.de/Pharma/wEnglisch/produktinfo/prosolv_smcc/prosolv_smcc_grades.shtml; 2 pages.
Quessy. Two-stage enriched enrolment pain trials: a brief review of designs and opportunities for broader application. Pain. Jan. 2010;148(1):8-13. doi: 10.1016/j.pain.2009.10.029. Epub Nov. 25, 2009.
Ragg, et al. Comparison of the efficacy of paracetamol versus paracetamol, codeine and promethazine (Painstop) for premedication and analgesia for myringotomy in children. Anaesth Intensive Care. Feb. 1997;25(1):29-32.
Registry of Toxic Effects of Chemical Substances (RTECS) Database: Hydrocodone. MDL Information Systems. Updated Dec. 2010.
Reidenberg, et al. Adverse nondrug reactions. N Engl J Med. Sep. 26, 1968;279(13):678-9.
Richardson, S. et al. Opioid-Induced Nausea and Vomiting (OINV) in Post-Operative Patients: A Comparison of CL-108 to Hydrocodone7.5 mg/Acetaminophen 325 mg. The Journal of Pain, 17(4); Supplement, p. S83 (Apr. 2016).
Richmond, B. S. Pharmacy & Therapeutics Committees. Antiemetic Prophylaxis and Treatment of Postoperative and Opioid-Induced Nausea and Vomiting. Jul. 2007.
Rodriguez, et al. Codeine/acetaminophen and hydrocodone/acetaminophen combination tablets for the management of chronic cancer pain in adults: a 23-day, prospective, double-blind, randomized, parallel-group study. Clin Ther. Apr. 2007;29(4):581-7.
Rodriguez, et al. Incidence of weak opioids adverse events in the management of cancer pain: a double-blind comparative trial. J Palliat Med. Feb. 2007;10(1):56-60.
Roxycodone (Oxycodone Hydrochloride Tablets USP) label, Revised Aug. 2008.
Rush, et al. Chemically induced nephrotoxicity: role of metabolic activation. Crit Rev Toxicol. 1984;13(2):99-160.
Sadock, et al. Kaplan & Sadock's pocket handbook of psychiatric drug treatment 4th Ed, illustrated. Lippincott Williams & Wilkins 2005; Chapter 11.
Sanofi- Aventis. Phenergan® Tablets/Elixir Data Sheet. 2007.
Sasaki, et al. Cytogenetic effects of 60 chemicals on cultured human and Chinese hamster cells. Kromosomo. 1980; 20:574-584.
Savides, et al. Acetaminophen and its toxicity. J Appl Toxicol. Apr. 1983;3(2):96-111.
Savides, et al. The toxicity and biotransformation of single doses of acetaminophen in dogs and cats. Toxicol Appl Pharmacol. Jun. 15, 1984;74(1):26-34.
Sawaddiruk, et al. Comparison of efficacy and effectiveness between ULTRACET and tramadol/acetaminophen in acute post-operative pain after upper extremity surgery. J Med Assoc Thai. Jul. 2010;93(7):812-7.
Schachtel. Analgesic agents. In: Yaffe SJ and Aranda JV, eds. Pediatric Pharmacology. Therapeutic Principles in Practice. Philadelphia: WB Saunders,1992:406-412.
Schachtel, B.Demonstration of the safety and efficacy of CL-108 for moderate-to-severe pain with reduction of opioid-induced nausea and vomiting. The Journal of Pain, 15(4); S81 (Apr. 2014).
Schachtel, et al. A randomized, double-blind, placebo-controlled model demonstrating the topical effect of benzydamine in children with sore throat. Clin Pharmacol Ther 1996; 59:146.
Schachtel, et al. A placebo-controlled model for assaying systemic analgesics in children. Clin Pharmacol Ther. May 1993;53(5):593-601.
Schachtel, et al. Actual-use study of omeprazole magnesium. Clin Pharmacol Ther. 2000; 67:149.
Schachtel, et al. Assaying analgesic response in children: a double-blind, placebo-controlled model involving earache. Pediatr Res 1991; 29:124A.
Schachtel, et al. Caffeine as an analgesic adjuvant double-blind study comparing aspirin 800mg with caffeine 64mg to aspirin 800 mg and placebo in patients with sore throat. Arch Int Med. 1991; 151:733-8.
Schachtel, et al. Change in design of actual-use study assists in interpretation of study results. Abstract P11. Clin Pharmacol Ther. 2001; 69:P11.
Schachtel, et al. Demonstration of the safety and efficacy of CL-108 for moderate-to-severe pain with reduction of opioid-induced nausea and vomiting. Abstract No. 420, Journal of Pain, Apr. 2014, vol. 15, No. 4, Supp. SUPPL. 1, p. S81, 33rd Annual Scientific Meeting of the American Pain Society, Apr. 30 2014-May 3, 2014.
Schachtel, et al. Gastric side effects of aspirin compared to acetaminophen and placebo in the treatment of headache. Acta Pharmacol Toxicol. 1986; 59:170.
Schachtel, et al. Pain relief in children. A placebo-controlled model. Clin Pharmacol Ther 1991; 49:154.
Schachtel, et al. Patients' criteria for meaningful relief to determine onset of action. Clin Pharmacol Ther. 2005; 77:P51.
Schachtel, et al. Rating scales for analgesics in sore throat. Clin Pharmacol Ther. Aug. 1984;36(2):151-6.
Schachtel, et al. Sore throat pain model for the evaluation of analgesics in children. J Pain and Symptom Manag 1991; 6:159.
Schachtel, et al. The Lasagna Pain Scale (LPS). Clin Pharmacol Ther. 2005; 77:93.
Schachtel. How actual-use studies augment product development. Abstract A95. AAPS—Pharmaceutical Sciences Section, American Association of Pharmaceutical Sciences (AAPS). 1 (Suppl):A95. 1999.
Schachtel. Sore throat pain. In: Max MB, Portnoy RK, and Laska EM, eds. The Design of Analgesic Clinical Trials. (Advances in pain research and therapy; vol. 18) New York: Raven Press, 1991:393-406.
Schwinghammer, et al. Comparison of the bioavailability of oral, rectal and intramuscular promethazine. Biopharm Drug Dispos. Apr.-Jun. 1984;5(2):185-94.
Seeff, et al. Acetaminophen hepatotoxicity in alcoholics. Ann Intern Med. 1986;104:399-404.
Serratoni, et al. Promethazine protection in carbon tetrachloride liver injury. An electron microscopic study. Arch Pathol. Jan. 1969;87(1):46-51.

(56) References Cited

OTHER PUBLICATIONS

Severin, et al. Induction of chromosome aberrations in vivo in bone-marrow cells of mice by paracetamol. Rom J Morphol Embryol. Jul.-Dec. 1995;41(3-4):117-20.
Shafer, et al. The Roche friabilator. J Am Pharm Assoc. Feb. 1956;45(2 Part 1):114-6.
Shang, et al. Effect of promethazine on electrophysiological action of guinea pig hearts. Chin J Pharmacol Toxicol; 28(5): 691-697.
Sharma, a, & Hamelin, B. a. (2003). Classic histamine H1 receptor antagonists: a critical review of their metabolic and pharmacokinetic fate from a bird's eye view. Current Drug Metabolism, 4(2), 105-129. doi:10.2174/1389200033489523.
Shibata, et al. Modification by analgesics of lesion development in the urinary tract and various other organs of rats pretreated with dihydroxy-di-N-propylnitrosamine and uracil. Jpn J Cancer Res. Feb. 1995;86(2):160-7.
Shuey, et al. Oxymorphone hydrochloride, a potent analgesic, is not carcinogenic in rats or mice. Toxicol Sci. Mar. 2007;96(1):162-73. Epub Nov. 30, 2006.
Siegers, et al. Relationships between hepatotoxicity and pharmacokinetics of paracetamol in rats and mice. Pharmacology. 1978;16(5):273-8.
Silverman, et al. Influence of promethazine on symptom-therapy scores for nausea during patient-controlled analgesia with morphine. Anesth Analg. May 1992;74(5):735-8.
Song, et al. Quantitation of promethazine and metabolites in urine samples using on-line solid-phase extraction and column-switching. J Chromatogr B Biomed Sci Appl. Nov. 5, 2001;763(1-2):9-20.
Stavchansky, et al. Bioequivalence and pharmacokinetic profile of promethazine hydrochloride suppositories in humans. J Pharm Sci. Jun. 1987;76(6):441-5.
Stavrovskaya, et al. Clinically approved heterocyclics act on a mitochondrial target and reduce stroke-induced pathology. J Exp Med. Jul. 19, 2004;200(2):211-22.
Steyer, et al. Mehrdimensionaler Befindlichkeitsfrageboen. [Multi-dimensional well-being questionnaire] Gottingen: Hogrefe. 1997.
Strenkoski-Nix, et al. Pharmacokinetics of promethazine hydrochloride after administration of rectal suppositories and oral syrup to healthy subjects. Am J Health Syst Pharm. Aug. 15, 2000;57(16):1499-505.
Sullivan, et al. The pain catastrophizing scale: development and validation. Psychological Assessment, vol. 7(4), Dec. 1995, 524-532.
Suzuki Takahiro. Utilize codeine phosphate. Journal of Pain and Clinical Medicine (2006), vol. 6, No. 1, p. 77-82. (in Japanese with English translation).
Szyfelbein, et al. The assessment of pain and plasma beta-endorphin immunoactivity in burned children. Pain. Jun. 1985;22(2):173-82.
Takahama, K., et al. Central and peripheral mechanisms of narcotic antitussives: codeine-sensitive and -resistant coughs. Cough. 2007;3:8.
Takeda, et al. Strong opioid analgesics in cancer pain management—starting timing of administration. Cancer patient and symptomatic therapy 2003, vol. 14, No. 2, pp. 24-28 (in Japanese with English translation by Machine).
Tanaka, et al. Blockade of Na+ current by promethazine in guinea-pig ventricular myocytes. Br J Pharmacol. Aug. 1992;106(4):900-5.
Tarkkila, et al. Premedication with promethazine and transdermal scopolamine reduces the incidence of nausea and vomiting after intrathecal morphine. Acta Anaesthesiol Scand. Oct. 1995;39(7):983-6.
Taylor, et al. Pharmacokinetics of promethazine and its sulphoxide metabolite after intravenous and oral administration to man. Br J Clin Pharmacol. Mar. 1983;15(3):287-93.
Thoden, et al. Adverse non-drug reactions (ANDRs) in patients with muscle-contraction headache. Clin Pharmacol Ther. 1990; 47:149.
Tomkins, et al. Effect of cytochrome P450 2D1 inhibition on hydrocodone metabolism and its behavioral consequences in rats. J Pharmacol Exp Ther. Mar. 1997;280(3):1374-82.
Tsuruzaki, et al. Maternal consumption of antipyretic analgesics produces chromosome anomalies in F1 embryos. Teratology. 1982; 26:42A.
Urie, et al. Pharmacy education: palliative care symptom control. In:The Pharmaceutical Journal. 2000; 265:603.
U.S. Appl. No. 12/967,423, filed Dec. 14, 2010.
U.S. Appl. No. 13/347,552, filed Jan. 10, 2012.
U.S. Appl. No. 14/036,946, filed Sep. 25, 2013.
U.S. Appl. No. 14/099,432, filed Dec. 6, 2013.
U.S. Appl. No. 14/099,432 Non-Final Office Action Mailed Jun. 3, 2016.
U.S. Appl. No. 14/244,455 Notice of Allowability Mailed Mar. 8, 2016.
U.S. Appl. No. 14/244,455 Notice of Allowance Mailed May 17, 2016.
U.S. Appl. No. 14/748,605, filed Jun. 24, 2015.
U.S. Appl. No. 14/748,605 Notice of Allowance Mailed May 6, 2016.
U.S. Appl. No. 14/748,609, filed Jun. 24, 2015.
U.S. Appl. No. 14/748,609 Notice of Allowance Mailed May 3, 2016.
U.S. Appl. No. 14/748,613, filed Jun. 24, 2015.
U.S. Appl. No. 14/748,614, filed Jun. 24, 2015.
U.S. Appl. No. 14/748,614 Notice of Allowance Mailed May 20, 2016.
U.S. Appl. No. 14/748,617, filed Jun. 24, 2015.
U.S. Appl. No. 14/748,621, filed Jun. 24, 2015.
U.S. Appl. No. 14/748,621 Notice of Allowance Mailed May 3, 2016.
U.S. Appl. No. 14/789,883, filed Jul. 1, 2015.
U.S. Appl. No. 14/789,883 Final Office Action Mailed Mar. 17, 2016.
U.S. Appl. No. 14/789,886, filed Jul. 1, 2015.
U.S. Appl. No. 14/789,886 Final Office Action Mailed Mar. 18, 2016.
U.S. Appl. No. 14/789,888, filed Jul. 1, 2015.
U.S. Appl. No. 14/789,888 Notice of Allowance Mailed Apr. 5, 2016.
U.S. Appl. No. 14/789,888 Notice of Allowance Mailed May 20, 2016.
U.S. Appl. No. 14/930,496, filed Nov. 2, 2015.
U.S. Appl. No. 60/948,375, filed Jul. 6, 2007.
U.S. Appl. No. 61/020,139, filed Jan. 9, 2008.
U.S. Appl. No. 61/043,037, filed Apr. 7, 2008.
U.S. Appl. No. 61/060,758, filed Jun. 11, 2008.
U.S. Appl. No. 61/223,999, filed Jul. 8, 2009.
U.S. Appl. No. 61/224,424, filed Jul. 9, 2009.
U.S. Pharmacopeia National Formulary Supplement. USP 23-NF 18, 9th dated Nov. 15, 1998, p. 4678.
Vaisman, et al. The effect of promethazine hydrochloride on bilirubin metabolism in the rat. Pediatr Res. Sep. 1976;10(9):788-91.
Vinson, D.R. Treatment patterns of isolated benign headache in US emergency departments. Ann Emerg Med. Mar. 2002;39(3):215-22. (Abstract).
Vollbracht, et al. New treatments for headache. Neurol Sci. May 2014;35 Suppl 1:89-97. doi: 10.1007/s10072-014-1747-z.
Walsh, et al. The relative abuse liability of oral oxycodone, hydrocodone and hydromorphone assessed in prescription opioid abusers. Drug Alcohol Depend. Dec. 1, 2008;98(3):191-202. doi: 10.1016/j.drugalcdep.2008.05.007. Epub Jul. 7, 2008.
Ward, et al. The chronic hepatic or renal toxicity of di(2-ethylhexyl) phthalate, acetaminophen, sodium barbital, and phenobarbital in male B6C3F1 mice: autoradiographic, immunohistochemical, and biochemical evidence for levels of DNA synthesis not associated with carcinogenesis or tumor promotion. Toxicol Appl Pharmacol. Dec. 1988;96(3):494-506.
Ware, et al. The MOS 36-item short-form health survey (SF-36). I. Conceptual framework and item selection. Med Care. Jun. 1992;30(6):473-83.
Watcha, et al. Postoperative nausea and vomiting. Its etiology, treatment, and prevention. Anesthesiology. Jul. 1992;77(1):162-84.
Weisburger, et al. Effect of acetanilide and p-hydroxyacetanilide on the carcinogenicity of N-2-fluorenylacetamide and N-hydroxy-N-

(56) References Cited

OTHER PUBLICATIONS 2-fluorenylacetamide in mice, hamsters, and female rats. J Natl Cancer Inst. Jul. 1973;51(1):235-40.

Wesson, et al. The Clinical Opiate Withdrawal Scale (COWS). J Psychoactive Drugs. Apr.-Jun. 2003;35(2):253-9.

Whitcomb, et al. Association of acetaminophen hepatotoxicity with fasting and ethanol use. JAMA. Dec. 21, 1994;272(23):1845-50.

Whitfield, et al. Parsimonious and efficient assessment of health-related quality of life in osteoarthritis research: validation of the Assessment of Quality of Life (AQoL) instrument. Health Qual Life Outcomes. 2006; 4:19.

Wiger, et al. Effects of acetaminophen and hydroxyurea on spermatogenesis and sperm chromatin structure in laboratory mice. Reprod Toxicol. Jan.-Feb. 1995;9(1):21-33.

Wikipedia. Acetaminophen. en.wikipedia.org/wiki/Acetaminophen. Last Accessed Aug. 22, 2012.

Wikipedia. Hydrocodone. en.wikipedia.org/wiki/Hydrocodone Last Accessed Aug. 22, 2012.

Williams, et al. Inhibition by acetaminophen of intestinal cancer in rats induced by an aromatic amine similar to food mutagens. Eur J Cancer Prev. Aug. 1997;6(4):357-62.

Wirth, et al. Mechanism of N-hydroxyacetylarylamine mutagenicity in the *Salmonella* test system: metabolic activation of N-hydroxyphenacetin by liver and kidney fractions from rat, mouse, hamster, and man. Mol Pharmacol. Jul. 1980;18(1):117-27.

Wyeth Pharmaceuticals, I. (2010). Phenergan® (promethazine HCl) Tablets and Suppositories Full Prescribing Information. http://www.accessdata.fda.gov/drugsatfda_docs/label/2004/07935s030lbl.pdf. Philadelphia, PA, Wyeth Pharmaceuticals, Inc.: 1-10.

Wyeth Pharmaceuticals Inc. Phenergan® Label. 2005.

Wyeth Pharmaceuticals, Inc. Phenergan Tablets. United States Prescribing Information (NDA 007935; drugs@fda.gov, listed PI update as of Nov. 2004) for Phenergan®- promethazine hydrochloride, tablet.

Yaghmour, et al. Multimodal Anesthesia and Analgesia Facilitates Ambulatory Discharge of Patients Undergoing Osseous Reconstructive Ankle Surgery (RAS). Anesthesiology 2003; 99: A19 URL:http://www.asaabstracts.com/strands/asaabstracts/abstract.htm;jsessionid=D8FB91F2211878C2D0D08A062AA48B1E?year=2003&index=1&absnum=1516.

Yoon, et al. Chemical mutagenesis testing in *Drosophila*. IV. Results of 45 coded compounds tested for the National Toxicology Program. Environ Mutagen. 1985;7(3):349-67.

York, et al. Developmental toxicity studies in rats and rabbits with orally administered hydrocodone bitartrate (HB), USP. Reprod Toxicol. 2003; 17: 507.

Yoshida, et al. Mutagenicity of p-aminophenol in *Escherichia coli* WP2uvrA/pKM101 and its relevance to oxidative DNA damage. Mutat Res. Jul. 8, 1998;415(1-2):139-50.

Zacny, et al. Profiling the subjective, psychomotor, and physiological effects of a hydrocodone/acetaminophen product in recreational drug users. Drug Alcohol Depend. Jun. 1, 2005;78(3):243-52. Epub Jan. 12, 2005.

Zacny, et al. Subjective, psychomotor, and physiological effects profile of hydrocodone/acetaminophen and oxycodone/acetaminophen combination products. Pain Med. May-Jun. 2008;9(4):433-43. doi: 10.1111/j.1526-4637.2007.00359.x.

Zacny, et al. Within-subject comparison of the psychopharmacological profiles of oral hydrocodone and oxycodone combination products in non-drug-abusing volunteers. Drug Alcohol Depend. Apr. 1, 2009;101(1-2):107-14. doi: 10.1016/j.drugalcdep.2008.11.013. Epub Dec. 31, 2008.

Zaman, et al. Bioequivalency and dose proportionality of three tableted promethazine products. Biopharm Drug Dispos. May-Jun. 1986;7(3):281-91.

Zenser, et al. Enzyme systems involved in the formation of reactive metabolites in the renal medulla: cooxidation via prostaglandin H synthase. Fundam Appl Toxicol. Dec. 1984;4(6):922-9.

Zhelev, et al. Phenothiazines suppress proliferation and induce apoptosis in cultured leukemic cells without any influence on the viability of normal lymphocytes. Phenothiazines and leukemia. Cancer Chemother Pharmacol. Mar. 2004;53(3):267-75. Epub Dec. 9, 2003.

Zimmerman, et al. Acetaminophen (paracetamol) hepatotoxicity with regular intake of alcohol: analysis of instances of therapeutic misadventure. Hepatology. Sep. 1995;22(3):767-73.

Zohydro Label. Zogenix Inc. Oct. 2013.

International Application No. PCT/US2015/025481 International Preliminary Report on Patentability Issued Oct. 12, 2016.

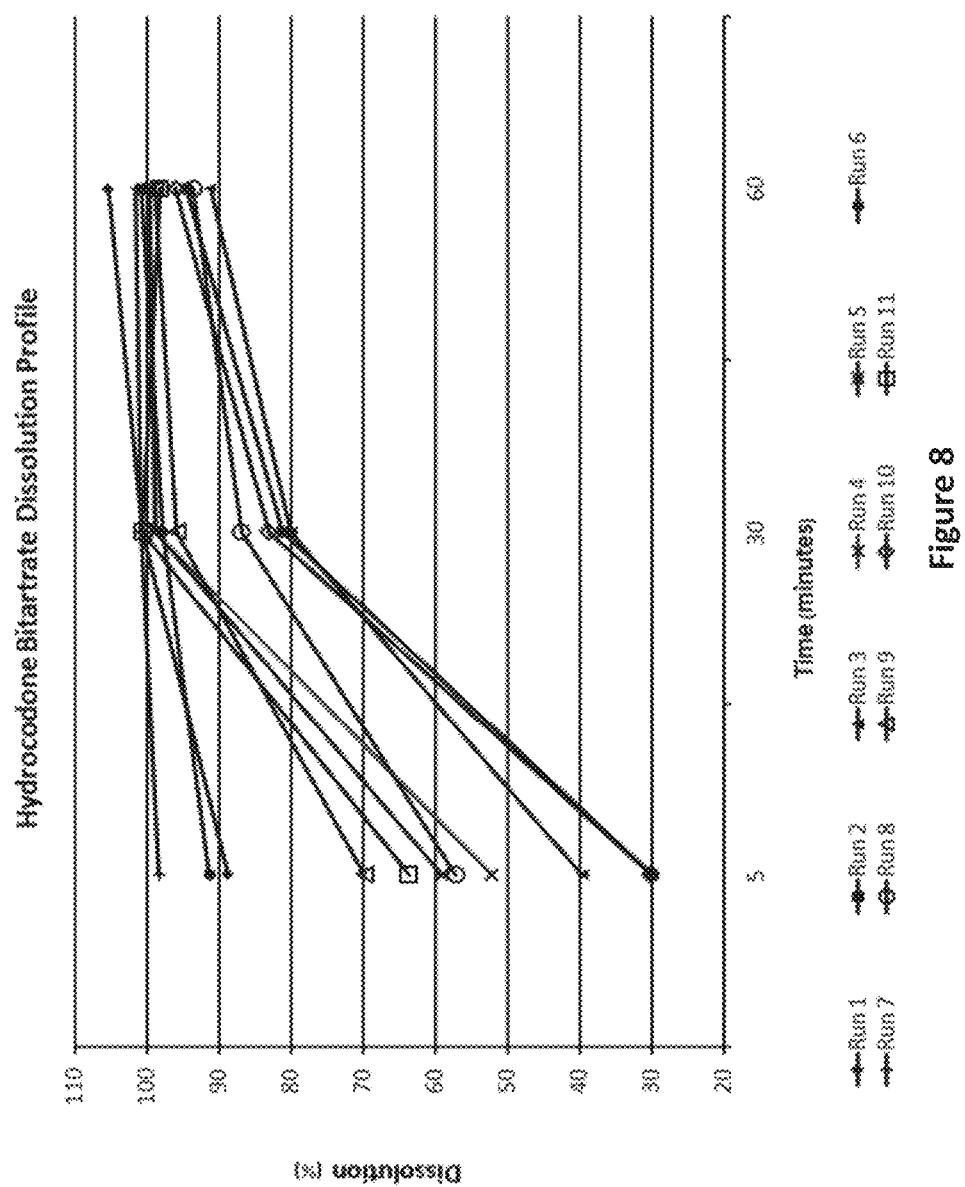

PHARMACEUTICAL COMPOSITIONS FOR TREATING OR PREVENTING PAIN

CROSS-REFERENCE

This application is a continuation application of U.S. application Ser. No. 14/244,455, filed Apr. 3, 2014, now U.S. Pat. No. 9,433,625, which is a continuation application of U.S. application Ser. No. 12/967,423, filed Dec. 14, 2010, now U.S. Pat. No. 8,728,522, which is a continuation-in-part application of International Application No. PCT/US2010/041433, filed Jul. 8, 2010, which claims the benefit of U.S. Provisional Application No. 61/223,999, filed Jul. 8, 2009, and U.S. Provisional Application No. 61/224,424, filed Jul. 9, 2009, each of which is incorporated by reference herein in their entirety.

BACKGROUND OF THE INVENTION

Available pain medications may have adverse effects, such as nausea, vomiting, and skin rashes and sedation. As a result of such adverse effects, many subjects are unable to tolerate recommended dosages needed for effective pain relief because of adverse effects. Accordingly, there remains a need for effective therapeutics with reduced adverse effects.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

In one aspect, provided herein is a pharmaceutical composition in the form of a bi-layer tablet comprising: an immediate release layer comprising: about 5 mgs to about 20 mgs of promethazine or a pharmaceutically acceptable salt thereof, about 75 mgs to about 150 mgs of silicified microcrystalline cellulose, about 5 mgs to about 20 mgs of croscarmellose sodium, and about 0.2 mgs to about 5 mgs of magnesium stearate; and a controlled release layer comprising: about 250 mgs to about 400 mgs of acetaminophen, or a pharmaceutically acceptable salt thereof, about 2 mgs to about 15 mgs of hydrocodone, or a pharmaceutically acceptable salt thereof, about 100 mgs to about 250 mgs of silicified microcrystalline cellulose, about 5 mgs to about 30 mgs of hydroxy methyl propyl cellulose, about 0.5 mgs to about 5 mgs magnesium stearate, and about 0.5 mgs to about 10 mgs stearic acid. In one embodiment the immediate release layer comprises: about 12.5 mgs of promethazine HCL, about 121 mgs of silicified microcrystalline cellulose, about 15 mgs of croscarmellose sodium, and about 1 mg of magnesium stearate; and the controlled release layer comprises: about 361 mgs of acetaminophen, about 8 mgs of hydrocodone bitartrate, about 155 mgs of silicified microcrystalline cellulose, about 20 mgs of hydroxy methyl propyl cellulose, about 2.75 mgs magnesium stearate, and about 2.75 mgs stearic acid. In another embodiment, at least about 90% of the promethazine is released within the first 10 minutes. In another embodiment, at least about 90% of the promethazine is released within the first 5 minutes. In another embodiment, less than about 80% of the acetaminophen is released within the first 30 minutes. In another embodiment, less than about 80% of the hydrocodone is released within the first 30 minutes. In another embodiment, the bilayer tablet has a hardness of between about 7 and about 15 kp. In another embodiment, the bilayer tablet has a hardness of about 12 kp. In another embodiment, the immediate release layer has a faster dissolution rate than the controlled release layer.

In another aspect, provided herein is a method of treating or preventing pain or discomfort in a subject in need thereof by administering a pharmaceutical composition in the form of a bi-layer tablet comprising: an immediate release layer comprising: about 5 mgs to about 20 mgs of promethazine or a pharmaceutically acceptable salt thereof, about 75 mgs to about 150 mgs of silicified microcrystalline cellulose, about 5 mgs to about 20 mgs of croscarmellose sodium, and about 0.2 mgs to about 5 mgs of magnesium stearate; and a controlled release layer comprising: about 250 mgs to about 400 mgs of acetaminophen, or a pharmaceutically acceptable salt thereof, about 2 mgs to about 15 mgs of hydrocodone, or a pharmaceutically acceptable salt thereof, about 100 mgs to about 250 mgs of silicified microcrystalline cellulose, about 5 mgs to about 30 mgs of hydroxy methyl propyl cellulose, about 0.5 mgs to about 5 mgs magnesium stearate, and about 0.5 mgs to about 10 mgs stearic acid. In one embodiment, the subject experiences a reduction in a symptom associated with the administration of hydrocodone. In another embodiment, the symptom associated with the administration of hydrocodone is nausea, vomiting, gastric upset, skin rash or an allergic reaction. In another embodiment, the subject is 0-12 years old. In another embodiment, the subject is about age 65 or older. In another embodiment, the discomfort is a headache. In another embodiment, the headache is a migraine headache, cluster headache, hemicrania continua headache, chronic headache, tension headache or chronic tension headache. In another embodiment, the discomfort is photophobia.

BRIEF DESCRIPTION OF DRAWINGS

FIG. 8 illustrates an example of the hydrocodone bitartrate dissolution release profiles for the analgesic compositions of Example 18.

DETAILED DESCRIPTION OF THE INVENTION

Figure 1:
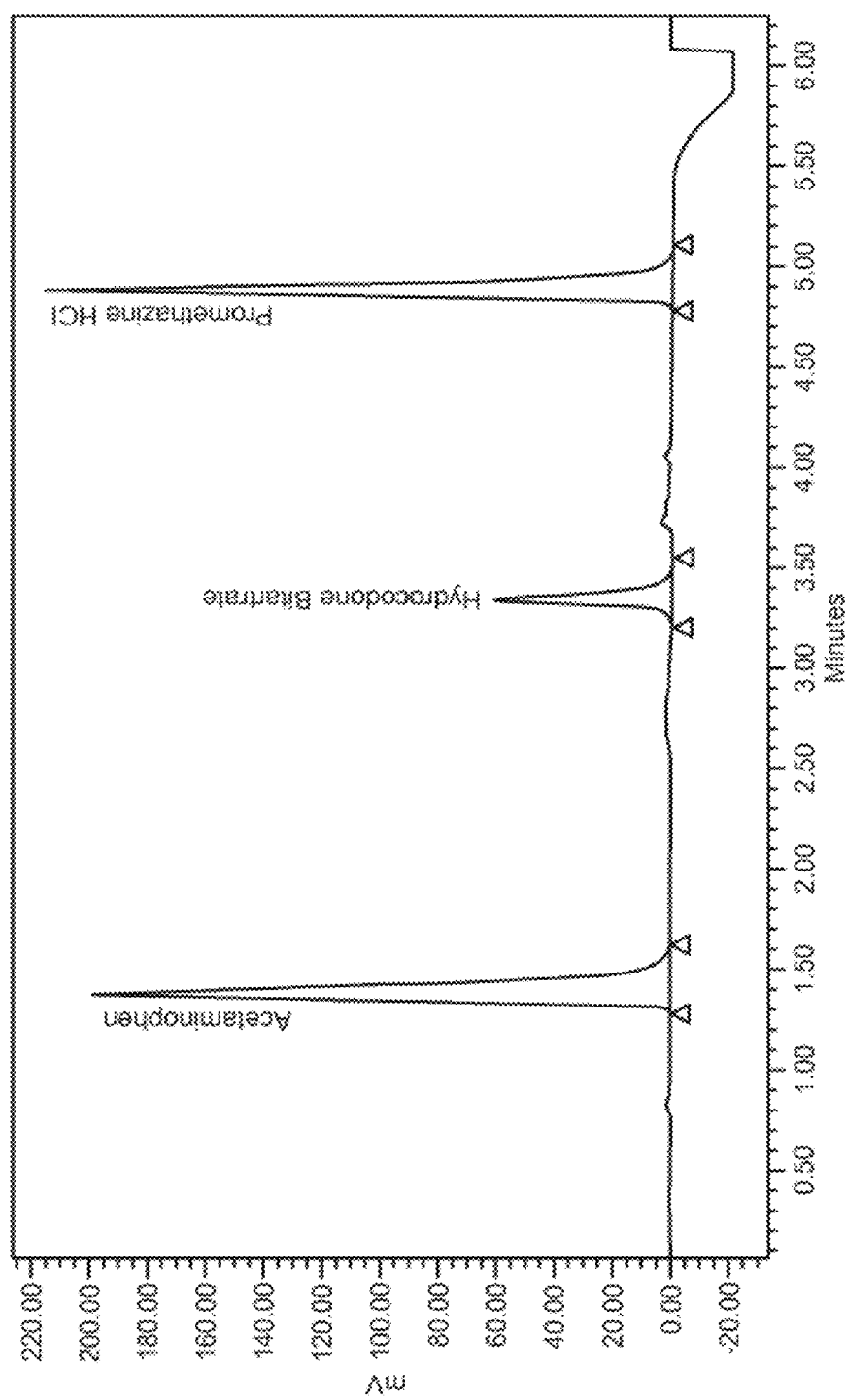
FIG. 1 illustrates a chromatograph for example of a standard solution.

All patents and publications and referred to herein are incorporated by reference in their entirety.

The present invention is generally directed to compositions comprising multiple pharmaceutically active agents that are useful as therapeutics that alleviate, abate or eliminate one or more conditions in a subject in need thereof, as further described herein below.

Exemplary Combinations

Various embodiments of the present invention are directed to compositions comprising an effective amount of a combination of one or more active agents. In some embodiments, the combination of one or more active agents is in a single formulation. Pharmaceutically active agents disclosed herein are capable of use in a composition of the invention. Moreover, upon reading the disclosure herein additional active agents useful in the present invention will be known to those of skill in the art.

In some embodiments, the invention is directed to the combination of an effective amount of an opioid with an effective amount of least one other active ingredient. Non-limiting examples of opioid analgesic agents useful in the present invention include hydrocodone, oxycodone, acetyldihydrocodeinone, diamorphine, codeine, pethidine, alfentanil, buprenorphine, butorphanol, codeine, dezocine, fentanyl, hydromorphone, levomethadyl acetate, levorphanol, meperidine, methadone, morphine sulfate, nalbuphine, oxymorphone, pentazocine, propoxyphene, remifentanil, sufentanil, tramadol, or a pharmaceutically acceptable salt thereof.

In some embodiments, the opioid analgesic agent is hydrocodone, oxycodone, propoxyphene, or fentanyl or a pharmaceutically acceptable salt thereof. In various embodiments disclosed herein the opioid analgesic agent is hydrocodone, a pharmaceutically acceptable salt or its thiosemicarbazone, p-nitrophenylhydrazone, o-methyloxime, semicarbazone, or bis (methylcarbamate). In further embodiments disclosed herein the opioid analgesic agent is oxycodone, a pharmaceutically acceptable salt or its thiosemicarbazone, p-nitrophenylhydrazone, o-methyloxime, semicarbazone, or bis-methylcarbamate. In some embodiments the opioid analgesic is hydrocodone bitartrate.

In other embodiments, the invention is directed to a combination of an effective amount of a triptan with an effective amount of at least one other active agent. Non-limiting examples of triptans useful in the present invention include naratriptan, almotriptan, sumatriptan, zolmitriptan, eletriptan, frovatriptan, naratriptan and rizatriptan. In various embodiments disclosed herein the triptan is sumatriptan or a pharmaceutically acceptable salt thereof. In further embodiments disclosed herein the sumatriptan salt is sumatriptan succinate.

In some embodiments, the other active agent in combination with the opioid analgesic or triptan analgesic is a non-opioid analgesic. Non-limiting examples of non-opioid analgesics useful in the present invention include aspirin; acetaminophen; a non-steroidal anti-inflammatory drug (NSAID), an arylalkanoic acid, a profen, a fenamic acid, an oxicam, a pyrazolidine derivative; a Cox-2 inhibitor, a local analgesic; an anti-depressant, an atypical analgesic, a psychotropic agent, an NMDA receptor antagonist, an $\alpha_2$-adrenoreceptor agonists and a synthetic drug having narcotic properties. In various embodiments disclosed herein the non-opioid analgesic agent is acetaminophen, naproxen or a pharmaceutically acceptable salt thereof.

Non-limiting examples of NSAIDs include salicylates such as amoxiprin, benorilate, choline magnesium salicylate, diflunisal, faislamine, methyl salicylate, and magnesium salicylate. Non-limiting examples of arylalkanoic acids include diclofenac, aceclofenac, acemetacin, bromfenac, etodolac, indometacin, nabumetone, sulindac, and tolmetin. Non-limiting examples of profens include ibuprofen, carprofen, fenbuprofen, flubiprofen, ketaprofen, ketorolac, loxoprofen, naproxen, and suprofen. Non-limiting examples of fenamic acids include mefenamic acid and meclofenamic acid. Non-limiting examples of oxicams include piroxicam, lomoxicam, meloxicam and tenoxicam. Non-limiting examples of pyrazolidine derivatives include phenylbutazone, azapropazone, metamizole, oxyphenbutazone, and sulfinprazone. Non-limiting examples of Cox-2 inhibitors include valdecoxib, celecoxib and rofecoxib. Non-limiting examples of analgesics include lidocaine and mexiletine. Non-limiting examples of anti-depressants include amitriptyline, carbamazepine, gabapentin, pregabalin, amoxapine, clomipramine, desipramine, dosulepin, doxepin, imipramine, iprindole, lofepramine, nortriptyline, opipramol, protryptyline, and trimipramine. Non-limiting atypical analgesic include orphenadrine, cyclobenzaprine, scopolamine, atropine and gabapentin. A non-limiting example of a psychotropic agent is tetrahydrocannabinol. Non-limiting examples of NMDA receptor antagonists include ketamine, amantadine, dextromethorphan, dextrorphan, ibogaine, phencyclidine, riluzole, tiletamine, memantine, dizocilpine, patiganel and remacimide. A non-limiting example of a $\alpha_2$-adrenoreceptor agonist is clonidine. A non-limiting example of a synthetic drug having narcotic properties is tramadol.

In some embodiments, the other active agent in combination with the opioid analgesic or triptan analgesic is an abuse deterrent agent. Non-limiting examples of abuse deterrent agents useful in the present invention include unalmefene, naloxone, niacin, and naltrexone.

In some embodiments, the other active agent in combination with the opioid analgesic or triptan analgesic is an antitussive. Non-limiting examples of antitussives useful in the present invention include dextromethorphan, dextrorphan, noscapine, ethyl morphine, codeine, camphor, menthol, theobromine and guaifenesin.

In some embodiments, the other active agent in combination with the opioid analgesic or triptan analgesic is an antiemetic and/or antihistamine. Non-limiting examples of antiemetic agents useful in the present invention include aprepitant, dronabinol, perphenazine, palonosetron, trimethyobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabis, midazolam, lorazepam, hyoscine, dexamethasone, emetrol and propofol.

In some embodiments, another active agent in combination with the opioid analgesic or triptan analgesic is a barbiturate active agent. Non-limiting examples of barbiturate agents useful in the present invention include allobarbital, alphenal, amobarbital, aprobarbital, barbexaclone, barbital, brallobarbital, butabarbital, butalbital, butobarbital, butallylonal, crotylbarbital, cyclobarbital, cyclopal, ethallobarbital, febarbamate, heptabarbital, hexethal, hexobarbital, mephobarbital, metharbital, methohexital, methylphenobarbital, narcobarbital, nealbarbital, pentobarbital, primidone, probarbital, propallylonal, proxibarbal, proxibarbital, reposal, secbutabarbital, secobarbital, sigmodal, talbutal, thialbarbital, thiamylal, thiobarbital, thiobutabarbital, thiopental, valofane, vinbarbital, vinylbital, 1,3-dimethoxymethyl 5,5-diphenyl-barbituric acid (DMMDPB), 1-monomethoxymethyl 5,5-diphenylbarbituric acid (MMMDPB) and a diphenyl-barbituric acid (DPB), including any of their precursors, derivatives and analogs or a combination thereof.

In some embodiments, another active agent in combination with the opioid analgesic or triptan analgesic is an antihistamine. Non-limiting examples of antihistamines useful in the present invention include H1 agonists, H1 antagonists, H2 agonists, H2 antagonists, H3 agonists, H3 antagonists, H4 agonists and H4 antagonists. A specific example of an H1 agonist or partial agonist is 2-(m-fluorophenyl)-histamine. Examples of H1 antagonists include chlorpheniramine, scopolamine, mepyramine, terfenadine, astemizole, and triprolidine. Other antagonists, which may be further classified by their chemical structures, include the ethanolamines carbinoxamine, dimenhydrinate, diphenhydramine, and doxylamine; the ethylaminediamines pyrilamine and tripelennamine; the piperazine derivatives dydroxyzine, cyclizine, fexofenadine and meclizine; the alkylamines brompheniramine and chlorpheniramine; and miscellaneous antagonists cyproheptadine, loratadine, cetrizine. Examples of H2 agonists include dimaprit, impromidine, and amthamine. Examples of H2 antagonists include cimetidine, ranitidine, nizatidine, and famotidine. Examples of H3 agonists include R-alpha-methylhistamine, imetit, and immepip. Examples of H3 antagonists include thioperamide, iodophenpropit, and clobenpropit. Examples of H4 agonists include clobenpropit, imetit, and clozapine. A specific example of an H4 antagonist is thioperamide.

In various specific embodiments of the invention, the antihistamine is promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol, or propofol.

In some embodiments, another active agent in combination with the opioid analgesic or triptan analgesic is an H1 blocker. Examples of H1 blockers useful in the present invention include azelastine, brompheniramine, buclizine, carbinoxamine, cetrizine, chlorpheniramine, clemastine, cyclizine, cyproheptadine, desloratidine, dimenhydrinate, diphenhydramine, emedastine, fexofenadine, hydroxyzine, ketotifen, levocabastine, loratadine, meclizine, olopatadine, phenindamine, and promethazine.

In some embodiments, another active agent in combination with the opioid analgesic or triptan analgesic is a stimulant agent. Non-limiting examples of stimulant agents useful in the present invention include aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof. In various embodiments disclosed herein the stimulant agent provides an anti-sedative effect.

In some embodiments, another active agent in combination with the opioid analgesic or triptan analgesic is an amphetamine. Non-limiting examples of amphetamines useful in the present invention include methamphetamine, levoamphetamine, dextroamphetamine, 3,5-methyloxy amphetamine, 2,5-dimethoxy-4-methylthioamphetamine, 2,5-dimethoxy-4-ethylthioamphetamine, 2,5-dimethoxy-4-(i)-propylthioamphetamine, 2,5-dimethoxy-4-phenylthioamphetamine, 2,5-dimethoxy-4-(n)-propylthioamphetamine, Brolamfetamine, 2,5-dimethoxy-4-iodoamphetamine, 2,5-Dimethoxy-4-methylamphetamine, 2,5-Dimethoxy-4-butyl-amphetamine, 3,4-Dimethyl-2,5-dimethoxyamphetamine, 2-Phenylethylamine, propylamphetamine, methylphenidate, lisdexamfetamine, ethylamphetamine, MDMA (3,4-methylenedioxy-N-methylamphetamine), MDEA (3,4-methylenedioxy-N-ethylamphetamine), PMA (p-methoxyamphetamine), DMA (2-(2,4-Dimethoxy-phenyl)-1-methyl-ethylamine), benzphetamine, 4-FMP (para-fluoroamphetamine), and 4-MTA (4-Methylthioamphetamine).

In some embodiments, another active agent in combination with the opioid analgesic or triptan analgesic are beta blockers, serotonin receptor agonists, vasoconstrictors, anti-platelet agents, anti-consultants, triptans, ergots, or calcitonin-gene-related peptide (CGRP) receptor antagonists.

Non-limiting examples of a beta blockers useful in the present invention include acebutolol, arotinolol, atenolol, betaxolol, bisoprolol, butoxamine, carvedilol, carteolol, esmolol, carteolol, carvedilol, labetalol, levobunolol, mepindolol, metoprolol, nebivolol, nadolol, oxprenolol, penbutolol, propranolol, pindolol, sotalol, and timolol. In some specific embodiments, the beta blocker is propranolol.

Non-limiting examples of serotonin receptor agonists useful in the present invention include buspirone, mescaline, psilocybin, cisapride, triptans, and lysergic acid diethylamide.

Non-limiting examples of vasoconstrictors useful in the present invention include isometheptene mucate, amphetamines, antihistamines, cocaine, caffeine, pseudoephedrine, ergine, methylphenidate, psilocybin, and stimulants, including amphakines or other drugs effective to glutagatergic AMPA receptors and benzoylpiperidine derivatives.

Non-limiting examples of anti-platelet agents useful in the present invention include acetylsalicylic acid, clopidogrel, ticlopidine, cilostazol, abciximab, eptifibatide, tirofiban defibrotide and dipyridamole.

Non-limiting examples of anti-convulsants useful in the present invention include topiramate, divaprex, phenobarbital, methlyphenobarbital, metharbital, barbexaclone, stiripentol, clobazam, clonazepam, clorazepate, diazepam, midazolam, lorazepam, nitrazepam, temazepam, nimetazepam, potassium bromide, felbamate, carbamazepine, oxcarbazepine, vigabatrin, progabide, tiagabine, gabapentin, prgabalin, ethotoin, phenytoin, mephenytoin, fosphenytoin, paramethadione, trimethadione, ethadione, beclaminde, primidone, brivaracetam, levetiracetam, seletracetam, ethsuximide, phesuximide, mesuximide, acetazolamide, sulthiame, methazolamide, zonisamide, lamotrigine, pheneturide, phenacemide, valpromide, and valnoctamide.

Non-limiting examples of calcitonin-gene-related peptide (CGRP) receptor antagonists useful in the present invention include MK-0974, CGRP8-37, BIBN 4096 BS, quinine, nitrobenzamide, 4-oxobutanamides, cyclopropane derivatives, and benzimidazolinyl piperidines.

Non-limiting examples of ergots useful in the present invention include ergotamine, methysergide, and zonisamide.

Each agent disclosed herein and used in the present invention can be used in the form of a free base, a pharmaceutically acceptable salt, a prodrug, an analog and/or a complex. As used herein, a pharmaceutically acceptable salt includes, but is not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparginate salts, glutamate salts, and the like.

In addition, pharmaceutically acceptable salts include bitartrate, bitartrate hydrate, hydrochloride, p-toluenesulfonate, phosphate, sulfate, trifluoroacetate, bitartrate hemipentahydrate, pentafluoropropionate, hydrobromide, mucate, oleate, phosphate dibasic, phosphate monobasic, acetate trihydrate, bis(heptafuorobutyrate), bis(pentafluoropropionate), bis(pyridine carboxylate), bis(trifluoroacetate), chlorhydrate, and sulfate pentahydrate.

Other representative pharmaceutically acceptable salts include, e.g., watersoluble and water-insoluble salts, such as the acetate, amsonate(4,4-diaminostilbene-2,2-disulfonate), benzenesulfonate, benzonate, bicarbonate, bisulfate, bitartrate, borate, butyrate, calcium edetate, camphorsulfonate, camsylate, carbonate, citrate, clavulariate, dihydrochloride, edetate, edisylate, estolate, esylate, fiunarate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A hydrate is another example of a pharmaceutically acceptable salt.

In various specific embodiments of the invention disclosed herein, the composition comprises an effective amount of each of an opioid analgesic agent and a non-opioid analgesic agent, where the opioid analgesic agent/non-opioid analgesic agent is codeine/acetaminophen, codeine/aspirin, codeine/naproxen, codeine/ibuprofen, hydrocodone/acetaminophen, hydrocodone/ibuprofen, hydrocodone/naproxen, hydrocodone/aspirin, oxycodone/acetaminophen, oxycodone/aspirin, oxycodone/naproxen, oxycodone/ibuprofen, propoxyphene/aspirin, propoxyphene/ibuprofen, propoxyphene/acetaminophen, or propoxyphene/naproxen, wherein the opioid analgesic agent or non-opioid analgesic agent is optionally in the form of a or a pharmaceutically acceptable salt thereof. In various specific embodiments, the hydrocodone salt is hydrocodone bitartrate, the oxycodone salt is oxycodone HCl, and the naproxen salt is naproxen Na or Mg.

In other specific embodiments of the invention disclosed herein, the compositions described in the above paragraph further comprises an effective amount of one or more of an opioid antagonist agent, abuse deterrent agent, a barbiturate agent a stimulant agent or an antiemetic agent.

In various specific embodiments of the invention described herein, the composition comprises an effective amount of at least two analgesics and an effective amount of one or more additional pharmaceutically active agents. In a specific embodiment of this aspect of the invention, the composition further comprises an effective amount of an antihistamine or antiemetic.

In various embodiments of the invention describe herein, the composition of the invention comprises an effective amount of each of an opioid analgesic agent, a non-opioid analgesic agent and an active agent useful for reducing or eliminating adverse effects, such as an antihistamine or an antiemetic, as described herein.

In other embodiments, the composition comprises an effective amount of each of an opioid agent; a non-opioid agent; a barbiturate agent and optionally an antiemetic.

In various embodiments of the invention described herein, the compositions comprise an effective amount of two, three, four, five, six or more of the active agents described herein. In various specific embodiments of the invention described herein at least one of the active agents is an antiemetic or antihistamine. In other embodiments, the composition does not comprise promethazine or a pharmaceutically acceptable salt of promethazine.

In a specific embodiment of the invention, the composition comprises an effective amount of each of hydrocodone or oxycodone, or a pharmaceutically acceptable salt thereof, modafinil or caffeine or a pharmaceutically acceptable salt thereof and optionally promethazine or a pharmaceutically acceptable salt thereof.

In other embodiments, the composition comprises an effective amount of each of an opioid agent; a barbiturate agent; a stimulant agent; and optionally a non-opioid agent. In some embodiments the composition further comprises an effective amount of an antiemetic.

In yet other embodiments, the composition comprises an effective amount of each of an opioid agent; and a barbiturate agent. In another embodiment a composition comprises an effective amount of a non-opioid agent; a barbiturate agent; and an antiemetic.

In another embodiment, the composition comprises an effective amount of each of a non-opioid agent; a barbiturate agent; and a stimulant agent. In some embodiments the composition further comprises an antiemetic.

In another embodiment a composition comprises an effective amount of a barbiturate agent and an effective amount of a stimulant agent. In some embodiments the composition further comprises an effective amount of an antiemetic.

In another embodiment a composition comprises an effective amount of a non-opioid agent and an effective amount of a stimulant agent. In some embodiments the composition further comprises an effective amount of an antiemetic.

In some embodiments the composition comprises an analgesic agent (e.g., one analgesic or two, three or more analgesics) and a second agent (e.g., one, two or more of an antihistamine or antiemetic) that reduces or eliminates an adverse effect of an analgesic agent.

In one embodiment, a composition comprise, an effective amount of an opioid analgesic agent, an effective amount of non-opioid analgesic agent, and an effective amount of an agent that reduces or eliminates an adverse effect of an analgesic agent.

Exemplary Dosage Amounts

In various embodiments of the invention described herein, the composition comprises multiple active agents at the same or different dosages. In some embodiments, the analgesic components may vary in dosages as further described herein, and the antihistamine or antiemetic dosage can be adjusted according to the particular analgesics used.

As those of skill in the art would recognize, the dosages and concentrations of active agents useful in the compositions described herein may be varied to achieve the effect desired. For example, the dosages administered can be adjusted based on the mode of administration, on the timing of administration and may be formulated to be administer once a day or for multiple administrations daily. In addition, dose levels can vary depending on the subject and/or condition being treated, the administration route used, as a function of the specific compound, as a function of the severity of the symptoms and/or the susceptibility of the subject to adverse effects.

In specific embodiments of the invention disclosed herein, each active agent in the composition is administered in a dosage of about 0.01 mg to 500 mg per kg body weight per day, e.g. about 20 mg/day for an average person. In some embodiments, dosage for each active agent in the composition is from about 0.01 to 5 mg, 1 to 10 mg, 5 to 20 mg, 10 to 50 mg, 20 to 100 mg, 50 to 150 mg, 100 to 250 mg, 150 to 300 mg, 250 to 500 mg, 300 to 600 mg or 500 to 1000 mg.

An "effective amount" of when used in connection with composition described herein is an amount sufficient to produce a therapeutic result in a subject in need thereof. For example a therapeutic result can include, but is not limited to, treating or preventing pain, nausea or vomiting by a subject.

An "effective amount" when in used in connection with one or more of the agents disclosed herein is the total amount of one or more of the agents that is useful for the treatment of pain.

The term "about" means the referenced numeric indication plus or minus 10% of that referenced numeric indication.

An "effective amount" when used in connection with an opioid analgesic agent alone or in combination is an amount that is effective for treating or preventing pain, wherein the antagonist agent is provided in combination with one or more pharmaceutically active agents disclosed herein. In one embodiment, the one or more pharmaceutically active agent is an antiemetic. In specific embodiments, the opioid analgesic agent is present in a dose of about 1.0 mg to about 100 mgs, including any single integer within this range.

An "effective amount" when used in connection with a triptan alone or in combination is an amount that is effective for treating or preventing a headache, including but not limited to, migraine headaches and/or cluster headaches, wherein the triptan is provided in combination with one or more pharmaceutically active agents disclosed herein. In various embodiments the one or more pharmaceutically active agent is an antiemetic. In various embodiments, the triptan is present in a dose of about 1.0 mg to about 100 mgs, including any single integer within this range. In specific embodiments, the triptan is sumatriptan and present in a dose of about 20 mg to about 60 mg, including any single integer within this range.

An "effective amount" when used in connection with a non-opioid analgesic agent alone or in combination is an amount that is effective for treating or preventing pain, wherein the non-opioid analgesic agent is provided in combination with one or more pharmaceutically active agents disclosed herein. In some embodiments the one or more pharmaceutically active agents include but are not limited to opioid analgesic agents and antiemetic agents. In various embodiments, the non-opioid analgesic agent is present in a dose from about 200 mgs to about 1000 mgs, including in the amount of any single integer within this range. In various specific embodiments of the invention, the non-opioid analgesic is acetaminophen and is present in an amount between about 200 mg to about 1000 mgs, including in the amount of any single integer within this range.

An "effective amount" when used in connection with an antiemetic agent is an amount that is effective for preventing or reducing or eliminating one or more adverse effects associated with one or more pharmaceutically active agent disclosed herein. In various embodiments, the one or more pharmaceutically active agent includes but is not limited to an opioid analgesic and/or a non opioid analgesic. In further embodiments, such adverse effects which are reduced, prevented or eliminated include but are not limited to incidence of nausea or vomiting. In various specific embodiments, the antiemetic is present in a dose from about 0.5 mg to about 200 mgs, including in the amount of any single integer within this range. In other embodiments of the invention the antiemetic is present in the amount of about 0.5 mg to about 60 mg, including in the amount of any single integer within this range. In specific embodiments, the antiemetic is promethazine or a salt thereof and is present in an amount of from about 0.5 mg to about 200 mgs, including any single integer within that range.

An "effective amount" when used in connection with an antihistamine is an amount that is effective for preventing or reducing the incidence of nausea or vomiting, or preventing or reducing adverse effects associated with an opioid analgesic (e.g., opioid-induced nausea and vomiting). In some embodiments of the invention described herein, the composition comprises an antihistamine at a lower dosage than that which the antihistamine is administered alone. In one embodiment, the antihistamine is provided in the composition at a dosage to prevent sedation, which may be observed with relatively higher dosages of promethazine or a salt thereof. Therefore, the antihistamine is provided at a dosage that is effective for reducing adverse affects associated with the opioid analgesic or non-opioid analgesic, but is at a relative low enough dosage to prevent sedation associated with the antihistamine or antiemetic.

In various specific embodiments, the antihistamine is present in a dose from about 0.5 mg to about 200 mgs, including in the amount of any single integer within this range. In other embodiments of the invention disclosed herein, the antihistamine is present in the range of at about 0.5 mg to about 60 mg, including in the amount of any single integer within this range. In specific embodiments, the antihistamine is promethazine or a salt thereof and is present in an amount of from about 0.5 mg to about 200 mgs, including any single integer within that range.

An "effective amount" when used in connection with a stimulant agent is an amount that is effective to increase alertness, or lessen soporific effects of an opioid agent, wherein the stimulant agent is present in a dosage formulation alone or in combination with one or more pharmaceutically active agent disclosed herein. In some embodiments, the one or more pharmaceutically active agents the stimulant is used in combination with include but are not limited to an antiemetic agent and a barbiturate. In specific embodiments of the invention, the stimulant is present at a dose of about 1 mg to 350 mg, about 5 mg to 25 mg, about 10 mg to 50 mg, about 25 to 100 mg, about 50 to 150 mg, about 100 mg to 250 mg, or about 75 mg to 350 mg, including in the amount of any single integer within these ranges.

An "effective amount" when used in connection with a barbiturate agent is an amount that is effective for treating or preventing pain, producing a sedative effect, anesthetic effect or calming effect when provided alone or in combination with one or more pharmaceutically active agent disclosed herein. In some embodiments, the one or more pharmaceutically active agent the barbiturate agent is used in combination with includes but is not limited to an opioid analgesic, a non-opioid analgesic, antiemetic or combination thereof. In various specific embodiments the barbiturate is present at a dose of about 1 mg to about 350 mg, about 5 mg to 25 mg, about 10 mg to 50 mg, about 25 to 100 mg, about 50 to 150 mg, about 100 mg to 250 mg, or about 75 mg to 350 mg, including in the amount of any single integer within these ranges.

An "effective amount" when used in connection with an adverse-effect agent or an opioid antagonist agent is an amount that is effective for reducing, preventing, eliminating or inhibiting or more of: (1) the capacity of the opioid analgesic agent to produce the kind of physical dependence in which withdrawal causes sufficient distress to bring about drug-seeking behavior; (2) the ability to suppress withdrawal symptoms caused by withdrawal from the opioid analgesic agent; and (3) the induction of euphoria; when provided alone or in combination with one or more pharmaceutically active agent disclosed herein. Adverse-effect agents useful in the present invention include, but are not limited to, opioid antagonists. When there is a potential for an overdose, then an antidote of the opioid analgesic agent can be used as the adverse-effect agent.

Examples of adverse-effect-reducing active agents useful in the present invention include but are not limited to promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol and propofol.

Example of opioid antagonists that can be used as an adverse-effect agent include, but are not limited to, naloxone, naltrexone, nalmefene, cyclazacine, levallorphan, or a salt thereof, and mixtures thereof. In various embodiments, the one or more pharmaceutically active agent includes but is not limited to an opioid agent, a non opioid analgesic, a stimulant, a barbiturate, or a combination thereof. In certain specific embodiments, the opioid antagonist is naloxone, naltrexone or a pharmaceutically acceptable salt thereof.

An "effective amount" when used in connection with an abuse deterrent agent is an amount that is effective for deterring non-palliative or non-therapeutic use.

An "effective amount" when used in connection with an antitussive is an amount that is effective for relieving or suppressing coughing.

An "effective amount" when used in connection with an H1 blocker is an amount that is effective for mediating a histamine response.

An "effective amount" when used in connection with an amphetamine is an amount that is effective for producing increased wakefulness or focus, or decreasing fatigue.

An "effective amount" when used in connection with a beta blocker, serotonin receptor agonist, basoconstrictor, anti-platelet agent, anti-convulsant and/or calcitonin-gene related peptide (CGRP) receptor antagonist is an amount that is effective for reducing pain or discomfort.

In some specific embodiments useful in the present invention, the opioid agent and the opioid antagonist are present in a ratio of opioid antagonist to opioid agent (analgesic) which is analgesically effective when the combination is administered orally, but which is aversive in a physically dependent subject. In this manner, the combination product (antagonist/agonist) could in essence be therapeutic to one population (patients in pain), while being unacceptable (aversive) in a different population (e.g., physically dependent subjects) when orally administered at the same dose or at a higher dose than the usually prescribed dosage, e.g., about 2-3 times the usually prescribed dose of the opioid. Thus, the oral dosage form has less potential for parenteral as well as oral abuse.

In some specific embodiments of the invention described herein, the opioid is hydrocodone or oxycodone or a salt thereof and the antagonist is naltrexone or a salt thereof, and the ratio of naltrexone or a salt thereof to hydrocodone or a salt thereof is from about 0.02-0.35:1 by weight, and in some embodiments from about 0.05-0.2:1 by weight. In one embodiment the ratio of naltrexone or a salt thereof is in an amount from about 0.5 to about 4 mg per 15 mg of hydrocodone or a salt thereof. In another embodiment the ratio of naltrexone or a salt thereof is in an amount from about 0.75 mg to about 3 mg per 15 mg hydrocodone or a salt thereof. In another example where the opioid antagonist is naltrexone or a salt thereof and the opioid agent is hydromorphone or a salt thereof, the ratio of naltrexone or a salt thereof to hydromorphone or a salt thereof can be from about 0.14:1 to about 1.19:1, or from about 0.222:1 to about 0.889:1. In another example where the opioid antagonist is naltrexone or a salt thereof and the opioid agent is oxycodone or a salt thereof, the ratio of naltrexone or a salt thereof to oxycodone or a salt thereof is about 0.03:1 to about 0.3:1, or from about 0.056:1 to about 0.222:1.

In some embodiments, an opioid antagonist is administered in an amount (i) which does not cause a reduction in the level of analgesia elicited from the dosage form upon oral administration to a non-therapeutic level and (ii) which provides at least a mildly negative, "aversive" experience in physically dependent subjects (e.g., precipitated abstinence syndrome) when the subjects attempt to take at least twice the usually prescribed dose at a time (and often 2-3 times that dose or more), as compared to a comparable dose of the opioid without the opioid antagonist present. In certain embodiments, an amount of naltrexone or a salt thereof is included in the oral dosage form and is less positively reinforcing (e.g., less "like") to a non-physically dependent opioid addict than a comparable oral dosage form without the antagonist included. In specific embodiments, the composition provides effective analgesia when orally administered.

In embodiments of the present invention in which the opioid analgesic is hydrocodone or a pharmaceutically acceptable salt thereof, the extended release oral dosage forms may include analgesic doses from about 4 mg to about 60 mg of hydrocodone or a salt thereof per dosage unit. In a controlled release oral dosage forms where hydromorphone or a salt thereof is therapeutically active opioid, it can be included in an amount from about 2 mg to about 64 mg hydromorphone hydrochloride.

In various embodiments of the present invention where the opioid analgesic is oxycodone, the controlled release oral dosage forms include from about 2.5 mg to about 800 mg oxycodone HCL. Alternatively, the dosage form may contain molar equivalent amounts of other salts of the opioids useful in compositions described herein.

In some embodiments of the invention described herein, the composition comprises an opioid analgesic agent, acetaminophen or a pharmaceutically acceptable salt thereof and promethazine or a pharmaceutically acceptable salt thereof. In some specific embodiments of the invention described herein, the composition comprises the respective agents (1) opioid analgesic agent; (2) acetaminophen or a salt thereof (3) promethazine or a pharmaceutically acceptable salt thereof in a ratio by weight of about (1 to 2):(40 to 45):(1 to 2). For example, in a specific embodiment of the invention comprising hydrocodone or oxycodone or a salt thereof, acetaminophen or a salt thereof and promethazine or a salt thereof, the ratio of amounts for each active agent is about (1):(43.33):(1.67).

In various specific embodiments of the invention disclosed herein, the composition comprises about 6-8 mg of hydrocodone or a salt thereof, 310-330 mg of acetaminophen, and 5-13 mg of promethazine or a salt thereof.

In some specific embodiments of the invention described herein, the composition comprises about 1% to 20% by weight of an antihistamine; about 10% to 80% by weight a non-opioid analgesic; and from about 1% to 20% by weight of an opioid analgesic.

In other specific embodiments of the invention, the composition comprises an effective amount of: an opioid analgesic; an antiemetic or antihistamine; and a stimulant. In these embodiments the antiemetic or antihistamine is present in an amount of about 0.5 mg to about 60 mg. In specific embodiments, the antiemetic or antihistamine is promethazine or a salt thereof.

In various embodiments, the composition comprises: an effective amount of an opioid analgesic agent; an antiemetic or antihistamine agent; and a stimulant agent or a non-opioid agent, or both. In some specific embodiments each agent is present in an amount of about 0.5 mg to 20 mg, about 5 mg to 30 mg, or about 10 mg to 100 mg.

In various embodiments of the invention disclosed herein, the composition comprises: an effective amount of an opioid analgesic, a stimulant and optionally an antiemetic or antihistamine. In some specific embodiments the relative ratio by weight of each is about (1 to 2):(40 to 45):(1 to 2).

In some embodiments the composition comprises an effective amount of an opioid; a non-opioid agent; and a barbiturate. In some specific embodiments, the opioid agent is present in a range of about 1 mg to about 200 mg, including in the amount of any single integer within this range; the non-opioid agent is present in a range of between about 200 mg to about 1000 mg, including in the amount of any single integer within this range; and the barbiturate is present at a dose between about 0.5 mg to about 200 mg, including in the amount of any single integer within this range.

In various embodiment of the invention described herein, the composition comprises an effective amount of a barbiturate agent; a non-opioid agent; and a stimulant agent. In some specific embodiments the barbiturate agent is present in a range of about 0.5 mg to about 200 mg, including in the amount of any single integer within this range; the non-opioid agent is present in a range of between about 200 mg to about 1000 mg, including in the amount of any single integer within this range; and the stimulant agent is present at a dose from about 0.5 mg to about 200 mg including in the amount of any single integer within this range.

In various embodiments of the invention disclosed herein, the composition comprises an effective amount of a barbiturate and a stimulant. In some specific embodiments the composition comprises a stimulant at a dose of about 1 mg to about 350 mg, about 5 mg to 25 mg, about 10 mg to 50 mg, about 25 to 100 mg, about 50 to 150 mg, about 100 mg to 250 mg, or about 75 mg to 350 mg, including in the amount of any single integer within these ranges. In these specific embodiments, the barbiturate agent is present in a range of about 0.5 mg to about 200 mg, including in the amount of any single integer within this range.

In various embodiments of the invention disclosed herein, the composition comprises an effective amount of a non-opioid agent and a stimulant. In specific embodiments the non-opioid agent is present in a range of between about 200 mg to about 1000 mg, including in the amount of any single integer within this range.

In various embodiments of the invention disclosed herein, the composition comprises an effective amount of propoxyphene or a salt thereof and a non-opioid agent. In some embodiments the composition further comprises an antiemetic. In some embodiments the composition further comprises a stimulant agent. In specific embodiments the propoxyphene is present in a range of about 1.0 mg to about 100 mg, including in the amount of any single integer within this range and the non-opioid agent is present in a range of about 200 mg to about 1000 mg, including in the amount of any single integer within this range.

In one embodiment, the compositions comprise: hydrocodone, oxycodone, or a pharmaceutically acceptable salt thereof, in a dosage range of from about 1.0 mg to about 200 mg; acetaminophen or a pharmaceutically acceptable salt thereof in a dosage range of from about 200 mg to about 1000 mg; and, promethazine or a pharmaceutically acceptable salt thereof in a dosage range of from about 0.5 mg to about 100 mg.

In another embodiment, a compositions comprises: oxycodone or a pharmaceutically acceptable salt thereof in a dosage range of from about 10 mg to about 80 mg; Naltrexone or a pharmaceutically acceptable salt thereof in a dosage range of from about 0.5 mg to about 0.75 mg; and, promethazine or a pharmaceutically acceptable salt thereof in a dosage range of from about 12.5 mg to about 50 mg.

In yet another embodiment, the compositions comprises: oxycodone or a pharmaceutically acceptable salt thereof in a dosage range of from about 10 mg to about 80 mg; and promethazine or a pharmaceutically acceptable salt thereof in a dosage range of from about 12.5 mg to about 50 mg. These compositions can be formulated to provide for an extended time release over a desired dosage interval, such as between 4 hours and 24 hours, including at any time within this range. In another embodiment, the compositions comprise about 7.5 mg of hydrocodone, about 325 mg of acetaminophen or a pharmaceutically acceptable salt thereof, and about 12.5 mg of promethazine or a pharmaceutically acceptable salt thereof.

In another specific embodiment, the compositions comprise about 7.5 mg of oxycodone or a pharmaceutically acceptable salt thereof, about 325 mg of acetaminophen or a pharmaceutically acceptable salt thereof, and about 12.5 mg of promethazine or a pharmaceutically acceptable salt thereof.

Exemplary Routes of Administration

In any of the embodiments disclosed herein, a composition of the invention can be administered using one or more different dosage forms which are further described herein. For example, a composition comprising multiple active agents can be administered in solid, semi-solid, microemulsion, gel, patch or liquid form. Such dosage forms are further described herein. Examples of such dosage forms are known in the art. For example, the tablet forms disclosed in U.S. Pat. Nos. 3,048,526, 3,108,046, 4,786,505, 4,919,939, 4,950,484; the gel forms disclosed in U.S. Pat. Nos. 4,904,479, 6,482,435, 6,572,871, 5,013,726; the delivery patches disclosed in U.S. Pat. Nos. 5,741,510, 4,624,665, 4,626,539, 4,834,978, 6,469,227, 5,919,479, 6,261,595, 6,303,142, 6,341,387, 6,465,006, 6,613,350, 6,780,426, 7,094,228, 6,756,053; the capsule forms disclosed in U.S. Pat. Nos. 4,800,083, 4,532,126, 4,935,243, 6,258,380; the liquid forms disclosed in U.S. Pat. Nos. 4,625,494, 4,478,822, 5,610,184; and the I.V. forms disclosed in U.S. Pat. Nos. 4,871,353, 4,925,444, 5,484,406; each of which is incorporated herein by reference in its entirety.

In various embodiments, the active agents are formulated to be administered through oral dosage forms (e.g., tablets, capsules, gels, lollipops), inhalations, nasal sprays, patches, absorbing gels, liquids, liquid tannates, suppositories, injections, I.V. drips, other delivery methods, or a combination thereof to treat subjects. Administration may be performed in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance, pulmonary delivery system commercially available from Inhale Therapeutics), vaginally, parenterally, rectally, or intraocularly.

Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents and any other inactive agents that can be included in pharmaceutical dosage forms for oral administration. Examples of such vehicles and additives can be found in Remington's Pharmaceutical Sciences, 17th edition (1985). Suitable additives useful in the present invention include, but are not limited to, diluents, disintegrants, binders, surfactants, lubricants, glidants, coating materials, plasticizers, coloring agents, flavoring agents, or pharmaceutically inert materials. Examples of these additives are provided herein.

To prepare the compositions of the present invention, an effective amount of active agents can be mixed with a suitable pharmaceutically acceptable carrier. Upon mixing of the compounds, the resulting composition can be a solid, a half-solid, a solution, suspension, or an emulsion. Such compositions can be prepared according to methods known to those skilled in the art. The forms of the resulting compositions can depend upon a variety of factors, including the intended mode of administration and the solubility of the compounds in the selected carrier or vehicle. The effective concentration of analgesics is sufficient for lessening or alleviating pain.

The dosage forms described herein can be manufactured using processes that are well known to those of skill in the art. For example, for the manufacture of bi-layered tablets, the agents can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers", can be used to increase the bulk of a tablet so that a practical size is provided for compression. Non-limiting examples of diluents include, but are not limited to, lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina or kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, cross linked polymers such as, e.g., cross linked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

Controlled-release formulations can comprise one or more combination of excipients that slow the release of the agents by coating or temporarily bonding or decreasing their solubility of the active agents. Examples of these excipients include cellulose ethers such as hydroxypropylmethylcellulose (e.g., Methocel K4M) or silicified microcrystalline cellulose; polyvinylacetate-based excipients such as, e.g., Kollidon SR; polymers and copolymers based on methacrylates and methacrylic acid such as, e.g., Eudragit NE 30D; croscarmellose sodium, magnesium stereate or stearic acid.

Immediate-release formulations can comprise one or more combination of excipients that allow for a rapid release of a pharmaceutically active agent (such as from 1 minute to 1 hour after administration), such as an anti-emetic or an antihistamine. In one embodiment an immediate release excipient can be hydroxypropylmethylcellulose, silicified microcrystalline cellulose, microcrystalline cellulose, sodium carboxymethyl cellulose, sodium starch glycolate, corn starch, colloidal silica, Sodium Laurel Sulphate, Magnesium Stearate, stearic acid, Prosolve SMCC (HD90), croscarmellose Sodium, Crospovidone NF, Avicel PH200, or combinations of such excipients.

In one embodiment of the invention, the opioid analgesic or non-opioid agents (e.g., hydrocodone or oxycodone or a salt thereof, and acetaminophen or a salt thereof) are formulated for extended or controlled-release while the promethazine or a salt thereof is formulated for immediate release. In another embodiment, all agents are formulated for extended or controlled-release.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action. As noted above, the compositions can comprise additional (e.g., a fourth, fifth, sixth, etc.) additional active agents.

In one embodiment, the compositions comprise three or more pharmaceutically active agents wherein at least one active agent is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing" which is incorporated herein in its entirety by reference.

In another embodiment diluents suitable for use in the present invention include, for example, cellulose; cellulose derivatives such as microcrystalline cellulose and the like; starch; starch derivatives such as corn starch, cyclodextrin and the like; sugar; sugar alcohol such as lactose, D-mannitol and the like; inorganic diluents such as dried aluminum hydroxide gel, precipitated calcium carbonate, magnesium aluminometasilicate, dibasic calcium phosphate and the like.

In another embodiment of binders suitable for use in the prevent invention include, for example, hydroxypropylcellulose, methylcellulose, hydroxypropylmethylcellulose, povidone, dextrin, pullulane, hydroxypropyl starch, polyvinyl alcohol, scacia, agar, gelatin, tragacanth, macrogol and the like.

In another embodiment of surfactants suitable for use in the present invention include, for example, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and the like.

In another embodiment of lubricants suitable for use in the present invention include, for example, stearic acid, calcium stearate, magnesium stearate, talc and the like.

In another embodiment of glidants suitable for use in the present invention include, for example, dried aluminum hydroxide gel, magnesium silicate and the like.

In another embodiment of coating materials suitable for use in the present invention include, for example, hydroxypropylmethyl cellulose 2910, aminoalkyl methacrylate copolymer E, polyvinylacetal diethylaminoacetate, macrogol 6000, titanium oxide and the like. Examples of plasticizers useful in the present invention include, for example, triethyl citrate, triacetin, macrogol 6000 and the like.

Exemplary Oral Formulations

In one embodiment the invention relates to methods and compositions formulated for oral delivery to a subject in need. In one embodiment a composition is formulated so as to deliver one or more pharmaceutically active agents to a subject through a mucosa layer in the mouth or esophagus. In another embodiment the composition is formulated to deliver one or more pharmaceutically active agents to a subject through a mucosa layer in the stomach and/or intestines.

In one embodiment compositions are provided in modified release dosage forms. Suitable modified release dosage vehicles include, but are not limited to, hydrophilic or hydrophobic matrix devices, water-soluble separating layer coatings, enteric coatings, osmotic devices, multi-particulate devices, and combinations thereof. The compositions may also comprise non-release controlling excipients.

In another embodiment compositions are provided in enteric coated dosage forms. These enteric coated dosage forms can also comprise non-release controlling excipients. In one embodiment the compositions are in the form of enteric-coated granules, as controlled-release capsules for oral administration. The compositions can further comprise cellulose, disodium hydrogen phosphate, hydroxypropyl cellulose, hypromellose, lactose, mannitol, or sodium lauryl sulfate. In another embodiment the compositions are in the form of enteric-coated pellets, as controlled-release capsules for oral administration. The compositions can further comprise glycerol monostearate 40-50, hydroxypropyl cellulose, hypromellose, magnesium stearate, methacrylic acid copolymer type C, polysorbate 80, sugar spheres, talc, or triethyl citrate.

In another embodiment the compositions are enteric-coated controlled-release tablets for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, or yellow ferric oxide.

In another embodiment the compositions can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

In another embodiment compositions are provided in effervescent dosage forms. These effervescent dosage forms can also comprise non-release controlling excipients.

In another embodiment compositions can be provided in a dosage form that has at least one component that can facilitate the immediate release of an active agent, and at least one component that can facilitate the controlled release of an active agent. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment compositions are provided in a dosage form for oral administration to a subject, which comprise one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

The compositions provided herein can be in unit-dosage forms or multiple-dosage forms. Unit-dosage forms, as used herein, refer to physically discrete units suitable for administration to human or non-human animal subjects and packaged individually. Each unit-dose can contain a predetermined quantity of an active ingredient(s) sufficient to produce the desired therapeutic effect, in association with the required pharmaceutical carriers or excipients. Examples of unit-dosage forms include, but are not limited to, ampoules, syringes, and individually packaged tablets and capsules.

Unit-dosage forms may be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents.

The compositions may also be formulated as a modified release dosage form, including immediate-, delayed-, extended-, prolonged-, sustained-, pulsatile-, controlled-, extended, accelerated- and fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which are herein incorporated by reference in their entirety).

Exemplary Bilayer Tablets

Figure 2:
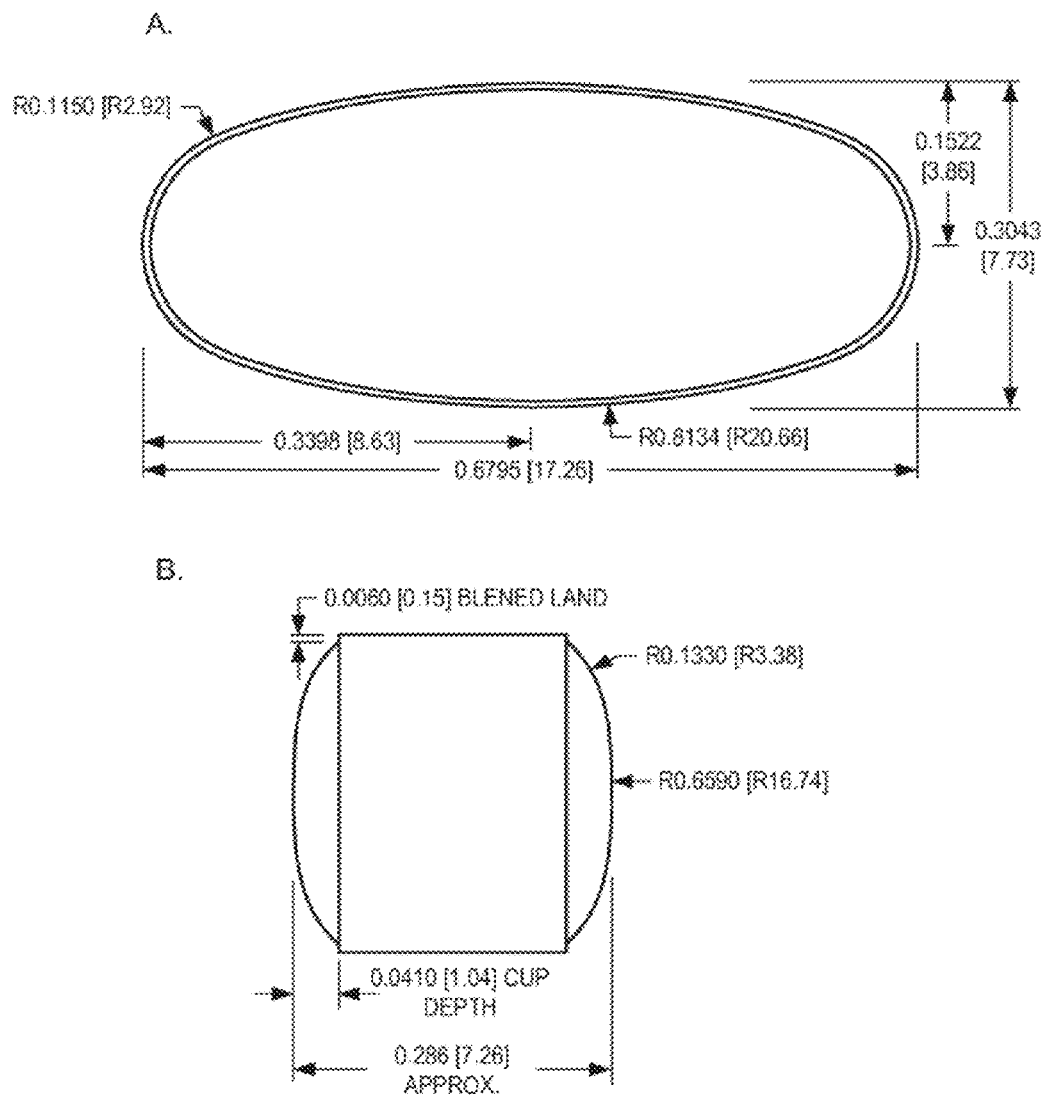
FIG. 2 illustrates one embodiment of a tablet of the invention. A. Illustrates a top view of the tablet (numerals refer to measurements in millimeters); B. illustrates a side view of the tablet.

In some embodiments, the invention described herein relates to multi-layer tablets, such as bi-layer tablets. In specific embodiments, the bi-layer tablet comprises an immediate-release layer and a controlled-release layer. A non-limiting example of a bilayer tablet of the invention is depicted in FIG. 2. In various embodiments, the tablet can be rectangular, tubular, oblong (e.g., FIG. 2), circular, oval or in a capsule form. In various embodiments, the immediate-release layer and/or the controlled-released layer include one or more pharmaceutically active agents.

In various embodiments, the bilayer tablet of the invention has a hardness of between about 7 and about 15 kilaponds (kp). In various embodiments, the bilayer tablet has a hardness of a single integer between 7 and 15 kp. In some embodiments, the bilayer table has a hardness of between about 7.1 and about 10 mm. In various embodiments, the bilayer tablet has a hardness of a single integer between 7.1 and 10 mm.

In one embodiment, the bi-layer tablet comprises an immediate-release layer and a controlled-release layer. In various embodiments, the immediate-release layer or the controlled-released layer comprises one or more pharmaceutically active agents. In one embodiment, a bilayer tablet of the invention has a hardness of about 7, 7.1, 7.2, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 kilaponds (kp). In one embodiment, the bilayer tablet has a hardness of about 9.5 kp. In a further embodiment, a bilayer tablet of the invention has a thickness of about 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 or 10 mm. It will be understood that as to the kilapond and thickness measurements, increments of 0.1 decimal points are within the scope of the invention.

In various embodiments, a bilayer tablet provides an effective amount of one or more pharmaceutically active agents for about 4-6 hours following oral administration. In some embodiment, the bilayer tablet provides an effective amount of at least one active agent for about 12 hours, about 24 hours or about 48 hours following administration. In various embodiments, the one or more pharmaceutically active agents provided in 4-6 hour, 12 hour, 24 hour or 48 hour dosing intervals. Therefore, a bilayer tablet of the invention is capable of providing any of the one or more pharmaceutically active agents disclosed herein in the foregoing dosing intervals.

In one embodiment, a composition comprises promethazine or a pharmaceutically acceptable salt thereof and about 70 to about 80% of the promethazine or pharmaceutically acceptable salt thereof dissolves in the stomach of a subject after about 5 to about 10 minutes following oral administration. In one embodiment, the promethazine is promethazine HCl.

In one embodiment, a composition comprises hydrocodone or a pharmaceutically acceptable salt thereof and about 30 to about 60% of the hydrocodone or pharmaceutically acceptable salt thereof dissolves in the stomach of a subject after about 5 to about 10 minutes following oral administration.

In one embodiment, the hydrocodone salt is hydrocodone bitartrate. In one embodiment, a composition comprises acetaminophen or a pharmaceutically acceptable salt thereof and 50% to about 70% of the acetaminophen or pharmaceutically acceptable salt thereof dissolves in the stomach of a subject after about 5 to about 10 minutes following oral administration.

In one embodiment, the composition comprises promethazine or a pharmaceutically acceptable salt thereof, hydrocodone or a pharmaceutically acceptable salt thereof and acetaminophen or a pharmaceutically acceptable salt thereof, and at least 90% of the pharmaceutically active agents in the composition dissolve in the stomach of a subject after about 45 minutes following oral administration. In one embodiment, the composition is a bilayer tablet comprising an immediate-release layer and a controlled-release layer.

In one embodiment, the immediate release layer comprises promethazine or a pharmaceutically acceptable salt as the only pharmaceutically active agent. In another embodiment, the controlled-release layer comprises hydrocodone or a pharmaceutically acceptable salt and acetaminophen or a pharmaceutically acceptable salt as the only pharmaceutical ingredients.

In yet another embodiment, the controlled release layer comprises an opioid analgesic or a non-opioid analgesic as the only pharmaceutically active agent. In another embodiment, the controlled release layer comprises an opioid analgesic and a non-opioid analgesic as the only pharmaceutically active agents. In another embodiment the immediate release layer comprises an antiemetic or a stimulant as the only pharmaceutically active agent. In another embodiment the immediate release layer comprises an antiemetic and a stimulant as the only pharmaceutically active agents.

Immediate-Release Layer

Immediate-release refers to the release of an active agent substantially immediately upon administration. In one embodiment, immediate-release results in dissolution of an agent within 1-20 minutes after entering the stomach. Dissolution can be of all or less than the entire amount of the active agent. For example, dissolution of 100% of an agent (antihistamine or antiemetic) can occur in the prescribed time. Alternatively, dissolution of less than all of the agent can occur in about 1 minute to about 20 minutes (e.g., dissolution of about 70%, about 75%, about 80%, about 85%, about 90%, about 91%, about 92%, about 93%, about 94%, about 95%, about 96%, about 97%, about 98%, about 99%, about 99.5% or 99.9% of an agent).

In one embodiment, the immediate-release layer is capable of releasing about 70 to about 80% of the one or more pharmaceutically active agent contained therein in the stomach of a subject in about 5 to about 10 minutes following oral administration. In one embodiment, the immediate-release layer is capable of releasing about 90 to about 100% of one or more pharmaceutically active agent contained therein in the stomach of a subject in about 40 minutes.

In one embodiment, the one or more pharmaceutically active agent in the immediate-release layer is an antiemetic. In one embodiment, the antiemetic is promethazine or a pharmaceutically acceptable salt thereof. In another embodiment, the antiemetic is promethazine HCl.

In one embodiment, an immediate-release layer comprises two or more agents, including an anti-emetic and a stimulant.

In some embodiment, the immediate-release layer comprises one or more excipients, including but not limited to silicified microcrystalline cellulose (e.g., HD90), croscarmellose sodium (CS, e.g. AC-Di-Sol™), magnesium stearate. In one embodiment, the total layer weight of the immediate-release layer is from about 100 to about 300 mg, such as about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg.

In one embodiment, the immediate-release layer comprises from about 75 mg to about 150 mg of silicified microcrystalline cellulose, from about 10 mg to about 20 mg croscarmellose sodium, from about 0.5 mg to 2 mg magnesium stearate. In yet a further embodiment, the immediate-release layer comprises from about 10 to about 15 mg promethazine, or a pharmaceutically acceptable salt thereof. In another embodiment, the immediate-release layer comprises about 12.5 mg promethazine or a pharmaceutically acceptable salt thereof. In another embodiment, the pharmaceutically acceptable salt is promethazine HCl. In another embodiment, the immediate-release layer comprises one or more additional pharmaceutically acceptable excipients, salts, and/or carriers disclosed herein.

In one embodiment, the immediate-release layer comprise about 12.5 mg promethazine HCl, about 121.5 mg silicified microcrystalline cellulose, about 15 mg croscarmellose sodium, and about 1 mg magnesium stearate.

In one embodiment, a composition comprising an effective amount of each of hydrocodone bitartrate, acetaminophen and promethazine HCl is capable of dissolving in the stomach of a subject so that an effective plasma concentration of each of pharmaceutically active ingredient is present in a subject in from about 5 minutes to about 30 minutes.

Controlled-Release Layer

In one embodiment, the controlled-release layer is capable of releasing about 30 to about 40% of the one or more pharmaceutically active agent contained therein in the stomach of a subject in about 5 to about 10 minutes following oral administration. In another embodiment, the controlled-release layer is capable of releasing about 90% of the one or more pharmaceutically active agents are released in about 40 minutes after oral administration.

In some embodiment, the controlled-release layer comprises one or more excipients, including but not limited to silicified microcrystalline cellulose (e.g., HD90), croscarmellose sodium (CS; e.g., AC-Di-Sol), or Magnesium stearate. In one embodiment, the total layer weight of the controlled-release layer is from about 100 to about 300 mg, such as about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg.

In one embodiment, a controlled-release layer comprises from about 75 mg to about 250 mg of silicified microcrystalline cellulose, from about 10 mg to about 40 mg hydroxyl methyl propyl cellulose, from about 0.5 mg to 5 mg magnesium stearate, and from about 0.5 mg to about 5 mg stearic acid.

In another embodiment, a controlled-release layer comprises from about 75 mg to about 250 mg of silicified microcrystalline cellulose, from about 10 mg to about 40 mg hydroxyl methyl propyl cellulose, from about 0.5 mg to 5 mg magnesium stearate, from about 5 mg to about 25 mg of croscarmellose sodium and from about 0.5 mg to about 5 mg stearic acid. In another embodiment, a controlled-release layer comprises from about 120 mg to about 170 mg of silicified microcrystalline cellulose, from about 12 mg to about 20 mg hydroxyl methyl propyl cellulose, from about 2 mg to 3.5 mg magnesium stearate, from about 8 mg to about 12 mg of croscarmellose sodium and from about 2 mg to about 3.5 mg stearic acid. In another embodiment, the controlled-release layer comprises one or more additional pharmaceutically acceptable excipients, salts, and/or carriers disclosed herein.

In another embodiment, the controlled-release layer comprises about 152 mg silicified microcrystalline cellulose, about 20 mg hydroxyl methyl propyl cellulose, about 2.75 mg magnesium stearate, about 2.75 stearic acid, about 7.5 mg hydrocodone, or a pharmaceutically acceptable salt thereof and about 325 mg acetaminophen or a pharmaceutically acceptable salt thereof. In yet a further embodiment, the controlled-release layer comprises from about 5 mg to about 12.5 mg hydrocodone or a pharmaceutically acceptable salt thereof. In one embodiment, the controlled-release layer comprises about 7.5 mg hydrocodone or a pharmaceutically acceptable salt thereof. In another embodiment, the opioid analgesic is oxycodone or a pharmaceutically acceptable salt thereof. In one embodiment, the pharmaceutically acceptable salt is oxycodone HCl. In another embodiment, the pharmaceutically acceptable salt for hydrocodone is hydrocodone bitartrate. In another embodiment, the controlled-release layer comprises one or more additional pharmaceutically acceptable excipients, salts, and/or carriers disclosed herein.

In one embodiment, the controlled-release layer comprises about 149.5 mg silicified microcrystalline cellulose, about 15.5 mg hydroxyl methyl propyl cellulose, about 2.7 mg magnesium stearate, about 2.7 stearic acid, about 7.5 mg hydrocodone, or a pharmaceutically acceptable salt thereof, about 10 mg croscarmellose sodium, and about 325 mg acetaminophen or a pharmaceutically acceptable salt thereof. In yet a further embodiment, the controlled-release layer comprises from about 5 mg to about 12.5 mg hydrocodone or a pharmaceutically acceptable salt thereof. In one embodiment, the controlled-release layer comprises about 7.5 mg hydrocodone or a pharmaceutically acceptable salt thereof. In another embodiment, the opioid analgesic is oxycodone or a pharmaceutically acceptable salt thereof. In one embodiment, the pharmaceutically acceptable salt is oxycodone HCl. In another embodiment, the pharmaceutically acceptable salt for hydrocodone is hydrocodone bitartrate. In another embodiment, the controlled-release layer comprises one or more additional pharmaceutically acceptable excipients, salts, and/or carriers disclosed herein.

In yet a further embodiment, the controlled-release layer further comprises from about 250 mg to about 402 mg acetaminophen or a pharmaceutically acceptable salt thereof. In one embodiment the controlled-release layer comprises about 325 mg acetaminophen or a pharmaceutically acceptable salt thereof.

In one embodiment, the immediate-release layer comprises promethazine HCl and the controlled-release layer comprises hydrocodone bitartrate. In another embodiment, the controlled-release layer further comprises a non-opioid analgesic (e.g., acetaminophen).

In one embodiment, the one or more pharmaceutically active agents of the controlled-release layer is an opioid analgesic. In one embodiment, the opioid analgesic is hydrocodone or oxycodone; or a pharmaceutically acceptable salt thereof. In one embodiment, the immediate-release layer is about 150 mg in total layer weight and the controlled-release layer is about 550 mg total weight.

Furthermore, in one embodiment, the controlled-release layer comprises about 325 mg acetaminophen, about 7.5 mg hydrocodone bitartrate, about 152 mg silicified microcrystalline cellulose, about 20 mg hydroxyl methyl propyl cellulose (HPMC), about 2.75 mg magnesium stearate, and about 2.75 mg stearic acid; and the immediate-release layer comprises about 12.5 mg promethazine HCl, about 121 mg silicified microcrystalline cellulose, about 15 mg croscarmellose sodium, and about 1 mg magnesium stearate. In another embodiment, one or both of the immediate-release layer and the controlled-release layer comprises one or more additional pharmaceutically acceptable excipients, salts, and/or carriers disclosed herein.

In another embodiment, the controlled-release layer comprises about 325 mg acetaminophen, about 7.5 mg hydrocodone bitartrate, about 149.5 mg silicified microcrystalline cellulose, about 15.5 mg hydroxyl methyl propyl cellulose (HPMC), about 10 mg croscarmellose sodium, about 2.7 mg magnesium stearate, and about 2.7 mg stearic acid; and the immediate-release layer comprises about 12.5 mg promethazine HCl, about 121.5 mg silicified microcrystalline cellulose, about 15 mg croscarmellose sodium, and about 1 mg magnesium stearate. In another embodiment, one or both of the immediate-release layer and the controlled-release layer comprises one or more additional pharmaceutically acceptable excipients, salts, and/or carriers disclosed herein.

In another embodiment, the controlled-release layer comprises about 325 mg acetaminophen, about 7.5 mg hydrocodone bitartrate, about 149.5 mg silicified microcrystalline cellulose, about 15.6 mg hydroxyl methyl propyl cellulose (HPMC), about 10 mg croscarmellose sodium, about 2.7 mg magnesium stearate, and about 2.7 mg stearic acid; and the immediate-release layer comprises about 12.5 mg promethazine HCl, about 121.5 mg silicified microcrystalline cellulose, about 15 mg croscarmellose sodium, and about 1 mg magnesium stearate. In another embodiment, one or both of the immediate-release layer and the controlled-release layer comprises one or more additional pharmaceutically acceptable excipients, salts, and/or carriers disclosed herein.

In another embodiment, the controlled-release layer comprises about 325 mg acetaminophen, about 7.5 mg hydrocodone bitartrate, about 149.5 mg silicified microcrystalline cellulose, about 15.7 mg hydroxyl methyl propyl cellulose (HPMC), about 10 mg croscarmellose sodium, about 2.7 mg magnesium stearate, and about 2.7 mg stearic acid; and the immediate-release layer comprises about 12.5 mg promethazine HCl, about 121.5 mg silicified microcrystalline cellulose, about 15 mg croscarmellose sodium, and about 1 mg magnesium stearate. In another embodiment, one or both of the immediate-release layer and the controlled-release layer comprises one or more additional pharmaceutically acceptable excipients, salts, and/or carriers disclosed herein.

In another embodiment, the controlled-release layer comprises about 325 mg acetaminophen, about 7.5 mg hydrocodone bitartrate, about 149.5 mg silicified microcrystalline cellulose, about 15.8 mg hydroxyl methyl propyl cellulose (HPMC), about 10 mg croscarmellose sodium, about 2.7 mg magnesium stearate, and about 2.7 mg stearic acid; and the immediate-release layer comprises about 12.5 mg promethazine HCl, about 121.5 mg silicified microcrystalline cellulose, about 15 mg croscarmellose sodium, and about 1 mg magnesium stearate. In another embodiment, one or both of the immediate-release layer and the controlled-release layer comprises one or more additional pharmaceutically acceptable excipients, salts, and/or carriers disclosed herein.

In another embodiment, a controlled release layer comprises about 0.1 mg to about 20 mg of HPMC, including in the amount of any single integer within this range. In another embodiment a controlled release layer comprises about 15 mg to about 16 mg of HPMC. In another embodiment a controlled release layer comprises about 15.5 mg of HPMC. In another embodiment a controlled release layer comprises about 15.6 mg of HPMC. In another embodiment a controlled release layer comprises about 15.7 mg of HPMC. In another embodiment a controlled release layer comprises about 15.8 mg of HPMC. In one embodiment the HPMC is Hypromellose 2906 (e.g., Hypromellose 2906 F), Hypromellose 2910 (Hypromellose 2910 E3), or Hypromellose 2208 (Hypromellose 2208 K4). In another embodiment the HPMC is Hypromellose 2208 (Hypromellose 2208 K4).

In another embodiment, a controlled release layer comprises about 0.1 mg to 20 mg of croscarmellose sodium, including in the amount of any single integer within this range. In another embodiment a controlled release layer comprises about 9 mg to about 11 mg of croscarmellose sodium. In another embodiment a controlled release layer comprises about 9.9 mg of croscarmellose sodium. In another embodiment a controlled release layer comprises about 10 mg of croscarmellose sodium. In another embodiment a controlled release layer comprises about 10.1 mg of croscarmellose sodium. In another embodiment a controlled release layer comprises about 10.2 mg of croscarmellose sodium.

In another embodiment, a controlled release layer comprises about 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg or 20 mg of croscarmellose sodium.

In one embodiment, a stimulant is present in the immediate-release layer, controlled-release layer or both layers; the immediate-release layer comprises one or more antiemetic or antihistamines; and the controlled-release layer comprises one or more non-opioid analgesics. In addition, either layer of the bi-layered tablet can comprise one or more anti-abuse agents disclosed herein.

In one embodiment, a bilayer tablet of the invention comprises a controlled-release layer comprising one or more analgesic agents as the only pharmaceutically active agents in the controlled-release layer. In another embodiment, a bilayer tablet of the invention comprises an immediate-release layer comprising an antiemetic agent as the only pharmaceutically active agent in the immediate-release layer.

In another embodiment the controlled release layer further comprises one or more of: silicified microcrystalline cellulose, hydroxy methyl propyl cellulose, croscarmellose sodium, magnesium stearate, and stearic acid. In another embodiment the immediate-release layer further comprises one or more of: silicified microcrystalline cellulose, croscarmellose sodium and magnesium stearate. In another embodiment the tablet has a hardness of about 9.5 kilopond and thickness from about 6.9 to about 7.0 mm. In another embodiment the hydrocodone salt is hydrocodone bitartrate. In another embodiment the promethazine salt is promethazine HCL. In another embodiment the controlled release layer is an inner layer and wherein the immediate-release layer is an outer layer.

In one embodiment the opioid analgesic is oxycodone or pharmaceutically acceptable salt thereof and the one or more antiemetic is promethazine or a pharmaceutically acceptable salt thereof. In another embodiment the effective amount is an amount effective for treating or preventing pain for a period of about 12 hours immediately following administration to a subject. In another embodiment the bi-layer tablet comprises an immediate release layer and a controlled release layer. In another embodiment the immediate release layer comprises the promethazine or pharmaceutically acceptable salt thereof, and wherein the controlled release layer comprises the oxycodone, or a pharmaceutically acceptable salt thereof. In another embodiment about 70% of the promethazine or pharmaceutically acceptable salt thereof is capable of dissolving in a liquid solution in about 5 minutes after contact with the solution, and wherein about 30% of the oxycodone or pharmaceutically acceptable salt is capable of dissolving in a liquid solution in about 10 minutes after contact with the solution. In another embodiment the controlled release layer further comprises an antiemetic agent.

In one embodiment the effective amount of the hydrocodone or pharmaceutically acceptable salt thereof is an amount effective for treating or preventing pain for a period of about 12 hours immediately following administration to a subject. In another embodiment the controlled release layer comprises about 7.5 mg of hydrocodone or a pharmaceutically acceptable salt thereof, about 325 mg of acetaminophen or a pharmaceutically acceptable salt thereof, about 152 mg of silicified microcrystalline cellulose, about 20 mg of hydroxy methyl propyl cellulose, about 2.7 mg of magnesium stearate, and about 2.7 mg of stearic acid; and the immediate release layer comprises about 12.5 mg of promethazine or a pharmaceutically acceptable salt thereof, about 121.5 mg of silicified microcrystalline cellulose, about 15 mg of croscarmellose sodium and about 1 mg of magnesium stearate. In another embodiment, one or both of the immediate-release layer and the controlled-release layer comprises one or more additional pharmaceutically acceptable excipients, salts, and/or carriers disclosed herein.

In another embodiment the effective amount of the hydrocodone or pharmaceutically acceptable salt thereof is an amount effective for treating or preventing pain for a period of about 12 hours immediately following administration to a subject. In another embodiment the controlled release layer comprises about 7.5 mg of hydrocodone or a pharmaceutically acceptable salt thereof, about 325 mg of acetaminophen or a pharmaceutically acceptable salt thereof, about 149.5 mg of silicified microcrystalline cellulose, about 15.5 mg of hydroxy methyl propyl cellulose, about 10 mg of croscarmellose sodium, about 2.7 mg of magnesium stearate, and about 2.7 mg of stearic acid; and the immediate release layer comprises about 12.5 mg of promethazine or a pharmaceutically acceptable salt thereof, about 121.5 mg of silicified microcrystalline cellulose, about 15 mg of croscarmellose sodium and about 1 mg of magnesium stearate. In another embodiment, one or both of the immediate-release layer and the controlled-release layer comprises one or more additional pharmaceutically acceptable excipients, salts, and/or carriers disclosed herein.

In another embodiment the composition further comprises an effective amount of naltrexone or a pharmaceutically acceptable salt thereof. In another embodiment the composition is in the form of a bi-layer tablet. In another embodiment the effective amount of the morphine or pharmaceutically acceptable salt thereof is an amount effective for treating or preventing pain for a period of about 12 hours immediately following administration to a subject.

In one embodiment the controlled release layer comprises about 7.5 mg of hydrocodone or a pharmaceutically acceptable salt thereof, and about 325 mg of acetaminophen or a pharmaceutically acceptable salt thereof; and further wherein the immediate-release layer comprises about 12 mg of promethazine or a pharmaceutically acceptable salt thereof. In another embodiment, one or both of the immediate-release layer and the controlled-release layer comprises one or more pharmaceutically acceptable excipients, salts, and/or carriers disclosed herein.

In another embodiment the controlled release layer comprises about 7.5 mg of hydrocodone or a pharmaceutically acceptable salt thereof, and about 325 mg of acetaminophen or a pharmaceutically acceptable salt thereof; and further wherein the immediate-release layer comprises about 12.5 mg of promethazine or a pharmaceutically acceptable salt thereof. In another embodiment, one or both of the immediate-release layer and the controlled-release layer comprises one or more pharmaceutically acceptable excipients, salts, and/or carriers disclosed herein.

In one embodiment the effective amount is an amount effective for treating or preventing pain for a period of about 12 hours immediately following administration to a subject.

In one embodiment the effective amount of the oxycodone or pharmaceutically acceptable salt thereof is an amount effective for treating or preventing pain for a period of about 12 hours immediately following administration to a subject.

In another embodiment a composition comprises an antiemetic and about 70 to about 80% of the antiemetic dissolves in the stomach of a subject after about 5 to about 10 minutes following oral administration. In one embodiment, about 100% of the antiemetic dissolves in the stomach of a subject about 40, about 50 or about 60 minutes following oral administration. In one embodiment, the antiemetic is promethazine or a pharmaceutically acceptable salt thereof. In another embodiment, the promethazine salt is promethazine HCl.

In another embodiment a composition comprises an opioid analgesic and from about 30% to about 40% of the opioid analgesic dissolves in the stomach of a subject after about 5 to about 10 minutes following oral administration. In one embodiment, about 100% of the opioid analgesic dissolves in the stomach of a subject about 40, about 50 or about 60 minutes following oral administration. In one embodiment, the opioid analgesic is hydrocodone, oxycodone or a pharmaceutically acceptable salt thereof. In another embodiment, the hydrocodone salt is hydrocodone bitartrate; or the oxycodone salt is oxycodone HCl.

In one embodiment, compositions described herein are administered to a subject at about every 4 to about 6 hours, about every 8 hours, about every 12 hours, or about every 24 hours. In one embodiment, a composition of the invention is administered once daily.

In one embodiment, the agent that reduces or eliminates an adverse effect is an antiemetic agent or antihistamine. In further embodiments, the adverse effect reduced or eliminated is associated with an opioid analgesic. In an additional embodiment, the adverse effect is associated with a non-opioid analgesic.

In various embodiments, an agent that reduces or eliminates an adverse effect of an opioid analgesic agent or a non-opioid analgesic agent includes but is not limited to promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol, and propofol or a pharmaceutically acceptable salt thereof.

In specific embodiments, a non-opioid analgesic agent is acetaminophen, ibuprofen, naproxen or flubiprofen, or a pharmaceutically acceptable salt thereof. In one embodiment the agent is naproxen sodium or magnesium.

In specific embodiments, the opioid analgesic agent is hydrocodone or oxycodone, or a pharmaceutically acceptable salt thereof thiosemicarbazone, p-nitrophenylhydrazone, o-methyloxime, semicarbazone, or bis (methylcarbamate) derivative, (each of the foregoing being an opioid analgesic agent or derivative). In a further embodiment, the opioid analgesic agent is hydrocodone bitartrate or oxycodone hydrochloride.

In other specific embodiments, the opioid analgesic agent is a naturally occurring opiate, such as an alkaloid occurring in the opium poppy. In one embodiment the naturally occurring opiate is morphine, codeine, narcotine, papaverine, narceine, thebaine; or a pharmaceutically acceptable salt thereof.

In one embodiment, a composition comprises an effective amount of each of an opioid analgesic, a non-opioid analgesic and an antiemetic or antihistamine, wherein the composition is capable of providing an effective plasma concentration of the antihistamine prior to an effective plasma concentrations of the opioid and the non-opioid analgesic, post oral administration. For example, a composition comprising an effective amount of each of an opioid analgesic, non-opioid analgesic, and an antihistamine or antiemetic— provides an effective plasma concentration of the latter antihistamine or antiemetic in about 1 to about 20 minutes, which is substantially earlier than effective plasma concentration of an analgesic, which can be from about 20 minutes to about 12 hours. In one embodiment of the invention, a composition comprises an effective amount of each of one or more pharmaceutically active agents disclosed herein. In one embodiment, the composition is a bilayer tablet comprising a controlled-release layer and an immediate-release layer.

In one embodiment about 70% to about 80% of a pharmaceutically active agent is capable of achieving dissolution from the immediate-release layer at about 5 to about 10 minutes following oral administration. In another embodiment about 70% to about 80% of a pharmaceutically active agent is capable of achieving dissolution from the immediate-release layer at about 5 to about 10 minutes following contact with a dissolution fluid, such as the dissolution fluid described in Example 15.

In another embodiment about 100% of a pharmaceutically active agent is capable of achieving dissolution from the immediate-release layer at about 40 minutes following oral administration. In another embodiment about 100% to of a pharmaceutically active agent is capable of achieving dissolution from the immediate-release layer at about 40 minutes following contact with a dissolution fluid, such as the dissolution fluid described in Example 15.

In another embodiment about 30% to about 40% of a pharmaceutically active agent is capable of achieving dissolution from the controlled-release layer at about 5 to about 10 minutes following oral administration. In another embodiment about 30% to about 40% of a pharmaceutically active agent is capable of achieving dissolution from the controlled-release layer at about 5 to about 10 minutes following contact with a dissolution fluid, such as the dissolution fluid described in Example 15.

In another embodiment about 90% of a pharmaceutically active agent is capable of achieving dissolution from the controlled-release layer at about 60 minutes following oral administration. In another embodiment about 90% of a pharmaceutically active agent is capable of achieving dissolution from the controlled-release layer at about 60 minutes following contact with a dissolution fluid, such as the dissolution fluid described in Example 15.

In yet another embodiment, from about 90 to about 100% of a pharmaceutically active agent is capable of achieving dissolution from the immediate-release layer at about 40, about 50 or about 60 minutes following oral administration. In yet another embodiment, from about 90 to about 100% of a pharmaceutically active agent is capable of achieving dissolution from the immediate-release layer at about 40, about 50 or about 60 minutes following contact with a dissolution fluid, such as the dissolution fluid described in Example 15.

Figure 5:
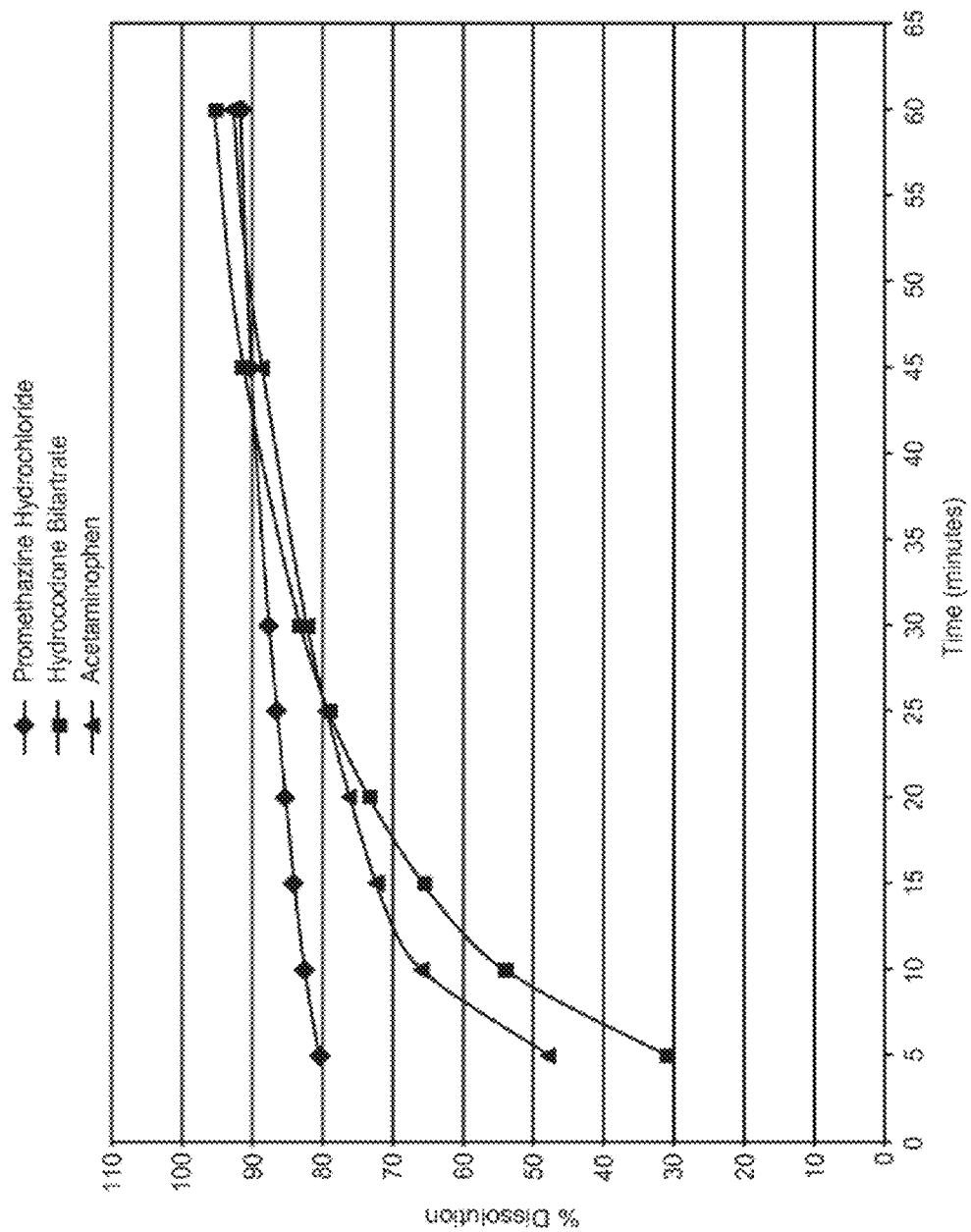
FIG. 5 illustrates an example of dissolution release profile for analgesic composition F.2 of Example 13.

In yet another embodiment, from about 90 to about 100% of a pharmaceutically active agent is capable of achieving dissolution from the controlled-release layer at about 40, about 50 or about 60 minutes following oral administration. In yet another embodiment, from about 90 to about 100% of a pharmaceutically active agent is capable of achieving dissolution from the controlled-release layer at about 40, about 50 or about 60 minutes following contact with a dissolution fluid, such as the dissolution fluid described in Example 15. An illustrative dissolution profile for the analgesic composition F.2 of Example 13 is depicted in FIG. 5.

For example, in various embodiments compositions are provided that comprise an opioid analgesic agent that is present at from about a dose of about 1.0 mg to about 100 mg, including but not limited to 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, or 100 mg. In one embodiment the opioid analgesic agent is hydrocodone or oxycodone or salt thereof. In another embodiment the opioid analgesic agent is present in a bi-layer tablet that comprises an immediate release and a controlled release layer.

In another embodiment a composition is provided that comprises a non-opioid analgesic (such as acetaminophen) that is present at a dose from about 200 mg to about 1000 mg, including but not limited to 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In one embodiment the non-opioid analgesic agent is present in a bi-layer tablet that comprises an immediate release and a controlled release layer.

In another embodiment compositions comprise an antiemetic or antihistamine agent (e.g., promethazine or a pharmaceutically acceptable salt thereof) present at a dose from about 0.5 mg to about 200 mg of, including but not limited to 0.5 mg, 1.0 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment the antiemetic or antihistamine agent is present in a bi-layer tablet that comprises an immediate release and a controlled release layer.

In one embodiment, compositions described herein comprise an opioid analgesic agent (such as hydrocodone), a pharmaceutically acceptable salt or its thiosemicarbazone, p-nitrophenylhydrazone, o-methyloxime, semicarbazone, or bis(methylcarbamate), (each of the foregoing being a hydrocodone agent, an opioid analgesic agent or derivative); acetaminophen; and promethazine or salt thereof. Furthermore, the opioid analgesic agent can be present in a range of from about 1.0 mg to about 100 mg, including but not limited to 1 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, or 100 mg.). In one embodiment, the opioid analgesic agent is hydrocodone bitartrate or oxycodone hydrochloride.

Furthermore, in various embodiments, compositions described herein comprise acetaminophen or a pharmaceutically acceptable salt thereof is present in the composition at a range of from about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In addition, the promethazine or salt thereof is present in the composition at a dose between about 0.5 mg to about 200 mg, including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment hydrocodone or a salt thereof, acetaminophen or a salt thereof, and promethazine or a salt thereof are present in a bi-layer tablet that comprises an immediate release and a controlled release layer. In another embodiment the immediate release layer comprises promethazine or a salt thereof and the controlled release layer comprises hydrocodone or a salt thereof and acetaminophen or a salt thereof.

In various embodiments, compositions described herein comprise an opioid analgesic agent (such as hydrocodone or oxycodone or a pharmaceutically acceptable salt thereof), acetaminophen or a pharmaceutically acceptable salt thereof and promethazine or a pharmaceutically acceptable salt thereof, wherein the composition comprises the respective agents, opioid analgesic agent: acetaminophen or a salt thereof: promethazine or a pharmaceutically acceptable salt thereof in a ratio by weight of about (1 to 2):(40 to 45):(1 to 2), such as about 1:40:1, 1:40:1.1, 1:40:1.2, 1:40:1.3, 1:40:1.4, 1:40:1.5, 1:40:1.6, 1:40:1.7, 1:40:1.8, 1:40:1.9, 1:40:2, 1.1:40:1, 1.2:40:1, 1.3:40:1, 1.4:40:1, 1.5:40:1, 1.6:40:1, 1.7:40:1, 1.8:40:1, 1.9:40:1, 2:40:1, 1:41:1, 1:41:1.1, 1:41:1.2, 1:41:1.3, 1:41:1.4, 1:41:1.5, 1:41:1.6, 1:41:1.7, 1:41:1.8, 1:41:1.9, 1:41:2, 1.1:41:1, 1.2:41:1, 1.3:41:1, 1.4:41:1, 1.5:41:1, 1.6:41:1, 1.7:41:1, 1.8:41:1, 1.9:41:1, 2:41:1, 1:42:1, 1:42:1.1, 1:42:1.2, 1:42:1.3, 1:42:1.4, 1:42:1.5, 1:42:1.6, 1:42:1.7, 1:42:1.8, 1:42:1.9, 1:42:2, 1.1:42:1, 1.2:42:1, 1.3:42:1, 1.4:42:1, 1.5:42:1, 1.6:42:1, 1.7:42:1, 1.8:42:1, 1.9:42:1, 2:42:1, 1:43:1, 1:43:1.1, 1:43:1.2, 1:43:1.3, 1:43:1.4, 1:43:1.5, 1:43:1.6, 1:43:1.7, 1:43:1.8, 1:43:1.9, 1:43:2, 1.1:43:1, 1.2:43:1, 1.3:43:1, 1.4:43:1, 1.5:43:1, 1.6:43:1, 1.7:43:1, 1.8:43:1, 1.9:43:1, 2:43:1, 1:43.1:1, 1:43.1:1.1, 1:43.1:1.2, 1:43.1:1.3, 1:43.1:1.4, 1:43.1:1.5, 1:43.1:1.6, 1:43.1:1.7, 1:43.1:1.8, 1:43.1:1.9, 1:43.1:2, 1.1:43.1:1, 1.2:43.1:1, 1.3:43.1:1, 1.4:43.1:1, 1.5:43.1:1, 1.6:43.1:1, 1.7:43.1:1, 1.8:43.1:1, 1.9:43.1:1, 2:43.1:1, 1:43.2:1, 1:43.2:1.1, 1:43.2:1.2, 1:43.2:1.3, 1:43.2:1.4, 1:43.2:1.5, 1:43.2:1.6, 1:43.2:1.7, 1:43.2:1.8, 1:43.2:1.9, 1:43.2:2, 1.1:43.2:1, 1.2:43.2:1, 1.3:43.2:1, 1.4:43.2:1, 1.5:43.2:1, 1.6:43.2:1, 1.7:43.2:1, 1.8:43.2:1, 1.9:43.2:1, 2:43.2:1, 1:43.3:1, 1:43.3:1.1, 1:43.3:1.2, 1:43.3:1.3, 1:43.3:1.4, 1:43.3:1.5, 1:43.3:1.6, 1:43.3:1.7, 1:43.3:1.8, 1:43.3:1.9, 1:43.3:2, 1.1:43.3:1, 1.2:43.3:1, 1.3:43.3:1, 1.4:43.3:1, 1.5:43.3:1, 1.6:43.3:1, 1.7:43.3:1, 1.8:43.3:1, 1.9:43.3:1, 2:43.3:1, 1:43.4:1, 1:43.4:1.1, 1:43.4:1.2, 1:43.4:1.3, 1:43.4:1.4, 1:43.4:1.5, 1:43.4:1.6, 1:43.4:1.7, 1:43.4:1.8, 1:43.4:1.9, 1:43.4:2, 1.1:43.4:1, 1.2:43.4:1, 1.3:43.4:1, 1.4:43.4:1, 1.5:43.4:1, 1.6:43.4:1, 1.7:43.4:1, 1.8:43.4:1, 1.9:43.4:1, 2:43.4:1, 1:43.5:1, 1:43.5:1.1, 1:43.5:1.2, 1:43.5:1.3, 1:43.5:1.4, 1:43.5:1.5, 1:43.5:1.6, 1:43.5:1.7, 1:43.5:1.8, 1:43.5:1.9, 1:43.5:2, 1.1:43.5:1, 1.2:43.5:1, 1.3:43.5:1, 1.4:43.5:1, 1.5:43.5:1, 1.6:43.5:1, 1.7:43.5:1, 1.8:43.5:1, 1.9:43.5:1, 2:43.5:1, 1:43.6:1, 1:43.6:1.1, 1:43.6:1.2, 1:43.6:1.3, 1:43.6:1.4, 1:43.6:1.5, 1:43.6:1.6, 1:43.6:1.7, 1:43.6:1.8, 1:43.6:1.9, 1:43.6:2, 1.1:43.6:1, 1.2:43.6:1, 1.3:43.6:1, 1.4:43.6:1, 1.5:43.6:1, 1.6:43.6:1, 1.7:43.6:1, 1.8:43.6:1, 1.9:43.6:1, 2:43.6:1, 1:43.7:1, 1:43.7:1.1, 1:43.7:1.2, 1:43.7:1.3, 1:43.7:1.4, 1:43.7:1.5, 1:43.7:1.6, 1:43.7:1.7, 1:43.7:1.8, 1:43.7:1.9, 1:43.7:2, 1.1:43.7:1, 1.2:43.7:1, 1.3:43.7:1, 1.4:43.7:1, 1.5:43.7:1, 1.6:43.7:1, 1.7:43.7:1, 1.8:43.7:1, 1.9:43.7:1, 2:43.7:1, 1:43.8:1, 1:43.8:1.1, 1:43.8:1.2, 1:43.8:1.3, 1:43.8:1.4, 1:43.8:1.5, 1:43.8:1.6, 1:43.8:1.7, 1:43.8:1.8, 1:43.8:1.9, 1:43.8:2, 1.1:43.8:1, 1.2:43.8:1, 1.3:43.8:1, 1.4:43.8:1, 1.5:43.8:1, 1.6:43.8:1, 1.7:43.8:1, 1.8:43.8:1, 1.9:43.8:1, 2:43.8:1, 1:43.9:1, 1:43.9:1.1, 1:43.9:1.2, 1:43.9:1.3, 1:43.9:1.4, 1:43.9:1.5, 1:43.9:1.6, 1:43.9:1.7, 1:43.9:1.8, 1:43.9:1.9, 1:43.9:2, 1.1:43.9:1, 1.2:43.9:1, 1.3:43.9:1, 1.4:43.9:1, 1.5:43.9:1, 1.6:43.9:1, 1.7:43.9:1, 1.8:43.9:1, 1.9:43.9:1, 2:43.9:1, 1:44:1, 1:44:1.1, 1:44:1.2, 1:44:1.3, 1:44:1.4, 1:44:1.5, 1:44:1.6, 1:44:1.7, 1:44:1.8, 1:44:1.9, 1:44:2, 1.1:44:1, 1.2:44:1, 1.3:44:1, 1.4:44:1, 1.5:44:1, 1.6:44:1, 1.7:44:1, 1.8:44:1, 1.9:44:1, 2:44:1, 1:45:1, 1:45:1.1, 1:45:1.2, 1:45:1.3, 1:45:1.4, 1:45:1.5, 1:45:1.6, 1:45:1.7, 1:45:1.8, 1:45:1.9, 1:45:2, 1.1:45:1, 1.2:45:1, 1.3:45:1, 1.4:45:1, 1.5:45:1, 1.6:45:1, 1.7:45:1, 1.8:45:1, 1.9:45:1, or 2:45:1. For example, in one embodiment, the ratio of amounts for each active agent is about (1):(43.33):(1.67) for hydrocodone or a salt thereof: acetaminophen or a salt thereof: promethazine or a pharmaceutically acceptable salt thereof, respectively. In one embodiment a pharmaceutically acceptable salt of hydrocodone, acetaminophen or promethazine is provided. In one embodiment an opioid analgesic agent (such as hydrocodone or oxycodone or a salt thereof), acetaminophen or a salt thereof and promethazine or a salt thereof are present in a bi-layer tablet that comprises an immediate release and a controlled release layer.

In another embodiment, the composition comprises oxycodone, a pharmaceutically acceptable salt or its thiosemicarbazone, p-nitrophenylhydrazone, o-methyloxime, semicarbazone, or bis (methylcarbamate) (each of the foregoing being a hydrocodone agent or derivative); acetaminophen or a salt thereof and promethazine or a salt thereof. Furthermore, the oxycodone or a salt thereof is present in a range of about 1 mg to about 200 mg, including but not limited to 1.0 mg, 1.5 mg, 2.5 mg, 3.0 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg, 30 mg, 40 mg, 50 mg, 70 mg, 100 mg, 130 mg, 160, 190 mg, 200 mg. Furthermore, the acetaminophen or a salt thereof is in a range of between about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. The compositions can further comprise between about 0.5 mg to about 200 mg of an antihistamine (e.g., promethazine or a salt thereof), including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment oxycodone or a salt thereof, acetaminophen or a salt thereof and promethazine or a salt thereof are present in a bi-layer tablet that comprises an immediate release and a controlled release layer.

In one embodiment, the composition comprises promethazine or a salt thereof in an amount of 12.5 mg. In one embodiment, the compositions described herein comprise oxycodone or a salt thereof, acetaminophen or a salt thereof and promethazine or a salt thereof, wherein the composition comprises the agents in a weight ratio of about (1 to 2):(40 to 45):(1 to 2), respectively. In one embodiment a pharmaceutically acceptable salt of oxycodone, acetaminophen or promethazine is provided. For example, in one embodiment, the weight ratio of amounts for each active agent is about (1):(43.33):(1.67) for oxycodone or a salt thereof, acetaminophen or a salt thereof and promethazine or a salt thereof, respectively. In one embodiment, the compositions described herein comprise an antihistamine (e.g., promethazine or a salt thereof) at a lower dosage than that which the antihistamine is administered alone. In one embodiment, the antihistamine is provided in the composition at a dosage to prevent sedation, which may be observed with relatively higher dosages of promethazine or a salt thereof. Thus in some embodiments, promethazine is provided at 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. Therefore, an antihistamine or antiemetic (e.g., promethazine or a salt thereof) can be provided at a dosage that is effective for reducing adverse affects associated with the opioid analgesic or non-opioid analgesic, but is at a relative low enough dosage (e.g., given the subject's weight) to prevent sedation associated with the antihistamine or antiemetic. Examples of adverse effects include acute liver toxicity, allergic reactions such as swelling, difficulty breathing, closing of throat, abdominal pain, nausea, unusual bleeding or bruising. In one embodiment oxycodone or a salt thereof, acetaminophen or a salt thereof; and promethazine or a salt thereof are present in a bi-layer tablet that comprises an immediate release and a controlled release layer.

In one embodiment, the compositions described herein comprise 6-8 mg of hydrocodone or a salt thereof (such as about 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, or 8.0 mg), 310-330 mg of acetaminophen (such as about 310 mg, 315 mg, 320 mg, or 325 mg), and 5-13 mg of promethazine or a salt thereof (such as about 10 mg, 10.5 mg, 11.0 mg, 11.5 mg, 12.0 mg, 12.5 mg, 13.0, mg, 13.5 mg, 14.0 mg, 14.5 mg, or 15 mg). In a further embodiment a pharmaceutically acceptable salt of hydrocodone, acetaminophen or promethazine is provided. The hydrocodone and the acetaminophen can be formulated using conventional technologies to provide for an extended time release over a desired dosage interval. All or some of the promethazine can be formulated for immediate release to help abate common adverse effects associated with the hydrocodone and acetaminophen including nausea, vomiting, other gastric upsets, skin rashes, allergic reactions such as swelling, difficulty breathing, closing of throat, abdominal pain, unusual bleeding or bruising, sedation, CNS depression, or respiratory depression. In one embodiment hydrocodone, acetaminophen; and promethazine are present in a bi-layer tablet that comprises an immediate release and a controlled release layer.

In one embodiment, the compositions described herein comprise from 1% to 20% by weight of an antihistamine (such as 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%); from 10% to 80% by weight a non-opioid analgesic (such as 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, 49.5%, 50%, 50.5%, 51%, 51.5%, 52%, 52.5%, 53%, 53.5%, 54%, 54.5%, 55%, 55.5%, 56%, 56.5%, 57%, 57.5%, 58%, 58.5%, 59%, 59.5%, 60%, 60.5%, 61%, 61.5%, 62%, 62.5%, 63%, 63.5%, 64%, 64.5%, 65%, 65.5%, 66%, 66.5%, 67%, 67.5%, 68%, 68.5%, 69%, 69.5%, 70%, 70.5%, 71%, 71.5%, 72%, 72.5%, 73%, 73.5%, 74%, 74.5%, 75%, 75.5%, 76%, 76.5%, 77%, 77.5%, 78%, 78.5%, 79%, 79.5%, 80%); and from 1% to 20% by weight of an opioid analgesic (such as 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%). In one embodiment an opioid analgesic agent, a non-opioid analgesic and an antihistamine are present in a bi-layer tablet that comprises an immediate release and a controlled release layer.

In one embodiment, the compositions described herein comprise 6-8 mg of oxycodone HCL (such as about 7.5 mg), 250-402 mg of acetaminophen (such as about 325 mg), and 6-15 mg of promethazine HCL (such as about 12.5 mg). The oxycodone HCL and the acetaminophen can be formulated using conventional technologies to provide for an extended time release over a desired dosage interval. All or some of the promethazine can be formulated for immediate release. In one embodiment the composition is in the form of a bi-layer tablet comprising an immediate-release layer comprising promethazine HCL and a controlled-release layer and a controlled release layer comprising acetaminophen and oxycodone or a salt thereof.

In one embodiment the compositions described herein comprise an opioid agent, a non opioid agent and an antiemetic agent, where each agent can have a purity of 60-100% by weight. In another embodiment the compositions described herein comprise an opioid agent, a non opioid agent and an antiemetic agent, where each agent can have a purity of 70-100% by weight. In another embodiment the compositions described herein comprise an opioid agent, a non opioid agent and an antiemetic agent, where each agent can have a purity of 80-100% by weight. In another embodiment the compositions described herein comprise an opioid agent, a non opioid agent and an antiemetic agent, where each agent can have a purity of 90-100% by weight. In another embodiment the compositions described herein comprise an opioid agent, a non opioid agent and an antiemetic agent, where each agent can have a purity of 85-95% by weight. In another embodiment the compositions described herein comprise an opioid agent, a non opioid agent and an antiemetic agent, where each agent can have a purity of 95-100% by weight. In another embodiment the compositions described herein comprise an opioid agent, a non opioid agent and an antiemetic agent, where each agent can have a purity of at least 70% by weight. In another embodiment the compositions described herein comprise an opioid agent, a non opioid agent and an antiemetic agent, where each agent can have a purity of at least 75% by weight. In another embodiment the compositions described herein comprise an opioid agent, a non opioid agent and an antiemetic agent, where each agent can have a purity of at least 80% by weight. In another embodiment the compositions described herein comprise an opioid agent, a non opioid agent and an antiemetic agent, where each agent can have a purity of at least 85% by weight. In another embodiment the compositions described herein comprise an opioid agent, a non opioid agent and an antiemetic agent, where each agent can have a purity of at least 90% by weight. In another embodiment the compositions described herein comprise an opioid agent, a non opioid agent and an antiemetic agent, where each agent can have a purity of at least 95% by weight. In another embodiment the compositions described herein comprise an opioid agent, a non opioid agent and an antiemetic agent, where each agent can have a purity of at least 100% by weight.

In one embodiment the compositions described herein comprise the active ingredients hydrocodone, acetaminophen and promethazine, where each ingredient can have a purity of 60-100% by weight. In another embodiment the compositions described herein comprise the active ingredients hydrocodone, acetaminophen and promethazine, where each ingredient can have a purity of 70-100% by weight. In another embodiment the compositions described herein comprise the active ingredients hydrocodone, acetaminophen and promethazine, where each ingredient can have a purity of 80-100% by weight. In another embodiment the compositions described herein comprise the active ingredients hydrocodone, acetaminophen and promethazine, where each ingredient can have a purity of 90-100% by weight. In another embodiment the compositions described herein comprise the active ingredients hydrocodone, acetaminophen and promethazine, where each ingredient can have a purity of 85-95% by weight. In another embodiment the compositions described herein comprise the active ingredients hydrocodone, acetaminophen and promethazine, where each ingredient can have a purity of 95-100% by weight. In another embodiment the compositions described herein comprise the active ingredients hydrocodone, acetaminophen and promethazine, where each ingredient can have a purity of at least 70% by weight. In another embodiment the compositions described herein comprise the active ingredients hydrocodone, acetaminophen and promethazine, where each ingredient can have a purity of at least 75% by weight. In another embodiment the compositions described herein comprise the active ingredients hydrocodone, acetaminophen and promethazine, where each ingredient can have a purity of at least 80% by weight. In another embodiment the compositions described herein comprise the active ingredients hydrocodone, acetaminophen and promethazine, where each ingredient can have a purity of at least 85% by weight. In another embodiment the compositions described herein comprise the active ingredients hydrocodone, acetaminophen and promethazine, where each ingredient can have a purity of at least 90% by weight. In another embodiment the compositions described herein comprise the active ingredients hydrocodone, acetaminophen and promethazine, where each ingredient can have a purity of at least 95% by weight. In another embodiment the compositions described herein comprise the active ingredients hydrocodone, acetaminophen and promethazine, where each ingredient can have a purity of at least 100% by weight.

In one embodiment, administration of the composition disclosed herein that comprises an antiemetic agent (such as promethazine or a salt thereof) can produce an outcome in a subject, such as reduced, abated or eliminated adverse effects associated with the administration of an opioid agent or non-opioid agent, such as oxycodone HCL, hydrocodone bitartrate and acetaminophen.

In various embodiments, the composition is in the form of any oral dosage form disclosed herein, including but not limited to a pill, tablet, or capsule. In one embodiment, the composition is in the form of a bilayer tablet having an immediate-release layer and a controlled-release layer, wherein one or more pharmaceutically active agents are present in the immediate-release layer and one or more pharmaceutically active agents are present in the controlled release layer. In another embodiment, the immediate-release layer comprises one or more antiemetic, and the controlled-release layer comprises one or more pharmaceutically active agents disclosed herein, but which are not an antiemetic or antihistamine. In a further embodiment, an antiemetic or antihistamine is present in both the immediate-release and controlled-release layer. In another embodiment, the immediate release layer comprises promethazine or a pharmaceutically acceptable salt thereof. In another embodiment, the promethazine salt is promethazine HCl. In another embodiment, the controlled-release layer comprises an opioid analgesic. In a further embodiment, the opioid analgesic is hydrocodone or oxycodone, or a pharmaceutically acceptable salt thereof. In one embodiment the hydrocodone salt is hydrocodone bitartrate. In another embodiment, the oxycodone salt is oxycodone HCl. In a further embodiment, the controlled-release layer further comprises one or more non-opioid analgesic. In one embodiment, the non-opioid analgesic is acetaminophen or a pharmaceutically acceptable salt thereof. In one embodiment, the composition is in a form that achieves a hardness of from about 5 to about 15 kiloponds, including the hardness of any single integer within this range, and has a thickness from about 5 to about 10 mm, including the thickness of any single integer within this range. In specific embodiments the tablet has a hardness of about 9.5 kiloponds or about 12.5 kiloponds. It will be understood that as to the kilapond and thickness measurements, increments of 0.1 decimal points are within the scope of the invention.

In one embodiment, the composition is capable of providing an effective plasma concentration of an antiemetic in about 1 minute to about 20 minutes after administration to a subject. In another embodiment, the antiemetic is promethazine or a pharmaceutically acceptable salt thereof. In a further embodiment the salt is promethazine HCl.

In various embodiments, a composition comprises from about 1% to about 20% by weight of an antihistamine; from about 10% to about 80% by weight a non-opioid analgesic; and from about 1% to about 20% by weight of an opioid analgesic.

In one embodiment, the composition is capable providing an effective plasma concentration of promethazine or a pharmaceutically acceptable salt thereof in about 1 minute to about 20 minutes after administration to a subject.

In one embodiment, a method is provided for reducing or eliminating an adverse effect of an analgesic agent, comprising administering to a subject in need thereof an composition comprising an effective amount of each of an opioid analgesic agent, a non-opioid analgesic agent and an agent which reduces or eliminates a adverse effect of the analgesic agents. In various embodiments, the agent useful for reducing or eliminating an adverse effect associated with administration of an opioid or non-opioid analgesic agent, is promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol, or propofol, or pharmaceutically acceptable salt thereof.

In some embodiments, a method is provided for treating or preventing pain, comprising administering to a subject in need thereof an effective amount of a composition comprising an effective amount of each of an opioid analgesic, or a pharmaceutically acceptable salt thereof, a non-opioid analgesic, or a pharmaceutically acceptable salt thereof, and an agent which reduces a adverse effect associated with the opioid or non-opioid analgesic agent. In one embodiment, the agent that reduces an adverse effect is an antiemetic or an antihistamine.

In some embodiments, the pain being treated with the composition is associated with cancer, chronic or acute pain, a headache, chronic headache, a migraine headache, a surgical procedure, acute or chronic physical injury, bone fracture or a crush injury, spinal cord injury, an inflammatory disease (e.g., pancreatitis), a non-inflammatory neuropathic or dysfunctional pain condition, or a combination thereof. In some embodiments the subject is a mammal, e.g., a human, mouse, rat, guinea pig, dog, cat, horse, cow, pig, or non-human primate, such as a monkey, chimpanzee or baboon. In specific embodiments, the subject is a human. In one embodiment a stimulant that has anti-sedative properties, which can bring pain relief to the subject with reduced sedative effects common to some opioid analgesic formulations.

As discussed herein, the compositions of the present invention can be in including, but not limited to a multi-layer tablet (e.g., a bi-layer tablet). In some specific embodiments, the multi-layer tablet is a bi-layer tablet that comprises: (a) an immediate-release layer that comprises an effective amount of an agent which reduces or eliminates an adverse effect of an opioid analgesic; and (b) a controlled-release layer that comprises an effective amount of each of an opioid analgesic agent and a non-opioid analgesic agent.

In various embodiments, the agent that reduces or eliminates an adverse effect associated with administration of an opioid or non-opioid analgesic agent is released in a subject at a substantially faster rate than an opioid or non-opioid analgesic in a composition of the invention. For example, in one embodiment, a plasma concentration of the agent that reduces or eliminates an adverse effect of an opioid analgesic is achieved in about 1 minute to about 20 minutes following oral administration, as compared with a plasma concentration of an analgesic agent, which can be achieved in about 30 minutes to about 8 hours following oral administration. In various embodiments, the compositions described herein comprise an agent that reduces or eliminates an adverse effect associated with administration of an opioid analgesic or non-opioid analgesic, where the agent provides an effective plasma concentration in about 1 minute to about 20 minutes following oral administration.

In specific embodiments, the agent that reduces or eliminates an adverse effect associated with an opioid or a non-opioid analgesic is an antihistamine or antiemetic. In various embodiments, the composition also comprises an antiemetic agent.

In one embodiment, a composition comprises an effective amount of an opioid analgesic agent, a non-opioid analgesic agent, and an agent that reduces or eliminates an adverse effect associated with administration of the opioid or non-opioid analgesic. An adverse effect of opioid or non-opioid analgesic agents includes but is not limited to nausea, vomiting, other gastric upset, skin rash, an allergic reaction such as swelling, difficulty breathing, closing of throat, abdominal pain, unusual bleeding or bruising, sedation, CNS depression, or respiratory depression. In specific embodiments, the adverse effect that is reduced or eliminated is nausea, vomiting, constipation, or a combination thereof.

In some embodiments of the invention described herein, the bi-layer tablet comprises an immediate-release layer and a controlled-release layer. In a further embodiment, the immediate-release layer comprises an antiemetic or antihistamine and the controlled-release layer comprises an opioid analgesic, a barbiturate, a stimulant, a triptan or a combination thereof. An illustrative bilayer tablet is depicted in FIG. 2. In one embodiment, a bilayer tablet of the invention has the dimensions as depicted in FIG. 2.

In another embodiment the compositions comprise an effective amount of each of an analgesic agent, an antitussive agent, and an agent that reduces or eliminates an adverse effect of the analgesic agent or the antitussive agent. In some embodiments the antitussive is also an analgesic.

Another embodiment of this invention is directed to methods for the treatment of pain, comprising administering an effective amount of each of an opioid analgesic agent, a non-opioid analgesic agent and an agent that reduces or eliminates an adverse effect of the opioid analgesic agent to a subject in need thereof.

The methods allow for use of analgesics in populations at risk of adverse effect such as nausea, vomiting, other gastric upsets, skin rashes, allergic reactions such as swelling, difficulty breathing, closing of throat, abdominal pain, unusual bleeding or bruising, skin rashes, sedation, CNS depression, or respiratory depression.

In one embodiment, the compositions comprise an effective amount of each of an opioid analgesic, an antiemetic, and an opioid antagonist, the composition is capable of providing protection from a metabolic consequence of vomiting, particularly severe vomiting, in a subject particularly prone to adverse effects associated with an opioid analgesic. An example of metabolic consequence of vomiting is dehydration. In one embodiment, the subject administered a composition of the invention is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 47, 48, 49, 50, 51, 52, 53, 54, 55, 56, 57, 58, 59, 60, 61, 62, 63, 64, 65, 66, 67, 68, 69, 70 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In another embodiment, the subject administered a composition of the invention is a child, such as a child between the ages of 0-1, 0-2, 0-10, 2-3, 2-4, 2-5, 2-6, 2-7, 2-9, 2-9, 2-10, 2-12, 2-13, 2-14, 2-15, 2-16, or 2-17 years old. In another embodiment, the subject administered a composition of the invention is 18 years or older. In another embodiment, the subject administered a composition of the invention is a geriatric patient. In another embodiment, the subject administered a composition of the invention is about 55 years of age or older, about 60 years of age or older, about 65 years of age or older, or about 70 years of age or older. In one embodiment, the composition administered to such a subject comprises an opioid analgesic and one or more antiemetic agent. In one embodiment, the composition comprises oxycodone, promethazine, and naltrexone, or a pharmaceutically acceptable salt thereof.

In various embodiments, a dosage form of the invention provides an effective plasma concentration of an antiemetic or antihistamine at from about 1 minute to about 20 minutes after administration, including at the time of any single integer within this range. In some embodiments, the release rate occurs at substantially faster as compared with release rates for the analgesic agents.

In some embodiments, the composition provides an effective plasma concentration of an opioid analgesic and/or non-opioid analgesic at from about 20 minutes to about 24 hours after administration, including at the time of any single integer within this range.

In further embodiments, the opioid and/or non-opioid analgesic is present in an effective plasma concentration in a subject from about 1 hour to 24 hour or from about 1 day to 30 days, including at the time of any single integer within this range. In addition, administration of dosage compositions can be effected through patch delivery systems which are known in the art.

In one embodiment, the composition comprises an antiemetic in an amount capable of achieving a serum level Cmax of from about 0.2 ng/mL to about 1 ng/mL at a Tmax of from about 1 to about 6 hours following oral administration. In one specific embodiment the antiemetic is promethazine or a pharmaceutically acceptable salt thereof. In another embodiment, the pharmaceutically acceptable salt is promethazine HCl. In a further embodiment, the composition is a bilayer tablet that has an immediate release layer and a controlled-release layer. In yet a further embodiment, the controlled release layer comprises an opioid analgesic agent or a non-opioid analgesic agent. In a further embodiment the immediate-release layer comprises promethazine or a pharmaceutically acceptable salt thereof.

In another embodiment, the composition comprises promethazine or a pharmaceutically acceptable salt thereof in an amount capable of achieving a serum level Cmax of about 0.46 ng/mL at a Tmax of about 2 to about 3 hours following oral administration. In one specific embodiment, the promethazine or a pharmaceutically acceptable salt is at a dose by weight in the composition of about 10 mg to about 15 mg.

In another embodiment, the promethazine or pharmaceutically acceptable salt is at a dose (by weight in the composition) of about 12.5 mg. In a further embodiment, the composition is in the form of a bilayer tablet that has an immediate release layer and a controlled-release layer. In yet another embodiment, the promethazine or a pharmaceutically acceptable salt is the only pharmaceutically active agent in the immediate release layer of a bilayer tablet of the invention. In one embodiment, the promethazine is promethazine HCl. In yet a further embodiment, the controlled release layer comprises an opioid analgesic agent or a non-opioid analgesic agent. In a further embodiment, the opioid analgesic is the only pharmaceutically active agent in the controlled-release layer of a bilayer tablet, non-opioid analgesic is the only pharmaceutically active agent in the controlled-release layer of a bilayer tablet or both the opioid analgesic and non-opioid analgesic are the only pharmaceutically active agents of the controlled-release layer of a bilayer tablet.

In another specific embodiment, the composition comprises promethazine or a pharmaceutically acceptable salt thereof in an amount capable of achieving a serum level Cmax of about 4.36 ng/ml at a Tmax of about 3.5 to about 4 hours following administration. In one embodiment, the promethazine or a pharmaceutically acceptable salt is at a dose by weight in the composition of about 10 mg to about 15 mg. In another embodiment, the promethazine or pharmaceutically acceptable salt is at a dose (by weight in the composition) of about 12.5 mg. In a further embodiment, the composition is in the form of a bilayer tablet that has an immediate release layer and a controlled-release layer. In yet another embodiment, the promethazine or a pharmaceutically acceptable salt is the only pharmaceutically active agent in the immediate release layer of a bilayer tablet of the invention. In one embodiment, the promethazine is promethazine HCl. In yet a further embodiment, the controlled release layer comprises an opioid analgesic agent or a non-opioid analgesic agent. In a further embodiment, the opioid analgesic is the only pharmaceutically active agent in the controlled-release layer of a bilayer tablet, non-opioid analgesic is the only pharmaceutically active agent in the controlled-release layer of a bilayer tablet or both the opioid analgesic and non-opioid analgesic are the only pharmaceutically active agents of the controlled-release layer of a bilayer tablet.

In another embodiment, the composition comprises hydrocodone or a pharmaceutically acceptable salt thereof in an amount capable of achieving a serum level Cmax of about 14.2 ng/ml at a Tmax of about 1.5 to about 2 hours following oral administration. In one embodiment, the hydrocodone or a pharmaceutically acceptable salt is at a dose by weight in the composition of about 5 mg to about 12 mg. In another embodiment, the hydrocodone or pharmaceutically acceptable salt is at a dose (by weight in the composition) of about 8.3 mg. In a further embodiment, the composition is in the form of a bilayer tablet that has an immediate release layer and a controlled-release layer. In yet a further embodiment, the controlled release layer comprises an opioid analgesic agent or a non-opioid analgesic agent. In one embodiment the opioid analgesic agent is hydrocodone bitartrate. In a further embodiment, the opioid analgesic is the only pharmaceutically active agent in the controlled-release layer of a bilayer tablet, the non-opioid analgesic is the only pharmaceutically active agent in the controlled-release layer of a bilayer tablet or both the opioid analgesic and non-opioid analgesic are the only pharmaceutically active agents of the controlled-release layer of a bilayer tablet. In yet another embodiment, the promethazine or a pharmaceutically acceptable salt is the only pharmaceutically active agent in the immediate release layer of a bilayer tablet of the invention. In one embodiment, the promethazine is promethazine HCl.

In another embodiment, the composition comprises acetaminophen or a pharmaceutically acceptable salt thereof in an amount capable of achieving a serum level Cmax of about 2.89 µg/ml at a Tmax of about 0.9 to about 1.2 hours following oral administration. In one embodiment, the acetaminophen or a pharmaceutically acceptable salt is at a dose by weight in the composition of about 275 mg to about 405 mg. In another embodiment, the acetaminophen or pharmaceutically acceptable salt is at a dose (by weight in the composition) of about 361 mg. In a further embodiment, the composition is in the form of a bilayer tablet that has an immediate release layer and a controlled-release layer. In yet a further embodiment, the controlled release layer comprises an opioid analgesic agent or a non-opioid analgesic agent. In a further embodiment, the non-opioid analgesic is the only pharmaceutically active agent in the controlled-release layer of a bilayer tablet, the opioid analgesic is the only pharmaceutically active agent in the controlled-release layer of a bilayer tablet or both the opioid analgesic and non-opioid analgesic are the only pharmaceutically active agents of the controlled-release layer of a bilayer tablet. In yet another embodiment, the promethazine or a pharmaceutically acceptable salt is the only pharmaceutically active agent in the immediate release layer of a bilayer tablet of the invention. In one embodiment, the promethazine is promethazine HCl.

In another specific embodiment, immediate-release occurs when there is dissolution of an agent within 1-20 minutes after oral administration. In another embodiment, immediate-release results in substantially complete dissolution within about 1 hour following oral administration. In one embodiment, a composition is capable of providing about 80% dissolution of an antiemetic in about 5 minutes (e.g., FIG. 5).

In various embodiments, immediate-release occurs when there is dissolution of an agent within 1-20 minutes after administration. Dissolution can occur in a subject's stomach and/or intestine. In another embodiment, immediate-release results in complete or less than complete dissolution within about 1 hour following administration to a subject. In another embodiment, immediate-release results in complete or less than complete dissolution within about 1 hour following rectal administration. When used in association with the dissolution profiles discussed herein, the term "immediate-release" refers to wherein all or less than the entire amount of a dosage form is dissolved.

In some embodiments, immediate-release is through inhalation, such that dissolution occurs in a subject's lungs, as further described herein. Dissolution of less than all of an active includes but is not limited to dissolution of about 50%, 60%, 70%, 80%, 85%, 90%, 95%, 97%, 98%, 99%, 99.1%, 99.2%, 99.35, 99.4%, 99.5%, 99.6%, 99.7%, 99.8% or 99.99% of the active agent. Methods for measuring dissolution profiles are known (e.g., Example 15, infra).

Exemplary Nasal Dosage Forms

The agents of the compositions and methods described herein can be administered by the nasal inhalation route using conventional nebulizers or by oxygen aerosolization to provide convenient pain relief with reduced adverse effects. The agents can be suspended or dissolved in a pharmacologically acceptable inhalation carrier. Examples of such carriers are known in the art and include distilled water, water/ethanol mixtures, and physiological saline solution. Conventional additives including sodium chloride, glucose, citric acid and the like may be employed in these dosage forms to stabilize or to provide isotonic media.

The agents described herein can also be administered as a self-propelled dosage unit in aerosol form suitable for inhalation therapy. Suitable means for employing the aerosol inhalation therapy technique are described, for example, in U.S. Pat. No. 6,913,768, which is incorporated herein by reference in its entirety. The agent can be suspended in an inert propellant such as a mixture of dichlorodifluoromethane and dichlorotetrafluoroethane, together with a co-solvent such as ethanol, together with flavoring materials and stabilizers. In one embodiment of the invention, the agents useful for a self-propelled dosage unit in aerosol form administration are hydrocodone or oxycodone, acetaminophen, and promethazine. In a further embodiment the dosage unit may further comprise an agent such as a bronchodilator (e.g., albuterol).

The agents of the compositions and methods described herein can also be administered as nasal spray/drop compositions, which can conveniently and safely be applied to subjects to effectively treat pain with reduced adverse effects. The compositions may further comprise a water soluble polymer such as polyvinylpyrrolidone, together with other medications such as sumatriptan, together with bioadhesive material.

Exemplary Intravenous and Liquid Dosage Forms

The compositions described herein can also be in liquid or liquid tannate form. The liquid formulations can comprise, for example, an agent in water-in-solution and/or suspension form; and a vehicle comprising polyethoxylated castor oil, alcohol and/or a polyoxyethylated sorbitan mono-oleate with or without flavoring.

The compositions described herein can also be administered in injection-ready stable liquids for injection or I.V. drip. In one embodiment a composition disclosed herein is administered by a subject administered injection. For example a subject can administer the composition via a hand-held injection device such as a pen type injector. In one example a subject can use a device or component disclosed in U.S. Pat. Nos. 6,146,361; 5,536,249; or 5,954,700 (which are herein incorporated by reference in their entirety) to administer a pharmaceutical composition disclosed herein.

Exemplary Topical and Transdermal Dosage Forms

The compositions described herein can also be administered topically to the skin of a subject. The agents can be mixed with a pharmaceutically acceptable carrier or a base which is suitable for topical application to skin to form a dermatological composition. Suitable examples of carrier or base include, but not limited to, water, glycols, alcohols, lotions, creams, gels, emulsions, and sprays. A dermatological composition comprising an analgesic agent can be integrated into a topical dressing, medicated tape, dermal patch absorbing gel and cleansing tissues.

In another embodiment, the invention relates to a method of use and a system for the transdermal delivery of one or more pharmaceutically active agents into a subject. In one embodiment a portion of the skin of a subject is sealed with a thin, film layer of a base material to occlude the skin and transport a desired dosage of at least one pharmaceutically active agent across the a layer, which can be from a rate-controlling system in contact with the thin layer. The rate-controlling system can be a thin rate-controlling membrane interposed between one or more agents and the thin layer. In another embodiment a reservoir delivers at least one pharmaceutically active agent to the layer for delivery into a subject. In some embodiments the pharmaceutically active agents to be delivered are: an opioid analgesic, a non-opioid analgesic and an antihistamine; or pharmaceutically acceptable salts, solvates, or prodrugs thereof; one or more pharmaceutically acceptable excipients or carriers.

In one embodiment, the rate-controlling system or reservoir comprises at least one pharmaceutically active agent to be delivered, is dispersed in a base material and contained within a container system. In one embodiment at least one pharmaceutically active agent is dissolved in the base material. In another embodiment at least one pharmaceutically active agent is uniformly dispersed in the base material. In another embodiment, the rate-controlling system or reservoir comprises microparticles of at least one pharmaceutically active agent to be delivered suspended in a base material and contained within a container system. In one embodiment the base material is a viscous material. The container system may comprise a macroporous, non-rate-controlling face membrane with an impervious backing to form a pool or patch-like system of desired face membrane area with the face of the membrane placed over and in contact with the thin, occluding, viscous layer on the skin. The thin viscous layer may be coated or placed on the skin repeatedly, and the patch system placed on top of the thin, viscous layer or the viscous layer formed in situ by exudation through the membrane face when the patch or pool system is placed in position on the skin. In one embodiment the patch or pool container system generally is retained in a transdermal position by the use of a peripheral adhesive layer about the patch or pool. In one embodiment, the face or transport area of the membrane is covered prior to use by a removable cover such as a peelable strip of impervious sheet material. In another embodiment, microcapsules containing a drug for delivery may be suspended in a viscous base material, and the composition then spread as a layer over the skin of the user with or without a covering material.

In other embodiments U.S. Pat. Nos. 4,906,463; 4,588, 580; 4,685,911, 4,626,539, 4,834,978 and 5,635,204 disclose useful transdermal patches which may be used for the practice methods and compositions described herein, which are herein incorporated by reference in their entirety.

Exemplary Suppository Dosage Forms

The compositions described herein can also be administered in a suppository form, comprising an outer layer containing the composition in a suppository base. The suppository base may, for example, be any conventional suppository base material such as glycogelatin, polyethylene glycol, fractionated palm kernel oil, or one or more natural, synthetic or semi synthetic hard fats such as cocoa butter. In one embodiment the suppository is useful for vaginal or rectal administration. In some embodiments the suppository is effervescent.

In some embodiments the suppository base material contains hydrophobic or hydrophilic media, each of which can melt at body temperature. In one embodiment the suppository base material used can be cocoa butter or similar material. In another embodiment the suppository base material can be a moist polymer is then mixed with the one or more pharmaceutically active agents and compressed into the desired form. In one embodiment at least one pharmaceutically active agent is dissolved in the suppository base material. In another embodiment at least one pharmaceutically active agent is uniformly dispersed in the suppository base material. In another embodiment, the suppository base material comprises microparticles of at least one pharmaceutically active agent to be delivered suspended in the suppository base material. In some embodiments (such as vaginal suppositories) the suppository is effervescent. In some embodiments the effervescing properties are imparted for the purpose of enhancing the rapid disintegration properties of the suppository.

In other embodiments U.S. Pat. Nos. 4,265,875 and 4,853,211 disclose useful suppositories which may be used for the practice of methods and compositions described herein, which are herein incorporated by reference in their entirety.

Exemplary Administrations

Described herein are methods for preventing an adverse effect such as nausea, vomiting, other gastric upsets, skin rashes, itching, allergic reactions such as swelling, difficulty breathing, closing of throat, abdominal pain, unusual bleeding or bruising, skin rashes, sedation, CNS depression, or respiratory depression in a subject receiving, or in need of, opioid analgesic therapy. The prevention of an adverse effect can be accomplished by the administration of an effective amount of promethazine or other antihistamine with the chosen analgesic agent or agents. In one embodiment, the invention provides methods for treating pain, comprising administering to a subject in need thereof an effective amount of an opioid analgesic agent, a non-opioid analgesic agent, an agent that reduces side effects of the opioid analgesic agent and optionally a stimulant agent. In one embodiment, the non-opioid analgesic agent is acetaminophen. In another embodiment, the agent that reduces an adverse effect is promethazine. In another embodiment, the invention provides methods for treating pain, comprising administering to a subject in need thereof an effective amount of an opioid analgesic agent, a non-opioid analgesic agent, a barbiturate agent, an agent that reduces side effects of the opioid analgesic agent and optionally a stimulant agent. In another embodiment, the invention provides methods for treating pain, comprising administering to a subject in need thereof an effective amount of an opioid analgesic agent, a barbiturate agent, an agent that reduces side effects of the opioid analgesic agent and optionally a stimulant agent. In another embodiment, the invention provides methods for treating pain, comprising administering to a subject in need thereof an effective amount of an a non-opioid analgesic agent, a barbiturate agent, an agent that reduces side effects of the opioid analgesic agent and optionally a stimulant agent. In another embodiment, the invention provides methods for treating pain, comprising administering to a subject in need thereof an effective amount of an opioid analgesic agent, an agent that reduces side effects of the opioid analgesic agent and optionally a stimulant agent.

The administration can continue for only a relatively short time in the case of an acute condition requiring opioid therapy or for long periods in the case of conditions requiring chronic use of opioid analgesics. The dosing of analgesics can be dependent upon the condition being treated, the subject's individual perception of pain and the use of the opioid on a set time schedule as a prophylactic to prevent the onset of pain or on an as needed basis in response to perceived pain. The choice of selecting a dosage of a composition that contains suitable amount of promethazine can be dependent upon the extent and severity of the adverse effects including nausea, vomiting, other gastric upsets, skin rashes, allergic reactions such as swelling, difficulty breathing, closing of throat, abdominal pain, unusual bleeding or bruising, skin rashes, sedation, CNS depression, or respiratory depression in a subject, upon the sensitivity to side-effect-reducing compounds such as promethazine in a subject, upon the likelihood of subject losing medication by vomiting, and/or on an as needed basis in response to perceived adverse effects. The dosage can be assessed by a prescribing professional evaluating the subject, the condition treated, the analgesic to be used, diet and the expected duration of therapy.

In one embodiment, compositions and methods described herein provides for a method for treating a subject suffering from or susceptible to pain, comprising administering to said subject an effective amount of a composition comprising an effective amount of a first component which is a non-opioid analgesic, or a pharmaceutically acceptable salt thereof, an effective amount of a second component which is a non-opioid analgesic, or a pharmaceutically acceptable salt thereof and an effective amount of a third component which is an antihistamine.

In another embodiment, a method for treating a subject is provided comprising administering an effective amount of a composition comprising: an effective amount of a first pharmaceutically active agent which is an opioid analgesic, or a pharmaceutically acceptable salt thereof an effective amount of a second pharmaceutically active agent which is a non-opioid analgesic, or a pharmaceutically acceptable salt thereof and an effective amount of a third pharmaceutically active agent which is an antihistamine or an anti-emetic. In one embodiment the at least one adverse effect is nausea, vomiting, other gastric upsets, skin rashes, allergic reactions such as swelling, difficulty breathing, closing of throat, itching, abdominal pain, unusual bleeding or bruising, skin rashes, sedation, CNS depression, or respiratory depression. In one embodiment the non-opioid analgesic is acetaminophen or analogue thereof. In one embodiment, the antihistamine is promethazine. In one embodiment, the opioid analgesic is hydrocodone. In another embodiment the opioid analgesic is oxycodone. In another embodiment, the invention provides methods for preventing or ameliorating an adverse effect associated with administration of an analgesic, comprising administering to a subject in need thereof an effective amount of an opioid analgesic agent, a non-opioid analgesic agent, an agent that reduces side effects of the opioid analgesic agent and optionally a stimulant agent. In one embodiment, the non-opioid analgesic agent is acetaminophen. In another embodiment, the agent that reduces an adverse effect is promethazine. In another embodiment, the invention provides methods for preventing or ameliorating an adverse effect associated with administration of an analgesic, comprising administering to a subject in need thereof an effective amount of an opioid analgesic agent, a non-opioid analgesic agent, a barbiturate agent, an agent that reduces side effects of the opioid analgesic agent and optionally a stimulant agent. In another embodiment, the invention provides methods for preventing or ameliorating an adverse effect associated with administration of an analgesic, comprising administering to a subject in need thereof an effective amount of an opioid analgesic agent, a barbiturate agent, an agent that reduces side effects of the opioid analgesic agent and optionally a stimulant agent. In another embodiment, the invention provides methods for preventing or ameliorating an adverse effect associated with administration of an analgesic, comprising administering to a subject in need thereof an effective amount of an a non-opioid analgesic agent, a barbiturate agent, an agent that reduces side effects of the opioid analgesic agent and optionally a stimulant agent. In another embodiment, the invention provides methods for preventing or ameliorating an adverse effect associated with administration of an analgesic, comprising administering to a subject in need thereof an effective amount of an opioid analgesic agent, an agent that reduces side effects of the opioid analgesic agent and optionally a stimulant agent.

In another embodiment, compositions and methods described herein provides for a method for preventing an adverse effect such as nausea, vomiting, and a skin rash in a subject receiving or in need of opioid therapy by the administration of an effective amount of acetaminophen or analogue thereof and promethazine with the opioid analgesic agent. In one embodiment, the opioid analgesic is hydrocodone. In another embodiment the opioid analgesic is oxycodone. In one embodiment, administration of a composition comprising a non-opioid analgesic and an antihistamine enhances the reduction or elimination of adverse effects associated with an opioid analgesic. For example, addition of promethazine and acetaminophen/ibuprofen reduces or eliminates an adverse effect associated with an opioid analgesic in a synergistic manner.

It is believed that administration of a composition would result in treatment of the subject which includes elimination or reduction of an adverse effect associated with analgesics (e.g., opioids) and enhance the beneficial uses of such analgesics. Such an adverse effect can otherwise render administration of certain analgesics intolerable, due to for example vomiting, nausea, and skin rashes. Therefore, various embodiments of the methods of the invention are directed to target populations of subjects that are susceptible to such an adverse effect(s), thus allowing such subjects to benefit from the pain-alleviating effects of analgesic-based pain relief, administration of which would otherwise be intolerable.

For example, by reducing the risk of vomiting, the risk of subject losing the analgesics (and losing the pain-relieving beneficial effects of analgesics) by vomiting is minimized. Furthermore, administration can be adjusted to provide the dose of side-effect-reducing compound to match the subject's analgesic ingestion without separate intervention by the health care professionals. Adding one or more additional active agents, such as promethazine, to the present compositions is believed to result in a composition having reduced potential for abuse and diversion.

Treatment or Prevention of Pain

The present compositions and methods are useful for treating or preventing pain. Accordingly the present invention includes methods for treating or preventing pain, comprising administering to a subject in need thereof a composition. Pain treatable or preventable includes, but is not limited to, pain associated with cancer, chronic or acute pain, headache pain, migraine headache, chronic headache, surgical procedure, acute or chronic physical injury, bone fracture or crush injuries, spinal cord injury, inflammatory disease (e.g., pancreatitis), noninflammatory neuropathic or dysfunctional pain conditions, or a combination thereof.

Various methods of drug administration known in the art or disclosed herein are utilized to deliver a composition of present invention to a subject in need thereof.

In some embodiments, methods of treatment or prevention comprising administering a composition are for treating pain or preventing pain. In some embodiments, the pain treatable or preventable via administration of a composition of the invention includes but is not limited to headache pain, and/or headache related symptoms as further described herein below.

Treatment or Prevention of Headache

The present compositions and methods are useful for treating or preventing a headache. Preventable or treatable headaches include but are not limited to migraine headaches (with or without aura), cluster headaches, chronic headaches, tension type headaches, Hemicrania Continua, new daily persistent, chronic tension type headaches or any combination thereof. In one embodiment, a method for treating or preventing a headache comprises administering to a subject in need thereof a composition of the invention. Each of such compositions is fully described herein.

Migraines and cluster headaches are both important, well-known, and extensively studied medical problem. In many cases, they completely incapacitate a sufferer for the duration of the headache. Their physiological embodiments, causative and aggravating factors, and current Treatments are discussed in detail in numerous scientific articles, and in full-length medical textbooks such as Headache in Clinical Practice (edited by S. Silberstein et al., Oxford Univ. Press, 1998); The Headaches, by J. Olesen; and Headache Disorders: A Management Guide for Practitioners, by A. Rapoport and F. Sheftell (W. B. Saunders, Philadelphia, 1996), which are herein incorporated by reference in their entirety. In addition, various definitions, categories, and diagnostic standards are defined by standardized criteria that have been approved and issued by the International Headache Society (IHS), which were published as a supplement to the journal Cephalalgia (Cephalalgia. 2004; 24 Suppl 1:9-160) and is herein incorporated by reference in its entirety.

In one embodiment a composition of the invention is administered to a subject to treat, eliminate or prevent at least one headache symptom. An effective amount is a dosage sufficient to reduce at least one symptom associate with a headache. Headache symptoms include: (1) frequency, which can be evaluated over a span of time, such as number of such headaches per week, per month, or per year; (2) duration, which evaluates (usually in hours) how long a headache lasts, from the time it begins to develop into a migraine or cluster headache, until it has been resolved; and (3) severity (also referred to as intensity), which is based on subjective estimates of the severity or intensity of pain or other symptoms (such as nausea) being suffered by patients during such headaches. In one embodiment a composition is used in a method to reduce the frequency, duration or severity of a preventable or treatable headache.

Treatment or Prevention of Photophobia

In one embodiment, provided herein are methods for treating or preventing photophobia, comprising administering to a subject in need thereof a composition of the invention. In one embodiment the composition comprises an effective amount of each of an opioid analgesic and an antiemetic, as disclosed herein above. In one embodiment, the antiemetic is promethazine or a pharmaceutically acceptable salt thereof and the opioid analgesic is hydrocodone, oxycodone or a pharmaceutically acceptable salt thereof. In a further embodiment, the composition is in the form of a bilayer tablet that comprises an immediate-release layer and a controlled-release layer. In another embodiment the immediate-release layer comprises promethazine or a pharmaceutically acceptable salt thereof, and the controlled-release layer comprises hydrocodone, oxycodone or a pharmaceutically acceptable salt thereof. In a further embodiment, the photophobia is associated with a migraine headache.

In another embodiment, provided herein are methods for treating or preventing photophobia, comprising administering to a subject in need thereof a composition comprising an effective amount of a triptan and an effective amount of an antiemetic. In a further embodiment the triptan is a sumatriptan or a pharmaceutically acceptable salt thereof, and the antiemetic is promethazine or a pharmaceutically acceptable salt thereof. In one embodiment, the sumatriptan salt is sumatriptan succinate.

In yet a further embodiment, the composition is in the form of a bilayer tablet that comprises an immediate-release layer and a controlled-release layer. In another embodiment the controlled-release layer comprises sumatriptan or a pharmaceutically acceptable salt thereof, and the immediate-release layer comprises promethazine or a pharmaceutically acceptable salt thereof.

EXAMPLES

Example 1

Example of an analgesic composition comprising Hydrocodone Bitartrate, Acetaminophen and Promethazine Hydrochloride.

| Analgesic Composition A | |
| --- | --- |
| INGREDIENT | QUANTITY/TABLET (MGS) |
| Hydrocodone Bitartrate | 7.5 |
| Acetaminophen | 325 |
| Promethazine Hydrochloride | 12.5 |

Example 2

The composition of Example 1 is formulated in the form of a bi-layer tablet having an immediate-release layer comprising 12.5 mg of promethazine hydrochloride and having a controlled-release layer comprising 7.5 mg of hydrocodone bitartrate and 325 mg of acetaminophen.

Example 3

The composition of Example 1 or Example 2 is orally administered with water to a subject having a tendency to exhibit adverse effects of opioid administration, such as gastric upset, nausea, vomiting, skin rash, sedation, CNS depression, or respiratory depression. Such subjects, upon taking the composition will receive an effective amount of promethazine in their blood stream. The promethazine will reduce the adverse effects that such a target population would otherwise exhibit.

Example 4

Analgesic composition comprising Oxycodone Hydrochloride, Acetaminophen and Promethazine Hydrochloride.

| Analgesic Composition B | |
| --- | --- |
| INGREDIENT | QUANTITY/TABLET (MGS) |
| Oxycodone HCl | 5 or 7 |
| Acetaminophen | 325 |
| Promethazine Hydrochloride | 12.5 |

Example 5

The composition of Example 4 is formulated in the form of a bi-layer tablet having an immediate-release layer comprising 12.5 mg of promethazine hydrochloride, and having a controlled-release layer comprising 5 or 7.5 mg of oxycodone HCl and 325 mg of acetaminophen.

Example 6

The composition of Example 5 or Example 6 is orally administered with water to a subject having a tendency to exhibit adverse effects of opioid administration, such as gastric upset, nausea, vomiting, skin rash, sedation, CNS depression, or respiratory depression. Such subjects, upon taking the composition will receive an effective amount of promethazine which will reduce the adverse effects that such a target population would otherwise exhibit.

Example 7

An abuse safeguard drug formulation comprising Hydrocodone Bitartrate, Acetaminophen and Promethazine Hydrochloride.

| Analgesic Composition C | |
| --- | --- |
| INGREDIENT | QUANTITY/TABLET (MGS) |
| Hydrocodone Bitartrate | 7.5 |
| Acetaminophen | 325 |
| Promethazine HCl | 12.5 |
| Naltrexone | 0.75 |

Example 8

The composition of Example 7 is formulated in the form of a bi-layered tablet having an immediate-release layer comprising 12.5 mg of promethazine hydrochloride, and having a controlled-release layer comprising 7.5 mg of hydrocodone bitartrate and 325 mg of acetaminophen.

Example 9

The composition of Example 7 or Example 8 is orally administered with water to a subject having a tendency to exhibit adverse effects of opioid administration, such as gastric upset, nausea, vomiting, skin rash, sedation, CNS depression, or respiratory depression. Such subjects, upon taking the composition will receive an effective amount of promethazine in their blood stream. The promethazine will reduce the adverse effects that such a target population would otherwise exhibit.

Example 10

Example of an abuse safeguard drug formulation comprising Oxycodone HCl, Acetaminophen and Promethazine HCl.

| Analgesic Composition D | |
| --- | --- |
| INGREDIENT | QUANTITY/TABLET (MGS) |
| Oxycodone HCl | 5 or 7.5 |
| Acetaminophen | 325 |
| Promethazine HCl | 12.5 |
| Naltrexone | 0.5 or 0.75 |

Example 11

The composition of Example 10 is in the form of a bi-layer tablet having an immediate-release layer comprising 12.5 mg of promethazine hydrochloride, and having a controlled-release layer comprising 5 or 7.5 mg of oxycodone HCl and 325 mg of acetaminophen.

Example 12

The composition of Example 10 or Example 11 is orally administered with water to a subject having a tendency to exhibit adverse effects of opioid administration, such as gastric upset, nausea, vomiting, skin rash, sedation, CNS depression, or respiratory depression. Such subjects, upon taking the composition will receive an effective amount of promethazine in their blood stream. The promethazine will reduce the adverse effects that such a target population would otherwise exhibit.

Example 13

Example of a bi-layer tablet analgesic composition comprising Hydrocodone or a Pharmaceutically Acceptable Salt Thereof, Acetaminophen and Promethazine or a Pharmaceutically Acceptable Salt Thereof.

| Controlled Release Layer - Example 13A | |
|---|---|
| INGREDIENT | QUANTITY/TABLET (MGS) |
| Hydrocodone, or salt thereof | 6.5 to 8.5 |
| Acetaminophen, or salt thereof* | 328 to 402 |
| Silicified Microcrystalline Cellulose | 135 to 170 |
| Hydroxy Methyl Propyl Cellulose | 17 to 23 |
| Magnesium Stearate | 1 to 4 |
| Stearic Acid | 1 to 4 |

*100% acetaminophen or about 89.5% or 89.05% acetaminophen.

| Immediate Release Layer - Example 13A | |
|---|---|
| INGREDIENT | QUANTITY/TABLET (MGS) |
| Promethazine, or salt thereof | 11 to 14 |
| Silicified Microcrystalline Cellulose | 100 to 140 |
| Croscarmellose Sodium | 12 to 18 |
| Magnesium Stearate | 0.8 to 1.5 |

| Controlled Release Layer - Example 13B | |
|---|---|
| INGREDIENT | QUANTITY/TABLET (MGS) |
| Hydrocodone, or salt thereof | 7.5 |
| Acetaminophen, or salt thereof* | 360 |
| Silicified Microcrystalline Cellulose | 152 |
| Hydroxy Methyl Propyl Cellulose | 20 |
| Magnesium Stearate | 2.7 |
| Stearic Acid | 2.7 |

*100% acetaminophen or about 89.5% or 89.05% acetaminophen.

| Immediate Release Layer - Example 13B | |
|---|---|
| INGREDIENT | QUANTITY/TABLET (MGS) |
| Promethazine, or salt thereof | 12.5 |
| Silicified Microcrystalline Cellulose | 121.5 |
| Croscarmellose Sodium | 15 |
| Magnesium Stearate | 1 |

| Analgesic Composition F1 - Controlled Release Layer (Bottom Layer) | |
|---|---|
| INGREDIENT | QUANTITY/TABLET (MGS) |
| Hydrocodone Bitartrate | 7.5 |
| Acetaminophen 89.5% | 360.5 |
| Silicified Microcrystalline Cellulose | 150 |
| Hydroxy Methyl Propyl Cellulose | 10 |
| Croscarmellose Sodium | 23 |
| Magnesium Stearate | 1 |

| Analgesic Composition F1 - Immediate Release Layer (Top Layer) | |
|---|---|
| INGREDIENT | QUANTITY/TABLET (MGS) |
| Promethazine HCL | 12.5 |
| Prosolve SMCC (HD90) | 121.5 |
| Croscarmellose Sodium | 15 |
| Crospovidone NF | 15 |
| Avicel PH200 | 21.5 |
| Magnesium Stearate | 1 |

| Analgesic Composition F2 - Controlled Release Layer (Bottom Layer) | |
|---|---|
| INGREDIENT | QUANTITY/TABLET (MGS) |
| Hydrocodone Bitartrate | 7.5 |
| Acetaminophen 89.05% | 364.96 |
| Silicified Microcrystalline Cellulose | 152.04 |
| Hydroxy Methyl Propyl Cellulose | 20 |
| Stearic Acid | 2.75 |
| Magnesium Stearate | 2.75 |

| Analgesic Composition F2 - Immediate Release Layer (Top Layer) | |
|---|---|
| INGREDIENT | QUANTITY/TABLET (MGS) |
| Promethazine HCL | 12.5 |
| Prosolve SMCC (HD90) | 121.5 |
| Croscarmellose Sodium | 15 |
| Magnesium Stearate | 1 |

Example 14

The compositions of Example 13 are orally administered with water to a subject having a tendency to exhibit adverse effects of opioid administration, such as gastric upset, nausea, vomiting, skin rash, sedation, CNS depression, or respiratory depression. Such subjects, upon taking the compositions will receive an effective amount of promethazine in their blood stream. The promethazine will reduce the adverse effects that such a target population would otherwise exhibit.

Example 15

Dissolution Data

Dissolution apparatus was a USP Rotating Paddle Apparatus 2 with an automated sampling station (e.g., VK-8000 or equivalent). Dissolution fluid was 900 mL of de-aerated 0.01 N HCl, maintained at 37.0+/−0.5° C. during dissolution procedure. The fluid was prepared by diluting 5 mL of concentrated HCl in 6000 mL of de-aerated water, and mixed. To measure peaks, a dual wavelength detector (e.g., Hitachi L-2420) was used, or alternatively, two separate chromatographic systems can be used in order to measure the peaks at two different wavelengths.

Standard Solution Preparation: Each ingredient was weighed (e.g., 21 mg of hydrocodone bitartrate) into a 50 mL volumetric flask, and diluted to volume with dissolution media. The resulting solution was mixed to form a stock solution. Different ingredients were similarly prepared to provide stock solutions (e.g., promethazine HCl, acetaminophen). 2 mL each of stock standard solutions were diluted with dissolution fluid and mixed to produce a final standard solution. For example, the concentration of hydrocodone bitartrate was about 0.0084 mg/mL, promethazine HCl was about 0.014 mg/mL, and acetaminophen was about 0.36 mg/mL.

Dissolution test solutions were prepared in 900 mL of 0.01 N HCl using the USP Rotating Paddle Apparatus at 50 WM. An aliquot of the dissolution solution was filtered and a 50-pL aliquot was chromatographed on a 50-mm×4.6-mm (i.d.) Waters SunFire™ $C_{18}$, 3.5-μm particle size column using a gradient HPLC method. Mobile phase A consisted of water/acetonitrile/TFA, 950/50/2 (v/v/v) and mobile phase B consisted of water/acetonitrile/TFA, 50/950/1.5 (v/v/v). The flow rate was 2.0 mL/minute. For example, the amount of acetaminophen released was determined at 300 nm by comparing the area obtained for the peak due to acetaminophen in the chromatogram of the dissolution test solution to that obtained for the corresponding peak in a chromatogram of a standard solution. The amount of hydrocodone bitartrate released was determined at 230 nm by comparing the area obtained for the peak due to hydrocodone bitartrate in the chromatogram of the dissolution test solution to that obtained for the corresponding peak in a chromatogram of a standard solution. The amount of promethazine HCl released was determined at 230 nm by comparing the area obtained for the peak due to promethazine HCl in the chromatogram of the dissolution test solution to that obtained for the corresponding peak in a chromatogram of a standard solution.

Paddle speed was 50 rpm; pull volume was 10 mL (no replacement); Pull points: 5, 10, 15, 20, 25, 30, 45 and 60 minutes. The amount of each component dissolved in the dissolution medium was determined by HPLC. The method can use a high purity, bonded C18 stationary phase and a binary mobile phase consisting of an appropriate buffer and organic modifier.

Dissolution Procedure. 900 mL of dissolution fluid preheated to 37° C. was placed into each vessel. Tablets of Analgesic Composition F.2 above were weighed and placed in vessels respectively. At prescribed time intervals, 5 mL aliquot of the dissolution fluid was drawn using the automated sampling station equipped with a 35 μm full flow filter connected to a sampling probe. Filtrate was allowed to cool to room temperature, to produce a final sample solution. Fluid withdrawn was not replaced. Samples were injected in HPLC for analysis after a baseline was established. Peak area responses were measured for each component: acetaminophen peak eluted at about 1.5 minutes; hydrocodone bitartrate eluted at about 3.3 minutes and promethazine HCl eluted at about 4.8 minutes. The resolution between each peak was calculated, as well as the tailing factor. The mean and % RSD values for the acetaminophen peak areas at 300 nm were measured; promethazine HCl and hydrocodone bitartrate at 230 nm. The five replicate injections were not more than 2.0% RSD. 50 μL aliquots of standard and sample solutions were subjected to liquid chromatography. A typical chromatogram of a standard solution is illustrated in FIG. 1.

Figure 3:
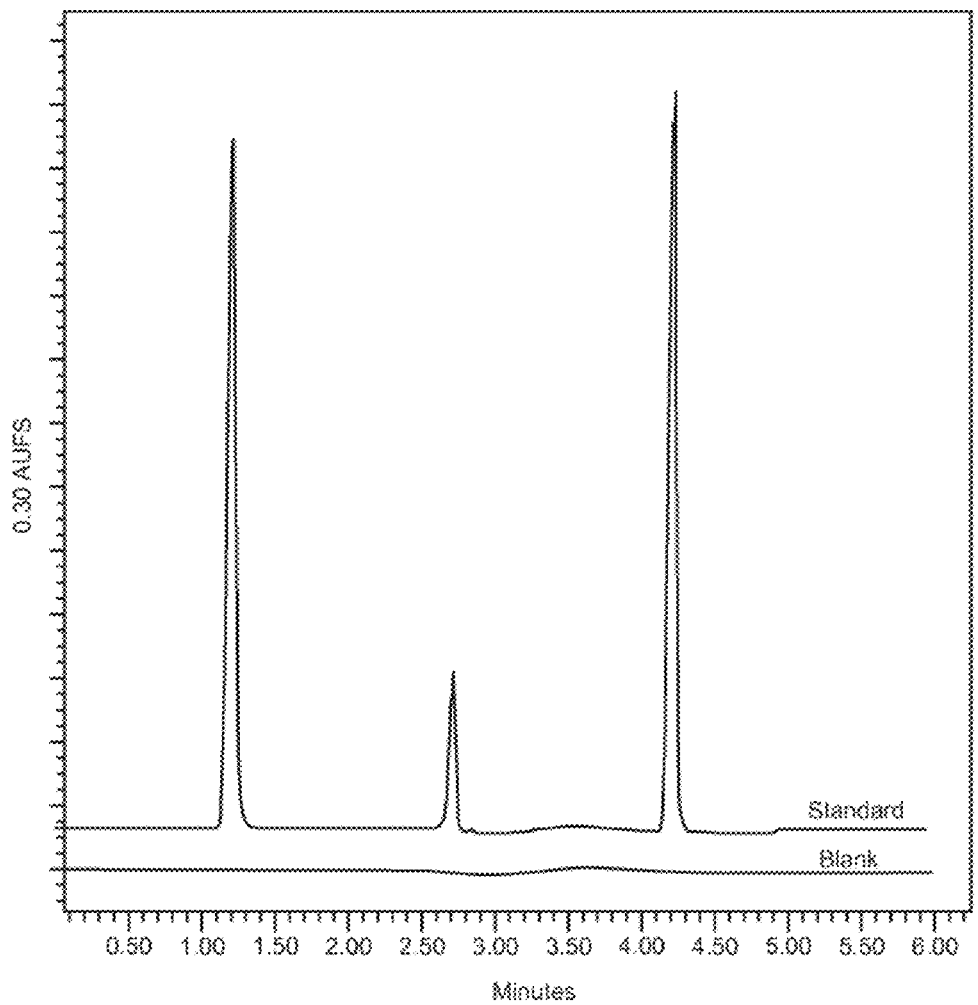
FIG. 3 illustrates an example of chromatograph of a diluent blank and standard solution.
Figure 4:
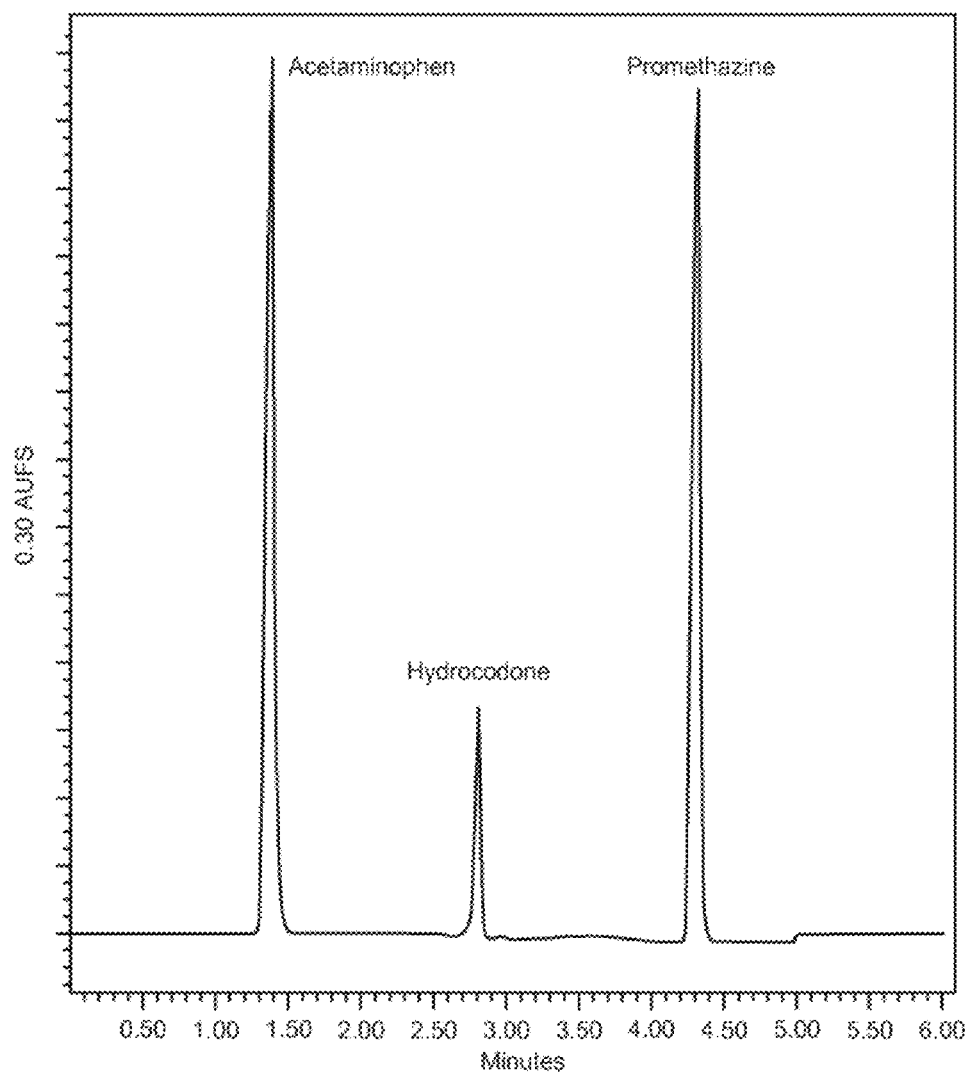
FIG. 4 illustrates an example of a dissolution chromatograph for analgesic composition F.2 of Example 13.

The amount of a pharmaceutically active agent in a tablet is determined by comparing the area obtained for the peak due to the agent in a chromatogram of the dissolution test solution to that obtained for the corresponding peak in a chromatogram of a standard solution. For example the standard peaks are provided in FIG. 3, while the test solutions are provide in FIG. 4.

Example 16

A bi-layer tablet analgesic composition comprising Hydrocodone or a Pharmaceutically Acceptable Salt Thereof, Acetaminophen and Promethazine or a Pharmaceutically Acceptable Salt Thereof.

| Controlled Release Layer - Example 16A | |
|---|---|
| INGREDIENT | QUANTITY/TABLET (MGS) |
| Hydrocodone, or salt thereof* | 6.5 to 8.5 |
| Acetaminophen, or salt thereof* | 300 to 402 |
| Silicified Microcrystalline Cellulose | 135 to 170 |
| Hydroxy Methyl Propyl Cellulose | 8 to 23 |
| Magnesium Stearate | 1 to 4 |
| Stearic Acid | 1 to 4 |

*100% acetaminophen or about 90% acetaminophen.
*100% hydrocodone or about 90% hydrocodone.

| Immediate Release Layer - Example 16A | |
|---|---|
| INGREDIENT | QUANTITY/TABLET (MGS) |
| Promethazine, or salt thereof | 11 to 14 |
| Silicified Microcrystalline Cellulose | 100 to 140 |
| Croscarmellose Sodium | 12 to 18 |
| Magnesium Stearate | 0.8 to 1.5 |

| Controlled Release Layer - Example 16B | |
|---|---|
| INGREDIENT | QUANTITY/TABLET (MGS) |
| Hydrocodone, or salt thereof* | 7.5 |
| Acetaminophen, or salt thereof* | 325 |
| Silicified Microcrystalline Cellulose | 149.5 |
| Hydroxy Methyl Propyl Cellulose | 15.5 |
| Magnesium Stearate | 2.7 |
| Stearic Acid | 2.7 |
| Croscarmellose Sodium | 10 |

*100% acetaminophen or about 90% acetaminophen.
*100% hydrocodone or about 90% hydrocodone.

| Immediate Release Layer - Example 16B | |
|---|---|
| INGREDIENT | QUANTITY/TABLET (MGS) |
| Promethazine, or salt thereof | 12.5 |
| Silicified Microcrystalline Cellulose | 121.5 |
| Croscarmellose Sodium | 15 |
| Magnesium Stearate | 1 |

Controlled Release Layer - Example 16C (Bottom Layer)

| INGREDIENT | QUANTITY/TABLET (MGS) |
|---|---|
| Hydrocodone bitartrate | 8.3 |
| Acetaminophen 90% | 361.1 |
| Silicified Microcrystalline Cellulose | 149.6 |
| Hydroxy Methyl Propyl Cellulose | 15.5 |
| Croscarmellose Sodium | 10 |
| Magnesium Stearate | 2.75 |
| Stearic Acid | 2.75 |

Immediate Release Layer - Example 16C (Top Layer)

| INGREDIENT | QUANTITY/TABLET (MGS) |
|---|---|
| Promethazine, or salt thereof | 11 to 14 |
| Silicified Microcrystalline Cellulose | 100 to 140 |
| Croscarmellose Sodium | 12 to 18 |
| Magnesium Stearate | 0.8 to 1.5 |

Example 17

A controlled release bi-layer tablet containing acetaminophen, hydrocodone and promethazine and excipients in the amounts below was prepared and tested. The dissolution profile results for this bi-layer tablet are provided in Table 1.

Controlled Release Layer - Example 17

| INGREDIENT | QUANTITY/TABLET (MGS) |
|---|---|
| Acetaminophen 90% | 361.1 |
| Hydrocodone Bitartrate | 8.3* |
| Silicified Microcrystalline Cellulose | 155.1* |
| Hypromellose 2208-4M | 20 |
| Magnesium Stearate 5712 | 2.75 |
| Stearic Acid NF Vegetable Grade | 2.75 |

*Silicified Microcrystalline Cellulose was adjusted based on the potency of the Hydrocodone Bitartrate. The potency for the lot was calculated to be 90.4% (calculated using the assay result and water content).

Immediate Release Layer - Example 17

| INGREDIENT | QUANTITY/TABLET (MGS) |
|---|---|
| Promethazine HCL | 12.5 |
| Silicified Microcrystalline Cellulose | 121.5 |
| Croscarmellose Sodium | 15 |
| Magnesium Stearate | 1 |

TABLE 1

Dissolution Profile Results for Example 17

| Active | Specifications | Results Average (Min-Max) |
|---|---|---|
| Acetaminophen | 35-70% in 5 minutes | 49.9 (43.0-57.8%) |
| Acetaminophen | NLT 65% in 30 minutes | 74.0 (69.6-79.2%) |
| Acetaminophen | NLT 80% in 60 minutes | 82.3 (75.8-90.6%) |
| Hydrocodone Bitartrate | 25-60% in 5 minutes | 37.1 (28.4-47.9%) |
| Hydrocodone Bitartrate | NLT 65% in 30 minutes | 81.3 (72.1-94.6%) |
| Hydrocodone Bitartrate | NLT 80% in 60 minutes | 93.3 (85.9-107.1%) |
| Promethazine HCL | NLT 50% in 5 minutes | 93.9 (90.2-97.3%) |
| Promethazine HCL | NLT 80% in 30 minutes | 96.8 (91.7-101.1%) |
| Promethazine HCL | NLT 80% in 60 minutes | 100.3 (95.9-105.5%) |

Figure 6:
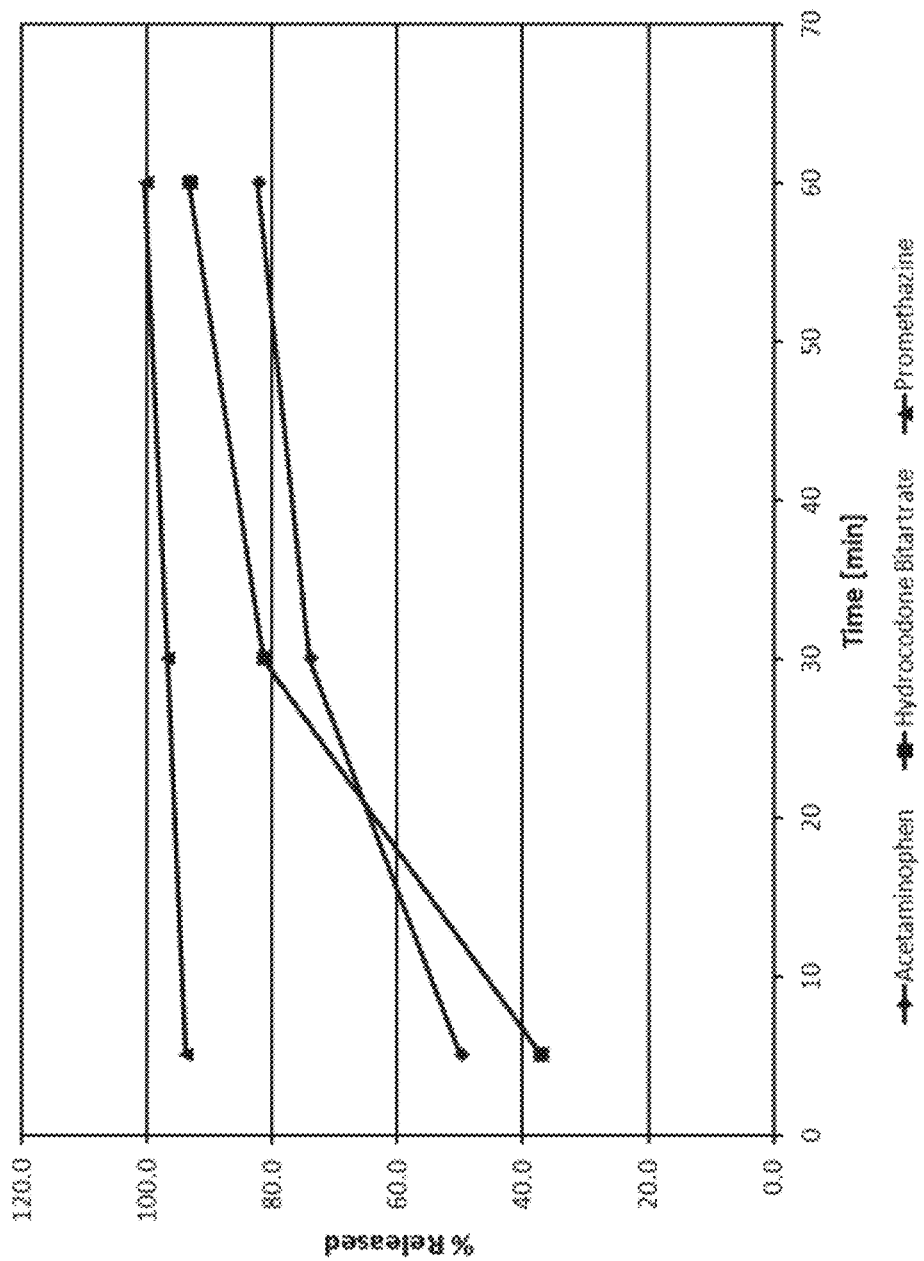
FIG. 6 illustrates an example of the dissolution release profile for analgesic compositions of Example 17.

The formulation of Example 17 was designed to release the promethazine immediately with the acetaminophen and hydrocodone bitartrate to be released slightly slower. As show in Table 1, the dissolution profile of Example 17 met this goal, however some of the time points for both the acetaminophen and hydrocodone bitartrate were close to the specification limits. Specifically, the individual tablets for the 60 minute time-point for acetaminophen and the 5 minute time point for hydrocodone bitartrate were near the lower limits. FIG. 6 provides a graphical representation of the dissolution profile results for Example 17.

Example 18

Formulation design experiments were developed and run to optimize the product formulation to release the promethazine HCl faster than the acetaminophen and hydrocodone bitartrate. Initial tests showed that the dissolution profile was sensitive to hardness. Specifically, higher hardness tablets were releasing acetaminophen and hydrocodone bitartrate slower than the lower hardness tablet.

A product batch was manufactured at 9 kP tablet hardness. However, this seemed low for 700 mg tablets so as part of the formulation optimization the tablet hardness was increased from 9 kP to 12.5 KP. The focus of the formulation was on the acetaminophen/hydrocodone bitartrate layer of the bi-layer tablet. The total weight of the acetaminophen/hydrocodone bitartrate layer was held constant at 550 mgs by adjusting the level of silicified microcrystalline cellulose to compensate for the varying amounts of hydroxy propyl methyl cellulose and croscarmellose sodium in each of the formulations. The same promethazine layer blend was used as the second layer in each run and compressed at 150 mg per table for each run.

Example 18 - Promethazine Immediate Release Layer

| INGREDIENT | QUANTITY/TABLET (MGS) |
|---|---|
| Promethazine HCL | 12.5 |
| Silicified Microcrystalline Cellulose | 121.5 |
| Croscarmellose Sodium | 15.0 |
| Magnesium Stearate | 1.0 |

Example 18-Run 1

| INGREDIENT | QUANTITY/ TABLET (MGS) | HARDNESS (KP) AVG (RANGE) | THICKNESS (MM) AVG. (RANGE) |
|---|---|---|---|
| Acetaminophen 90% | 361.1 | 13.5 (12.5-14.3) | 6.50 (6.47-6.52) |
| Hydrocodone Bitartrate | 7.5 | — | — |
| Silicified Microcrystalline Cellulose | 171.4 | — | — |
| Hypromellose 2208 | 5 | — | — |
| Croscarmellose Sodium | 5 | — | — |

Example 18-Run 2

| INGREDIENT | QUANTITY/ TABLET (MGS) | HARDNESS (KP) AVG (RANGE) | THICKNESS (MM) AVG. (RANGE) |
|---|---|---|---|
| Acetaminophen 90% | 361.1 | 12.2 (11.0-13.2) | 6.70 (6.67-6.72) |
| Hydrocodone Bitartrate | 7.5 | — | — |
| Silicified Microcrystalline Cellulose | 156 | — | — |
| Hypromellose 2208 | 20 | — | — |
| Croscarmellose Sodium | 5 | — | — |

Example 18-Run 3\

| INGREDIENT | QUANTITY/ TABLET (MGS) | HARDNESS (KP) AVG (RANGE) | THICKNESS (MM) AVG. (RANGE) |
|---|---|---|---|
| Acetaminophen 90% | 361.1 | 12.4 (11.3-14.1) | 6.88 (6.66-6.72) |
| Hydrocodone Bitartrate | 7.5 | — | — |
| Silicified Microcrystalline Cellulose | 164.6 | — | — |
| Hypromellose 2208 | 18 | — | — |
| Croscarmellose Sodium | 1.5 | — | — |

Example 18-Run 4\

| INGREDIENT | QUANTITY/ TABLET (MGS) | HARDNESS (KP) AVG (RANGE) | THICKNESS (MM) AVG. (RANGE) |
|---|---|---|---|
| Acetaminophen 90% | 361.1 | 12.8 (11.6-14.2) | 6.65 (6.64-6.66) |
| Hydrocodone Bitartrate | 7.5 | — | — |
| Silicified Microcrystalline Cellulose | 158.9 | — | — |
| Hypromellose 2208 | 12.5 | — | — |
| Croscarmellose Sodium | 10 | — | — |

Example 18-Run 5\

| INGREDIENT | QUANTITY/ TABLET (MGS) | HARDNESS (KP) AVG (RANGE) | THICKNESS (MM) AVG. (RANGE) |
|---|---|---|---|
| Acetaminophen 90% | 361.1 | 12.3 (10.2-14.3) | 6.69 (6.62-6.77) |
| Hydrocodone Bitartrate | 7.5 | — | — |
| Silicified Microcrystalline Cellulose | 164.5 | — | — |
| Hypromellose 2208 | 12.5 | — | — |
| Croscarmellose Sodium | 5 | — | — |

Example 18-Run 6\

| INGREDIENT | QUANTITY/ TABLET (MGS) | HARDNESS (KP) AVG (RANGE) | THICKNESS (MM) AVG. (RAANGE) |
|---|---|---|---|
| Acetaminophen 90% | 361.1 | 12.0 (11.3-12.6) | 6.70 (6.63-6.76) |
| Hydrocodone Bitartrate | 7.5 | — | — |
| Silicified Microcrystalline Cellulose | 172.9 | — | — |
| Hypromellose 2208 | 7 | — | — |
| Croscarmellose Sodium | 1.5 | — | — |

Example 18-Run 7\

| INGREDIENT | QUANTITY/ TABLET (MGS) | HARDNESS (KP) AVG (RANGE) | THICKNESS (MM) AVG. (RANGE) |
|---|---|---|---|
| Acetaminophen 90% | 361.1 | 12.5 (11.3-13.8) | 6.62 (6.58-6.66) |
| Hydrocodone Bitartrate | 7.5 | — | — |
| Silicified Microcrystalline Cellulose | 165.9 | — | — |
| Hypromellose 2208 | 7 | — | — |
| Croscarmellose Sodium | 8.5 | — | — |

Example 18-Run 8

| INGREDIENT | QUANTITY/ TABLET (MGS) | HARDNESS (KP) AVG (RANGE) | THICKNESS (MM) AVG. (RANGE) |
|---|---|---|---|
| Acetaminophen 90% | 361.1 | 12.2 (11.2-13.2) | 6.63 (6.61-6.64) |
| Hydrocodone Bitartrate | 7.5 | — | — |
| Silicified Microcrystalline Cellulose | 163.9 | — | — |
| Hypromellose 2208 | 12.5 | — | — |
| Croscarmellose Sodium | 5 | — | — |

| Example 18-Run 9 | | | |
|---|---|---|---|
| INGREDIENT | QUANTITY/ TABLET (MGS) | HARDNESS (KP) AVG (RANGE) | THICKNESS (MM) AVG. (RANGE) |
| Acetaminophen 90% | 361.1 | 11.9 (11.1-13.2) | 6.66 (6.64-6.68) |
| Hydrocodone Bitartrate | 7.5 | — | — |
| Silicified Microcrystalline Cellulose | 168.4 | — | — |
| Hypromellose 2208 | 12.5 | — | — |
| Croscarmellose Sodium | 0 | — | — |

| Example 18-Run 10 | | | |
|---|---|---|---|
| INGREDIENT | QUANTITY/ TABLET (MGS) | HARDNESS (KP) AVG (RANGE) | THICKNESS (MM) AVG. (RANGE) |
| Acetaminophen 90% | 361.1 | 12.2 (11.2-13.1) | 6.66 (6.64-6.70) |
| Hydrocodone Bitartrate | 7.5 | — | — |
| Silicified Microcrystalline Cellulose | 154.9 | — | — |
| Hypromellose 2208 | 18 | — | — |
| Croscarmellose Sodium | 8.5 | — | — |

| Example 18-Run 11 | | | |
|---|---|---|---|
| INGREDIENT | QUANTITY/ TABLET (MGS) | HARDNESS (KP) AVG (RANGE) | THICKNESS (MM) AVG. (RANGE) |
| Acetaminophen 90% | 361.1 | 12.3 (11.7-13.1) | 6.65 (6.62-6.66) |
| Hydrocodone Bitartrate | 7.5 | — | — |
| Silicified Microcrystalline Cellulose | 163.9 | — | — |
| Hypromellose 2208 | 12.5 | — | — |
| Croscarmellose Sodium | 5 | — | — |

Table 2 below shows the acetaminophen (APAP) and hydrocodone bitartrate (HB) dissolution profile results for the three time points focused on in the design experiment.

TABLE 2

| | APAP @ 5 min | HB @ 5 min | APAP @ 30 min | HB @ 30 min | APAP @ 60 min | HB @ 60 min |
|---|---|---|---|---|---|---|
| | | | Target Range | | | |
| Run # | 35-70% | 25-60% | NLT 65% | NLT 65% | NLT 80% | NLT 80% |
| 1 | 83 | 88.7 | 90.1 | 100.6 | 93.8 | 105.3 |
| 2 | 44.7 | 29.9 | 75.6 | 81.1 | 85.2 | 94.5 |
| 3 | 51.7 | 39.6 | 76.7 | 80.0 | 84.5 | 91.2 |
| 4 | 64.0 | 52.1 | 96.9 | 98.8 | 97.8 | 99.7 |
| 5 | 71.6 | 59.0 | 96.2 | 98.7 | 96.7 | 99.6 |
| 6 | 83.4 | 91.3 | 88.6 | 97.8 | 91.9 | 100.8 |
| 7 | 89.2 | 98.3 | 92.4 | 100.7 | 94.8 | 101.5 |
| 8 | 68.7 | 57.1 | 85.5 | 86.8 | 91.3 | 93.5 |
| 9 | 76.9 | 69.8 | 93.2 | 95.8 | 95.2 | 98.8 |
| 10 | 45.5 | 30.1 | 80.0 | 83.1 | 89.9 | 96.0 |
| 11 | 73.6 | 63.6 | 96.6 | 100.5 | 95.1 | 98.2 |

Figure 7:
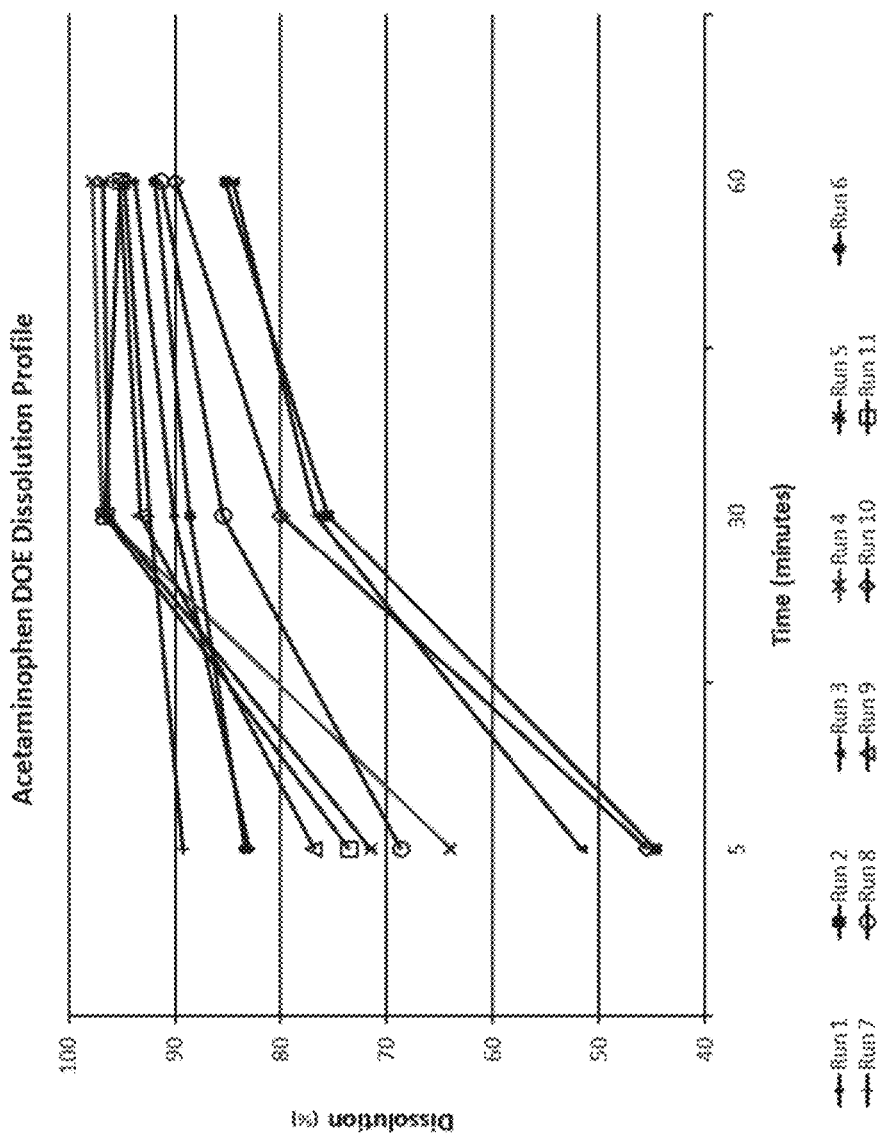
FIG. 7 illustrates an example of the acetaminophen dissolution release profiles for the analgesic compositions of Example 18.

FIG. 7 graphically depicts the acetaminophen dissolution results for all of the runs in Example 18. Example 18-run 2 had the slowest acetaminophen release and contained the highest amount of HPMC (20 mg/tablet). Example 18-run 4, which contained 10 mg croscarmellose sodium, was among the fastest for release of acetaminophen at 30 minutes and 60 minutes, but was among the slowest at 5 minutes.

FIG. 8 graphically depicts the hydrocodone bitartrate dissolution results for all of the runs in Example 18. Example 18-run 2 and Example 18-run 10 released slower than the other runs at 5 minutes. However, at 30 and 60 minutes Example 18-run 3 was the slowest.

Statistical analysis of the results showed that the Hypromellose significantly affected the dissolution profile of both Acetaminophen and Hydrocodone Bitartrate at every time point. Croscarmellose Sodium had no significant effect on APAP or HR. HPMC had a significant effect on Acetaminophen at only 30 and 60 minutes. While HPMC significantly affects dissolution profile for Acetaminophen, it did not affect Hydrocodone Bitartrate dissolution significantly. The optimized formulation based on the predictive equations yielded about 15.6 mg Hypromellose and 10 mg Croscarmellose Sodium in the controlled release layer.

Example 19

Based on the results from Example 18 a bi-layer tablet with optimized hydroxypropyl methyl cellulose and croscarmellose amounts was prepared.

| Example 19 - Immediate Release Layer (Top Layer) | |
|---|---|
| INGREDIENT | QUANTITY/ TABLET (MGS) |
| Promethazine HCL | 12.5 |
| Silicified Microcrystalline Cellulose | 121.5 |
| Croscarmellose Sodium | 15 |
| Magnesium Stearate | 1 |

| Example 19 - Controlled Release Layer (Bottom Layer) | |
|---|---|
| INGREDIENT | QUANTITY/ TABLET (MGS) |
| Acetaminophen 90% | 361.1 |
| Hydrocodone Bitartrate USP CII | 8.3* |

Example 19 - Controlled Release Layer (Bottom Layer)

| INGREDIENT | QUANTITY/TABLET (MGS) |
|---|---|
| Silicified Microcrystalline Cellulose | 149.6* |
| Hypromellose 2208 | 15.5 |
| Croscarmellose Sodium | 10.0 |
| Magnesium Stearate | 2.75 |
| Stearic Acid NF | 2.75 |

*The label claim for Hydrocodone Bitartrate USP CII is 7.5 mgs. Silicified Microcrystalline Cellulose is adjusted based on the potency of the Hydrocodone Bitartrate. The potency for the lost was calculated to be 90.4% (calculated using assay results and water content).

While particular embodiments described herein have been shown and described herein, such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating or preventing pain, and reducing or preventing an adverse effect associated with an opioid analgesic, comprising administering to a subject in need thereof an immediate-release bi-layered tablet that comprises:
   (1) a first layer that comprises:
      (a) 5 mg to 30 mg of an antiemetic that is promethazine or a pharmaceutically acceptable salt thereof;
      (b) about 75 mg to about 150 mg of silicified microcrystalline cellulose;
      (c) about 10 mg to about 20 mg of croscarmellose sodium; and
      (d) about 0.5 mg to 2 mg of magnesium stearate; and
   (2) a second layer that comprises:
      (a) about 200 mg to about 1000 mg of a non-opioid analgesic that is acetaminophen or a pharmaceutically acceptable salt thereof;
      (b) about 0.5 mg to about 20 mg of the opioid analgesic that is hydrocodone or a pharmaceutically acceptable salt thereof;
      (c) about 75 mg to about 250 mg of silicified microcrystalline cellulose;
      (d) about 10 mg to about 40 mg of hydroxypropyl methylcellulose;
      (e) about 0.5 mg to 5 mg of magnesium stearate; and
      (f) about 0.5 mg to about 5 mg of stearic acid,
   wherein the immediate-release bi-layered tablet provides an effective amount of the opioid analgesic and the non-opioid analgesic to treat or prevent pain in the subject in need thereof, and an effective amount of the antiemetic to reduce or prevent an adverse effect associated with the opioid analgesic in the subject in need thereof.

2. The method of claim 1, wherein the method treats pain and reduces vomiting associated with the opioid analgesic.

3. The method of claim 1, wherein the method treats pain and reduces nausea associated with the opioid analgesic.

4. The method of claim 1, wherein the method treats pain and reduces nausea and vomiting associated with the opioid analgesic.

5. The method of claim 1, wherein the subject in need thereof has a reduction in incidence of nausea or vomiting.

6. The method of claim 1, wherein the subject in need thereof has a reduction in intensity of nausea or vomiting.

7. The method of claim 1, wherein the administering to the subject in need thereof occurs at about every 4 to 6 hours.

8. The method of claim 1, wherein the pain is acute.

9. The method of claim 1, wherein the antiemetic is promethazine hydrochloride.

10. The method of claim 1, wherein the promethazine or the pharmaceutically acceptable salt thereof is present in an amount from 5 mg to 13 mg.

11. The method of claim 1, wherein the promethazine or the pharmaceutically acceptable salt thereof is present in an amount from about 10 mg to about 15 mg.

12. The method of claim 11, wherein the promethazine or the pharmaceutically acceptable salt thereof is present in an amount of about 12.5 mg.

13. The method of claim 1, wherein the opioid analgesic is hydrocodone bitartrate.

14. The method of claim 1, wherein the hydrocodone or the pharmaceutically acceptable salt thereof is present in an amount from about 1 mg to about 15 mg.

15. The method of claim 1, wherein the hydrocodone or the pharmaceutically acceptable salt thereof is present in an amount from about 5 mg to about 12 mg.

16. The method of claim 15, wherein the hydrocodone or the pharmaceutically acceptable salt thereof is present in an amount from about 6.5 mg to about 8.5 mg.

17. The method of claim 16, wherein the hydrocodone or the pharmaceutically acceptable salt thereof is present in an amount of about 7.5 mg.

18. The method of claim 1, wherein the acetaminophen or the pharmaceutically acceptable salt thereof is present in an amount from about 275 mg to about 405 mg.

19. The method of claim 18, wherein the acetaminophen or the pharmaceutically acceptable salt thereof is present in an amount from 310 mg to 330 mg.

20. The method of claim 19, wherein the acetaminophen or the pharmaceutically acceptable salt thereof is present in an amount of about 325 mg.

21. The method of claim 1, wherein: the promethazine or the pharmaceutically acceptable salt thereof is present in an amount from 5 mg to 13 mg; the hydrocodone or the pharmaceutically acceptable salt thereof is present in an amount from 6 mg to 8 mg; and the acetaminophen or the pharmaceutically acceptable salt thereof is present in an amount from 310 mg to 330 mg.

22. The method of claim 21, wherein: the promethazine or the pharmaceutically acceptable salt thereof is present in an amount of 12.5 mg; the hydrocodone or the pharmaceutically acceptable salt thereof is present in an amount of about 7.5 mg; and the acetaminophen or the pharmaceutically acceptable salt thereof is present in an amount of about 325 mg.

23. The method of claim 1, wherein the method treats pain and reduces nausea and vomiting associated with the opioid analgesic, and wherein: the antiemetic is promethazine hydrochloride that is present in an amount of about 12.5 mg; the opioid analgesic is hydrocodone bitartrate that is present in an amount of about 7.5 mg; and the non-opioid analgesic is acetaminophen that is present in an amount of about 325 mg.

24. The method of claim 1, wherein the method treats pain and reduces nausea and vomiting associated with the opioid analgesic, wherein the administering to the subject in need thereof occurs at about every 4 to 6 hours, and wherein: the antiemetic is promethazine hydrochloride that is present in an amount of about 12.5 mg; the opioid analgesic is hydrocodone bitartrate that is present in an amount of about 7.5 mg; and the non-opioid analgesic is acetaminophen that is present in an amount of about 325 mg.

25. The method of claim 24,
wherein, in the first layer:
the silicified microcrystalline cellulose is present in an amount from about 100 mg to about 140 mg;
the croscarmellose sodium is present in an amount from about 12 mg to about 18 mg; and
the magnesium stearate is present in an amount from about 0.8 mg to about 1.5 mg; and
wherein, in the second layer:
the silicified microcrystalline cellulose is present in an amount from about 120 mg to about 170 mg;
the hydroxypropyl methylcellulose is present in an amount from about 12 mg to about 20 mg;
the magnesium stearate is present in an amount from about 2 mg to 3.5 mg; and
the stearic acid is present in an amount from about 2 mg to about 3.5 mg.

26. The method of claim 25, wherein the second layer further comprises about 5 mg to about 25 mg of croscarmellose sodium.

27. The method of claim 26, wherein the croscarmellose sodium is present in an amount from about 8 mg to about 12 mg.

28. The method of claim 27, wherein the croscarmellose sodium is present in an amount of about 10 mg.

29. The method of claim 1, wherein the immediate-release bi-layered tablet further comprises an effective amount of an abuse deterrent agent.

30. An immediate-release bi-layered tablet for treatment or prevention of pain, and reduction or prevention of an adverse effect associated with an opioid analgesic, wherein the immediate-release bi-layered tablet comprises:
(1) a first layer that comprises:
(a) 5 mg to 30 mg of an antiemetic that is promethazine or a pharmaceutically acceptable salt thereof;
(b) about 75 mg to about 150 mg of silicified microcrystalline cellulose;
(c) about 10 mg to about 20 mg of croscarmellose sodium; and
(d) about 0.5 mg to 2 mg of magnesium stearate; and
(2) a second layer that comprises:
(a) about 200 mg to about 1000 mg of a non-opioid analgesic that is acetaminophen or a pharmaceutically acceptable salt thereof;
(b) about 0.5 mg to about 20 mg of the opioid analgesic that is hydrocodone or a pharmaceutically acceptable salt thereof;
(c) about 75 mg to about 250 mg of silicified microcrystalline cellulose;
(d) about 10 mg to about 40 mg of hydroxypropyl methylcellulose;
(e) about 0.5 mg to 5 mg of magnesium stearate; and
(f) about 0.5 mg to about 5 mg of stearic acid.

31. The method of claim 1, wherein the antiemetic is promethazine that is present in an amount of about 11 mg.

32. The method of claim 1, wherein the opioid analgesic is hydrocodone that is present in an amount of about 5 mg.

33. The method of claim 1, wherein the non-opioid analgesic is acetaminophen that is present in an amount of about 325 mg.

34. The method of claim 1, wherein: the antiemetic is promethazine hydrochloride that is present in an amount of about 12.5 mg; the opioid analgesic is hydrocodone bitartrate that is present in an amount of about 7.5 mg; and the non-opioid analgesic is acetaminophen that is present in an amount of about 325 mg.

35. The immediate-release bi-layered tablet of claim 30, wherein the antiemetic is promethazine hydrochloride.

36. The immediate-release bi-layered tablet of claim 30, wherein the promethazine or the pharmaceutically acceptable salt thereof is present in an amount from 5 mg to 13 mg.

37. The immediate-release bi-layered tablet of claim 30, wherein the promethazine or the pharmaceutically acceptable salt thereof is present in an amount from about 10 mg to about 15 mg.

38. The immediate-release bi-layered tablet of claim 30, wherein the promethazine or the pharmaceutically acceptable salt thereof is present in an amount of about 12.5 mg.

39. The immediate-release bi-layered tablet of claim 30, wherein the antiemetic is promethazine that is present in an amount of about 11 mg.

40. The immediate-release bi-layered tablet of claim 30, wherein the opioid analgesic is hydrocodone bitartrate.

41. The immediate-release bi-layered tablet of claim 30, wherein the hydrocodone or the pharmaceutically acceptable salt thereof is present in an amount from about 1 mg to about 15 mg.

42. The immediate-release bi-layered tablet of claim 30, wherein the hydrocodone or the pharmaceutically acceptable salt thereof is present in an amount from about 5 mg to about 12 mg.

43. The immediate-release bi-layered tablet of claim 30, wherein the hydrocodone or the pharmaceutically acceptable salt thereof is present in an amount from about 6.5 mg to about 8.5 mg.

44. The immediate-release bi-layered tablet of claim 30, wherein the hydrocodone or the pharmaceutically acceptable salt thereof is present in an amount of about 7.5 mg.

45. The immediate-release bi-layered tablet of claim 30, wherein the opioid analgesic is hydrocodone that is present in an amount of about 5 mg.

46. The immediate-release bi-layered tablet of claim 30, wherein the acetaminophen or the pharmaceutically acceptable salt thereof is present in an amount from about 275 mg to about 405 mg.

47. The immediate-release bi-layered tablet of claim 30, wherein the acetaminophen or the pharmaceutically acceptable salt thereof is present in an amount from 310 mg to 330 mg.

48. The immediate-release bi-layered tablet of claim 30, wherein the acetaminophen or the pharmaceutically acceptable salt thereof is present in an amount of about 325 mg.

49. The immediate-release bi-layered tablet of claim 30, wherein the non-opioid analgesic is acetaminophen that is present in an amount of about 325 mg.

50. The immediate-release bi-layered tablet of claim 30, wherein: the promethazine or the pharmaceutically acceptable salt thereof is present in an amount from 5 mg to 13 mg; the hydrocodone or the pharmaceutically acceptable salt thereof is present in an amount from 6 mg to 8 mg; and the acetaminophen or the pharmaceutically acceptable salt thereof is present in an amount from 310 mg to 330 mg.

51. The immediate-release bi-layered tablet of claim 30, wherein: the promethazine or the pharmaceutically acceptable salt thereof is present in an amount of 12.5 mg; the hydrocodone or the pharmaceutically acceptable salt thereof is present in an amount of about 7.5 mg; and the acetaminophen or the pharmaceutically acceptable salt thereof is present in an amount of about 325 mg.

52. The immediate-release bi-layered tablet of claim 30, wherein: the antiemetic is promethazine hydrochloride that is present in an amount of about 12.5 mg; the opioid analgesic is hydrocodone bitartrate that is present in an amount of about 7.5 mg; and the non-opioid analgesic is acetaminophen that is present in an amount of about 325 mg.

53. The immediate-release bi-layered tablet of claim 52, wherein, in the first layer:
the silicified microcrystalline cellulose is present in an amount from about 100 mg to about 140 mg;
the croscarmellose sodium is present in an amount from about 12 mg to about 18 mg; and
the magnesium stearate is present in an amount from about 0.8 mg to about 1.5 mg; and wherein, in the second layer:
the silicified microcrystalline cellulose is present in an amount from about 135 mg to about 170 mg;
the hydroxypropyl methylcellulose is present in an amount from about 12 mg to about 20 mg;
the magnesium stearate is present in an amount from about 2 mg to 3.5 mg; and
the stearic acid is present in an amount from about 2 mg to about 3.5 mg.

54. The immediate-release bi-layered tablet of claim 53, wherein the second layer further comprises about 5 mg to about 25 mg of croscarmellose sodium.

55. The immediate-release bi-layered tablet of claim 54, wherein the croscarmellose sodium is present in an amount from about 8 mg to about 12 mg.

56. The immediate-release bi-layered tablet of claim 55, wherein the croscarmellose sodium is present in an amount of about 10 mg.

57. The immediate-release bi-layered tablet of claim 30, wherein the immediate-release bi-layered tablet further comprises an effective amount of an abuse deterrent agent.

* * * * *